(12) United States Patent
Moore et al.

(10) Patent No.: US 7,718,612 B2
(45) Date of Patent: May 18, 2010

(54) PYRIDAZINONYL MACROCYCLIC HEPATITIS C SERINE PROTEASE INHIBITORS

(75) Inventors: Joel D. Moore, Lexington, MA (US); Datong Tang, Newton, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 83 days.

(21) Appl. No.: 11/832,893

(22) Filed: Aug. 2, 2007

(65) Prior Publication Data
US 2009/0035272 A1    Feb. 5, 2009

Related U.S. Application Data

(60) Provisional application No. 61/007,900, filed on Aug. 4, 2006.

(51) Int. Cl.
A61K 38/12    (2006.01)
C07K 5/12    (2006.01)

(52) U.S. Cl. .................................. 514/11; 530/317
(58) Field of Classification Search ................. None
See application file for complete search history.

(56) References Cited

U.S. PATENT DOCUMENTS

| | | | |
|---|---|---|---|
| 6,268,207 B1 * | 7/2001 | Bailey | 435/280 |
| 6,608,027 B1 * | 8/2003 | Tsantrizos et al. | 514/9 |
| 6,908,901 B2 * | 6/2005 | Bailey et al. | 514/18 |
| 6,919,423 B2 * | 7/2005 | Llinas-Brunet | 514/18 |
| 7,091,184 B2 * | 8/2006 | Llinas-Brunet et al. | 514/18 |
| 7,119,072 B2 * | 10/2006 | Llinas-Brunet et al. | 514/18 |
| 7,173,004 B2 | 2/2007 | McPhee et al. | |
| 7,176,208 B2 | 2/2007 | Nakajima et al. | |
| 7,504,378 B2 * | 3/2009 | Llinas-Brunet et al. | 514/9 |
| 2003/0181363 A1 * | 9/2003 | Llinas-Brunet et al. | 514/9 |
| 2003/0186895 A1 * | 10/2003 | Llinas-Brunet et al. | 514/18 |
| 2003/0224977 A1 * | 12/2003 | Llinas-Brunet et al. | 514/9 |
| 2004/0180815 A1 | 9/2004 | Nakajima et al. | |
| 2005/0020503 A1 * | 1/2005 | Llinas-Brunet et al. | 514/18 |
| 2005/0065073 A1 * | 3/2005 | Wu et al. | 514/10 |
| 2005/0075279 A1 * | 4/2005 | Llinas-Brunet et al. | 514/9 |
| 2005/0080005 A1 * | 4/2005 | Llinas-Brunet et al. | 514/10 |
| 2005/0153877 A1 * | 7/2005 | Miao et al. | 514/10 |
| 2006/0019905 A1 * | 1/2006 | Bailey et al. | 514/18 |
| 2006/0046965 A1 * | 3/2006 | Bailey et al. | 514/19 |
| 2006/0089300 A1 * | 4/2006 | Llinas-Brunet et al. | 514/9 |
| 2007/0060510 A1 | 3/2007 | Nakajima et al. | |
| 2007/0099825 A1 | 5/2007 | D'Andrea et al. | |

FOREIGN PATENT DOCUMENTS

| WO | WO 2004037855 A1 * | 5/2004 |
|---|---|---|
| WO | WO 2004072243 A2 * | 8/2004 |
| WO | WO 2004101602 A2 * | 11/2004 |
| WO | WO 2004101605 A1 * | 11/2004 |
| WO | WO 2004103996 A1 * | 12/2004 |
| WO | WO 2004113365 A2 * | 12/2004 |

OTHER PUBLICATIONS

H.-K. Han. AAPS Pharmsci. (2000) 2(1), article 6, pp. 1-11.*
P. Ettmayer et al. J. Med. Chem. (2004) 47(10), pp. 2393-2404.*
B. Testa. Biochem. Pharm. (2004) 68, pp. 2097-2106.*
Y.S. Tsantrizos et al. Angew. Chem. Int. Ed. (2003) 42(12), pp. 1355-1360.*
U.S. Appl. No. 11/832,240, filed Aug. 1, 2007, Sun et al.
U.S. Appl. No. 11/835,157, filed Aug. 7, 2007, Sun et al.
U.S. Appl. No. 11/831,474, filed Jul. 31, 2007, Moore et al.
R.C. Griffith et al., "HCV Anti-viral Agents", Annual Reports in Medicinal Chemistry, vol. 39, p. 223-237. (2004 Elsevier Inc.).

* cited by examiner

*Primary Examiner*—Andrew D Kosar
(74) *Attorney, Agent, or Firm*—Elmore Patent Law Group, P.C.; Roy P. Issac; Carolyn S. Elmore

(57) ABSTRACT

The present invention relates to compounds of Formula I, or pharmaceutically acceptable salts, esters, or prodrugs thereof, which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising a compound of the present invention.

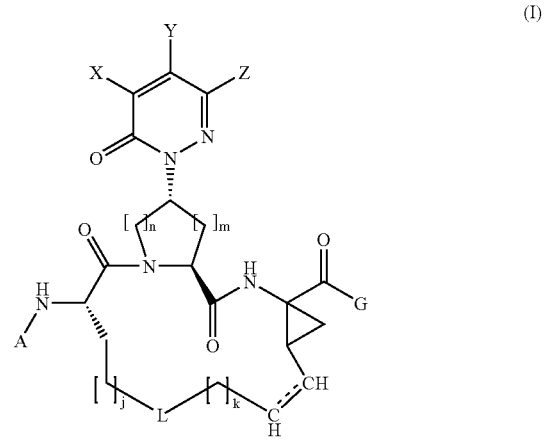

4 Claims, No Drawings

US 7,718,612 B2

PYRIDAZINONYL MACROCYCLIC HEPATITIS C SERINE PROTEASE INHIBITORS

CROSS-REFERENCE TO RELATED APPLICATIONS

This application claims the benefit from the U.S. Provisional Patent Application No. 61/007,900, filed on 4 Aug. 2006.

TECHNICAL FIELD

The present invention relates to compounds possessing inhibitory activity against the hepatitis C virus (HCV), and therefore useful in the treatment of HCV infections. More particularly, the invention relates to pyridazinone-containing compounds and compositions containing such compounds. The invention also relates to methods for using the compounds of the present invention as well as processes for making them.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-alpha (IFN-α), while a new approved second-generation treatment involves co-treatment with IFN-α and the general antiviral nucleoside mimics like ribavirin. Both of these treatments suffer from interferon-related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug preferably possesses significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides, which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3-NS4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease, which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov., 1, 867-881 (2002). Patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999); US publications 20050153877, 20050261200 and 20050065073.

SUMMARY OF THE INVENTION

The present invention relates to pyridazinone containing HCV macrocyclic protease inhibitors, and pharmaceutically acceptable salts, esters, or prodrugs thereof, which inhibit serine protease activity, particularly the activity of hepatitis C virus (HCV) NS3-NS4A protease. Consequently, said macrocyclic compounds of the present invention interfere with the life cycle of the hepatitis C virus and are also useful as antiviral agents. The present invention further relates to pharmaceutical compositions comprising the aforementioned compounds, salts, esters or prodrugs for administration to a subject suffering from HCV infection. The present invention further features pharmaceutical compositions comprising a compound of the present invention (or a pharmaceutically acceptable salt, ester or prodrug thereof) and another anti-HCV agent, such as interferon (e.g., alpha-interferon, beta-interferon, consensus interferon, pegylated interferon, or albumin or other conjugated interferon), ribavirin, amantadine, another HCV protease inhibitor, or an HCV polymerase, helicase or internal ribosome entry site inhibitor. The invention also relates to methods of treating an HCV infection in a subject by administering a pharmaceutical composition of the present invention.

In one embodiment of the present invention there are disclosed compounds represented by Formula I, or pharmaceutically acceptable salts, esters, or prodrugs thereof:

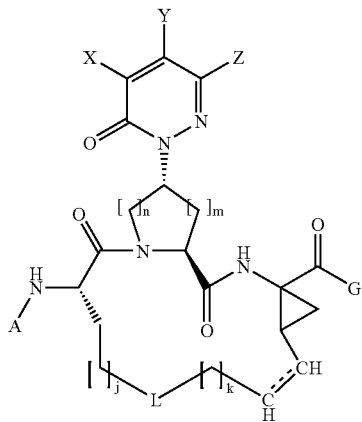

(I)

wherein

A is selected from —(C=O)—O—$R^1$, —(C=O)—$R^2$, —C(=O)—$NR^1R^2$, or —S(O)$_2$—$R^1$, —S(O)$_2$—N $R^1R^2$;

Wherein, $R^1$ is independently selected at each occurrence from the following groups:
(i) aryl;
(ii) substituted aryl;
(iii) heteroaryl;
(iv) substituted heteroaryl;
(v) heterocycloalkyl;
(vi) substituted heterocycloalkyl; and
(vii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

wherein, $R^2$ is independently selected at each occurrence from the following groups:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

G is selected from the group consisting of —NHS(O)$_2$—$R^3$ and —NH(SO$_2$)$NR^4R^5$;

wherein, $R^3$ is independently selected at each occurrence from the following groups:
(i) aryl;
(ii) substituted aryl;
(iii) heteroaryl;
(iv) substituted heteroaryl;
(v) heterocycloalkyl;
(vi) substituted heterocycloalkyl; and
(vii) —$C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

provided that $R^3$ is not —CH$_2$Ph or —CH$_2$CH$_2$Ph;

wherein, $R^4$ and $R^5$ are independently selected at each occurrence from the following groups:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

L is selected from the group consisting of —CH$_2$—, —O—, —S—, and —S(O)$_2$—;

X, Y, and Z are independently selected at each occurrence from the following groups:
(i) hydrogen;
(ii) —CN;
(iii) —N$_3$;
(iv) halogen;
(v) OR$^6$;
(vi) NR$^7$R$^8$;
(vii) aryl;
(viii) substituted aryl;
(ix) heteroaryl;
(x) substituted heteroaryl;
(xi) —$C_3$-$C_{12}$ cycloalkyl, substituted —$C_3$-$C_{12}$ cycloalkyl, heterocycloalkyl, substituted heterocycloalkyl;
(xii) —$C_1$-$C_6$ alkyl containing 0, 1, 2, or 3 heteroatoms selected from O, S, or N, optionally substituted with one or more substituent selected from halogen, aryl, substituted aryl, heteroaryl, or substituted heteroaryl;
(xiii) —$C_2$-$C_6$ alkenyl containing 0, 1, 2, or 3 heteroatoms selected from O, S, or N, optionally substituted with one or more substituent selected from halogen, aryl, substituted aryl, heteroaryl, or substituted heteroaryl; and
(xiv) —$C_2$-$C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;

or, in the alternative, X and Y or Y and Z taken together with the carbon atoms to which they are attached form a cyclic moiety, which is selected from aryl, substituted aryl, heteroaryl, or substituted heteroaryl;

wherein, $R^6$ is independently selected at each occurrence from the following groups:

(i) hydrogen
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

wherein, $R^7$ and $R^8$ are independently selected at each occurrence from the following groups:

(i) hydrogen;
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

----denotes a carbon-carbon single or double bond.
j=0, 1, 2, 3, or 4;
k=1, 2, or 3;
m=0, 1, or 2; and
n=1, 2, or 3.

DETAILED DESCRIPTION OF THE INVENTION

A first embodiment of the invention is a compound represented by Formula I as described above, or a pharmaceutically acceptable salt, ester or prodrug thereof, alone or in combination with a pharmaceutically acceptable carrier or excipient.

In another embodiment of the invention is a compound represented by Formula II:

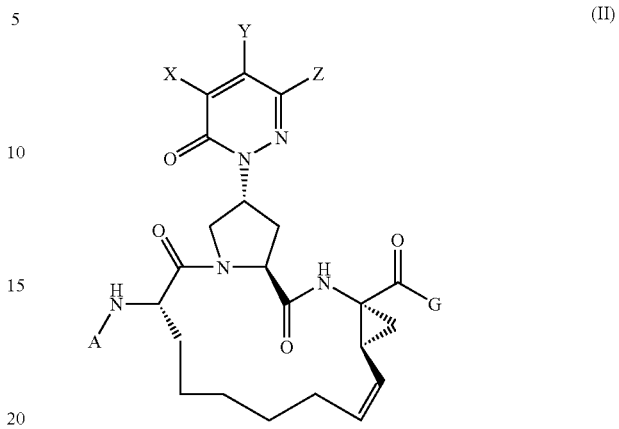

(II)

or a pharmaceutically acceptable salt, ester or prodrug thereof, alone or in combination with a pharmaceutically acceptable carrier or excipient herein, where A, G, X, Y, and Z are as previously defined in the previous embodiment.

In one example, X, Y and Z are independently selected from the group consisting of hydrogen, halogen, azido, cyano, $OR^6$, $NR^7R^8$, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; where each —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl and substituted —$C_2$-$C_8$ alkynyl independently contains 0, 1, 2 or 3 heteroatoms selected from O, S or N; where $R^6$, $R^7$ and $R^8$ are as previously defined in the previous embodiment. A is selected from the group consisting of —C(O)—$R_1$, —C(O)—O—$R_1$ and —C(O)—NH—$R_1$, where $R_1$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, X, Y and Z are independently selected from the group consisting of hydrogen, $OR^6$, $NR^7R^8$, aryl, substituted aryl, heteroaryl, and substituted heteroaryl; where $R^6$, $R^7$ and $R^8$ are as previously defined in the previous embodiment. A is —C(O)—O—$R_1$ or —C(O)—NH—$R_1$, where $R_1$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from aryl, substituted aryl, heteroaryl, substituted heteroaryl, heterocyclic, substituted heterocyclic, —$C_1$-$C_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In still yet another example, X, Y and Z are independently selected from the group consisting of hydrogen, OR$^6$, NR$^7$R$^8$, aryl, substituted aryl, heteroaryl, and substituted heteroaryl; where R$^6$, R$^7$ and R$^8$ are as previously defined in the previous embodiment. A is —C(O)—O—R$_1$, where R$_1$ is —C$_3$-C$_{12}$ cycloalkyl or substituted —C$_3$-C$_{12}$ cycloalkyl. G is —NHSO$_2$—R$_3$, where R$_3$ is selected from —C$_3$-C$_{12}$ cycloalkyl or substituted —C$_3$-C$_{12}$ cycloalkyl.

In another example, X, Y and Z are independently selected from the group consisting of hydrogen, OR$^6$, NR$^7$R$^8$, aryl, substituted aryl, heteroaryl, and substituted heteroaryl; where R$^6$, R$^7$ and R$^8$ are as previously defined in the previous embodiment. A is —C(O)—NH—R$_1$, where R$_1$ is —C$_1$-C$_8$ alkyl or substituted —C$_1$-C$_8$ alkyl. G is —NHSO$_2$—R$_3$, where R$_3$ is selected from —C$_3$-C$_{12}$ cycloalkyl or substituted —C$_3$-C$_{12}$ cycloalkyl.

In one example, X is OR$^6$, Y is aryl or heteroaryl, and Z is hydrogen or lower alkyl; where R$^6$ is as previously defined in the previous embodiment. A is —C(O)—O—R$_1$, where R$_1$ is —C$_1$-C$_8$ alkyl, substituted —C$_1$-C$_8$ alkyl, C$_3$-C$_{12}$ cycloalkyl or substituted —C$_3$-C$_{12}$ cycloalkyl. G is —NHSO$_2$—R$_3$, where R$_3$ is selected from —C$_3$-C$_{12}$ cycloalkyl or substituted —C$_3$-C$_{12}$ cycloalkyl.

In still another embodiment, the present invention features compounds of Formulae I or II, or pharmaceutically acceptable salts, esters or prodrug thereof, wherein A, G, X, Y, and Z are as previously defined in the first embodiment, and wherein X and Y, or Y and Z, taken together with the carbon atoms to which they are attached form a cyclic moiety which is selected from aryl, substituted aryl, heteroaryl, or substituted heteroaryl, and said cyclic moiety can be further optionally fused with another aryl, substituted aryl, heteroaryl, or substituted heteroaryl.

In one example, the present invention features compounds of Formula II, or pharmaceutically acceptable salts, esters or prodrug thereof, wherein X and Y (or Y and Z) taken together with the carbon atoms to which they are attached form a cyclic moiety which is selected from aryl, substituted aryl, heteroaryl, or substituted heteroaryl, and said cyclic moiety can be further optionally fused with another aryl, substituted aryl, heteroaryl, or substituted heteroaryl; and wherein Z (or X if Y and Z forms the cyclic moiety) is selected from the group consisting of hydrogen, halogen, azido, cyano, OR$^6$, NR$^7$R$^8$, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl; where each —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl and substituted —C$_2$-C$_8$ alkynyl independently contains 0, 1, 2 or 3 heteroatoms selected from O, S or N; where R$^6$, R$^7$ and R$^8$ are as previously defined in the first embodiment. A is selected from the group consisting of —C(O)—R$_1$, —C(O)—O—R$_1$ and —C(O)—NH—R$_1$, where R$_1$ is selected from aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. G can be —NH—SO$_2$—NH—R$_3$ or —NHSO$_2$—R$_3$, where R$_3$ is selected from hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In another example, the present invention features compounds of Formula II, or pharmaceutically acceptable salts, esters or prodrug thereof, wherein X and Y (or Y and Z) taken together with the carbon atoms to which they are attached form a cyclic moiety which is selected from aryl, substituted aryl, heteroaryl, or substituted heteroaryl, and said cyclic moiety can be further optionally fused with another aryl (e.g., a benzene ring), substituted aryl, heteroaryl, or substituted heteroaryl; and wherein Z (or X if Y and Z forms the cyclic moiety) is selected from the group consisting of hydrogen, OR$^6$, NR$^7$R$^8$, aryl, substituted aryl, heteroaryl, and substituted heteroaryl; where R$^6$, R$^7$ and R$^8$ are as previously defined in the first embodiment. A is —C(O)—O—R$_1$ or —C(O)—NH—R$_1$, where R$_1$ is —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. G is —NHSO$_2$—R$_3$, where R$_3$ is selected from aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. For instance, A can be —C(O)—O—R$_1$, where R$_1$ is —C$_3$-C$_{12}$ cycloalkyl or substituted —C$_3$-C$_{12}$ cycloalkyl; and G can be —NHSO$_2$—R$_3$, where R$_3$ is selected from —C$_3$-C$_{12}$ cycloalkyl or substituted —C$_3$-C$_{12}$ cycloalkyl. For another instance, A can be —C(O)—NH—R$_1$, where R$_1$ is —C$_1$-C$_8$ alkyl or substituted —C$_1$-C$_8$ alkyl; and G can be —NHSO$_2$—R$_3$, where R$_3$ is selected from —C$_3$-C$_{12}$ cycloalkyl or substituted —C$_3$-C$_{12}$ cycloalkyl. In some cases, X and Y, taken together with the carbon atoms to which they are attached, form substituted or unsubstituted

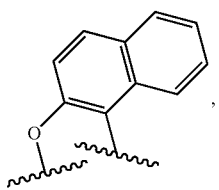

and Z can be hydrogen or C$_1$-C$_6$alkyl.

Representative compounds of the invention include, but are not limited to, the following compounds (table 1) according to Formula III:

TABLE 1
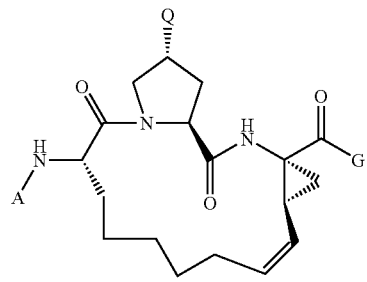
(III)
| Example # | A | Q | G |
|---|---|---|---|
| 16 | | | |
| 17 | | | |
| 18 | | | |
| 19 | | | |

TABLE 1-continued
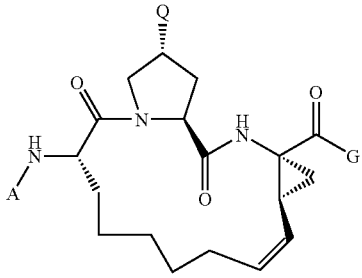
(III)
| Example # | A | Q | G |
|---|---|---|---|
| 20 | 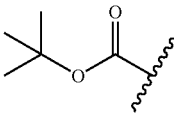 | 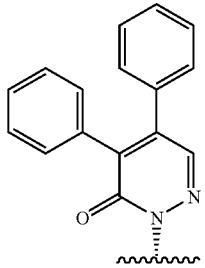 | 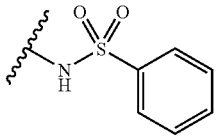 |
| 21 | 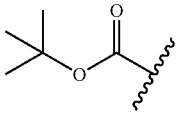 | 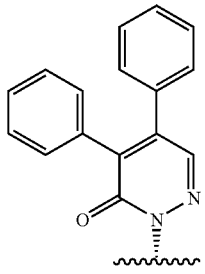 | 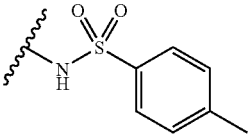 |
| 22 | 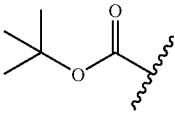 | 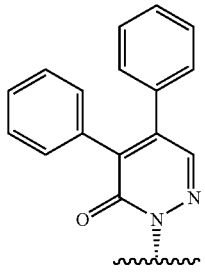 | 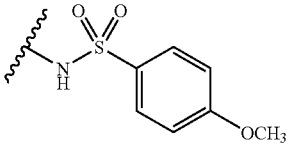 |
| 23 | 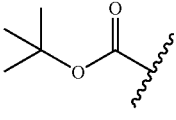 | 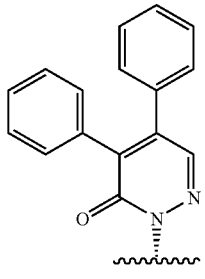 | 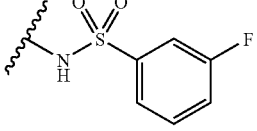 |

TABLE 1-continued
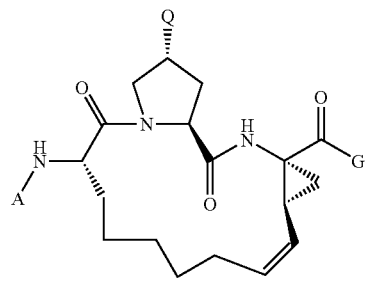
(III)
| Example # | A | Q | G |
|---|---|---|---|
| 24 | tert-butyl ester | 4,5-diphenyl-pyridazin-3(2H)-on-2-yl | NHSO₂CH₂CF₃ |
| 25 | tert-butyl ester | 4,5-diphenyl-pyridazin-3(2H)-on-2-yl | NHSO₂(6-chloropyridin-3-yl) |
| 26 | tert-butyl ester | 4,5-diphenyl-pyridazin-3(2H)-on-2-yl | NHSO₂(5-methylpyridin-2-yl) |
| 27 | tert-butyl ester | 4,5-diphenyl-pyridazin-3(2H)-on-2-yl | NHSO₂(1-methylimidazol-4-yl) |

TABLE 1-continued
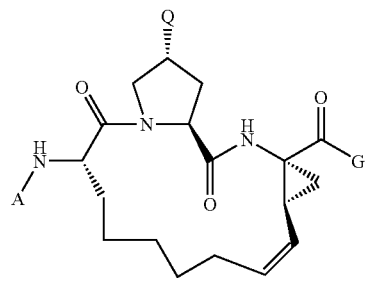
(III)
| Example # | A | Q | G |
|---|---|---|---|
| 28 | 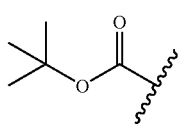 | 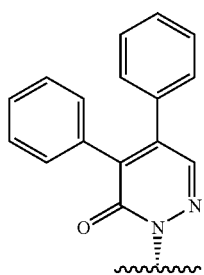 | 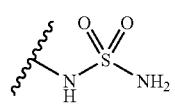 |
| 29 | 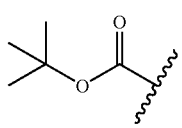 | 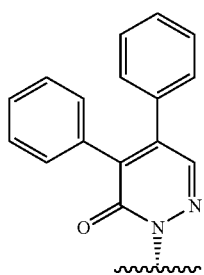 | 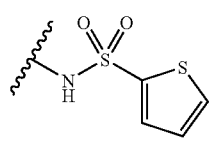 |
| 30 | 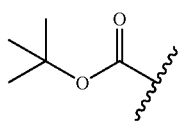 | 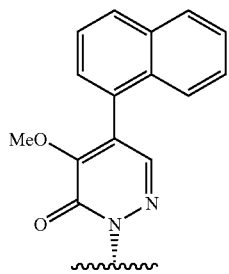 | 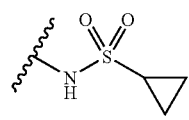 |
| 31 | 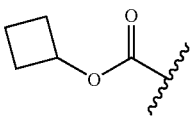 | 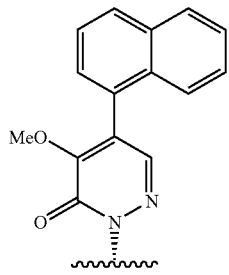 | 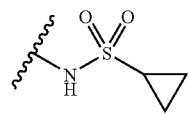 |

TABLE 1-continued
(III)
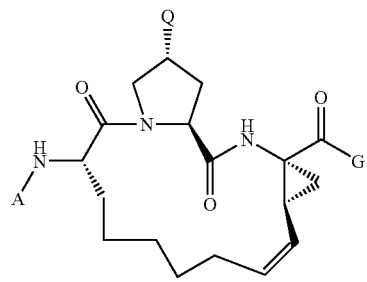
| Example # | A | Q | G |
|---|---|---|---|
| 32 | 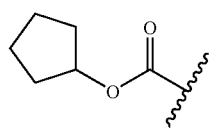 | 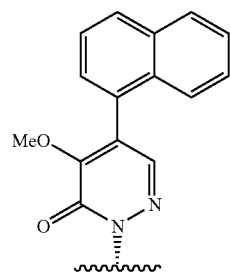 | 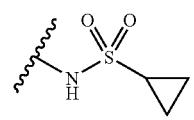 |
| 33 | 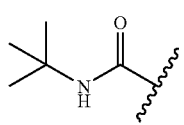 | 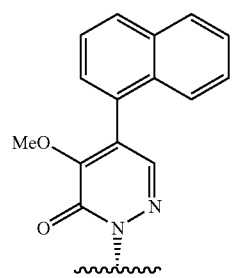 | 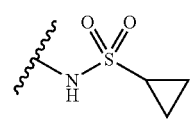 |
| 34 | 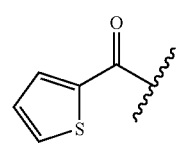 | 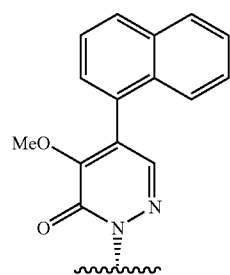 | 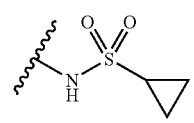 |
| 35 | 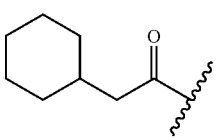 | 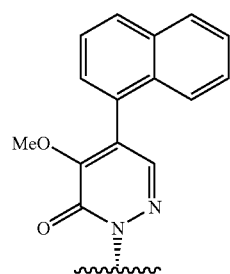 | 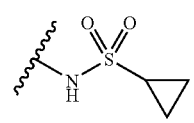 |

TABLE 1-continued
(III)
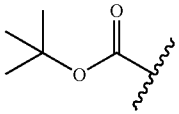
| Example # | A | Q | G |
|---|---|---|---|
| 36 | 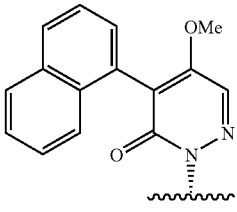 | 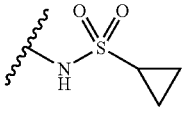 | 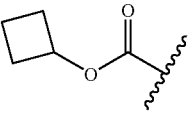 |
| 37 | 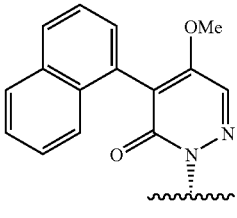 | 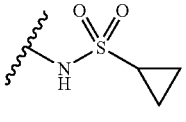 | 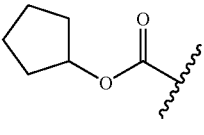 |
| 38 | 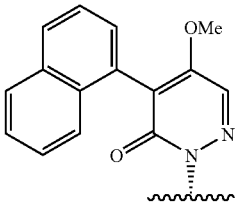 | 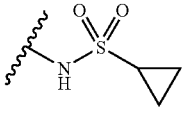 | 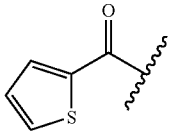 |
| 39 | 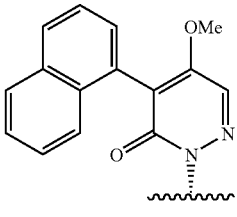 | 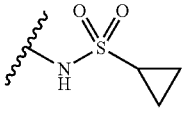 | 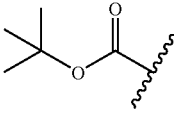 |
| 40 | 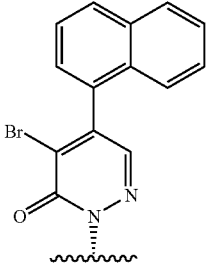 | 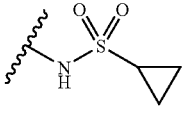 | |

TABLE 1-continued
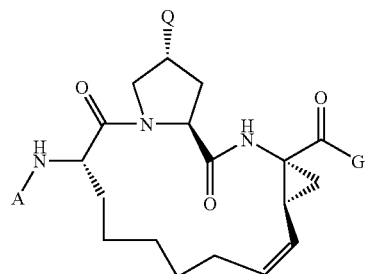
(III)
| Example # | A | Q | G |
|---|---|---|---|
| 41 | 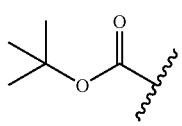 | 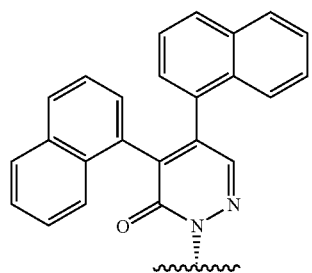 | 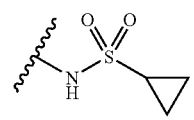 |
| 42 | 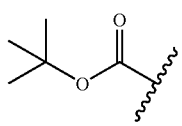 | 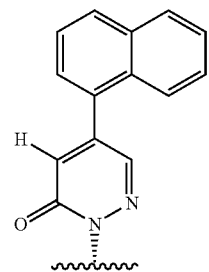 | 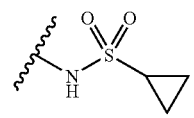 |
| 43 | 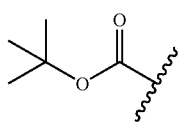 | 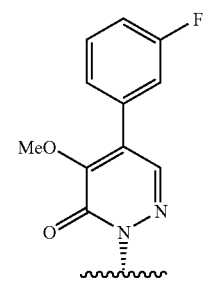 | 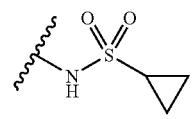 |
| 44 | 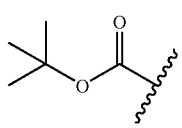 | 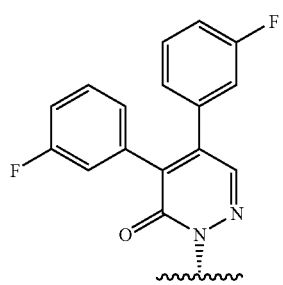 | 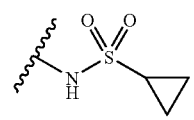 |

TABLE 1-continued
(III)
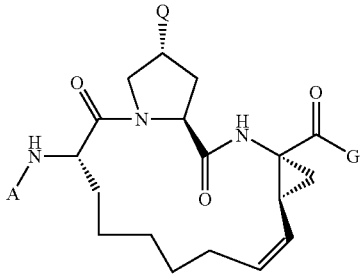
| Example # | A | Q | G |
|---|---|---|---|
| 45 | 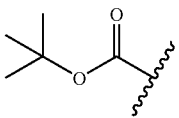 | 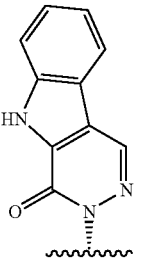 | 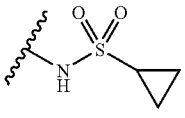 |
| 46 | 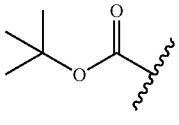 | 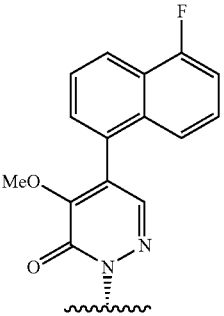 | 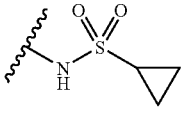 |
| 47 | 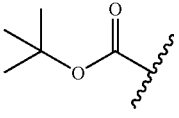 | 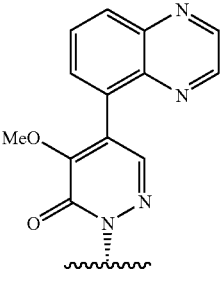 | 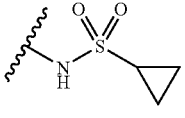 |
| 48 | 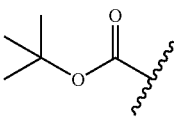 | 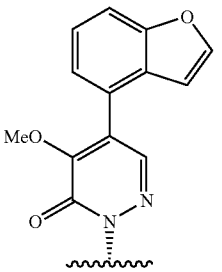 | 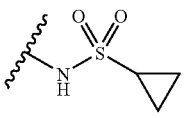 |

TABLE 1-continued
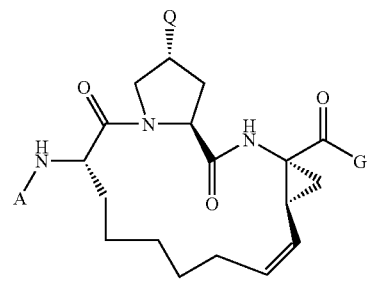
(III)
| Example # | A | Q | G |
|---|---|---|---|
| 49 | 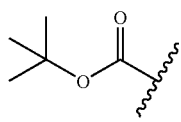 | 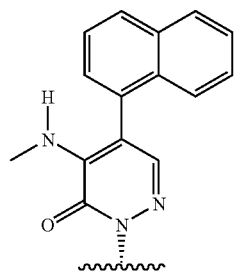 | 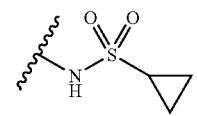 |
| 50 | 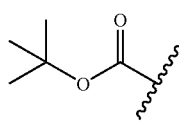 | 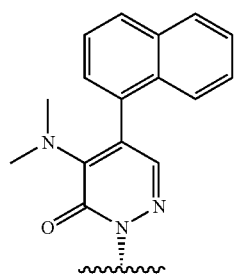 | 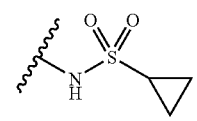 |
| 51 | 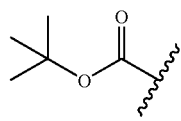 | 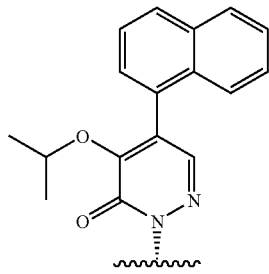 | 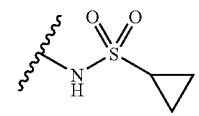 |
| 52 | 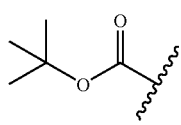 | 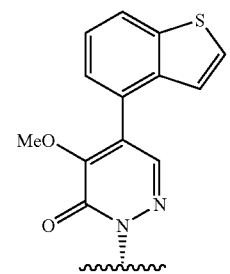 | 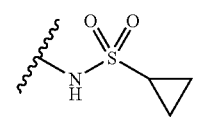 |

TABLE 1-continued (III)

| Example # | A | Q | G |
|---|---|---|---|
| 53 | tert-butyl ester | 4-(quinolin-4-yl)-5-methoxy-pyridazin-3(2H)-one | cyclopropanesulfonamide |
| 54 | tert-butyl ester | naphtho-furo-pyridazinone | cyclopropanesulfonamide |
| 55 | tert-butyl ester | benzofuro-pyridazinone | cyclopropanesulfonamide |
| 56 | cyclopentyl ester | 4-(naphthalen-1-yl)-5-bromo-pyridazin-3(2H)-one | cyclopropanesulfonamide |

TABLE 1-continued
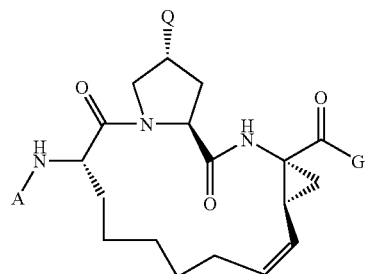
(III)
| Example # | A | Q | G |
|---|---|---|---|
| 57 | 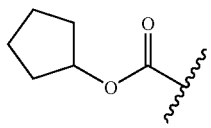 | 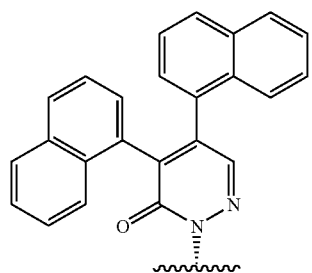 | 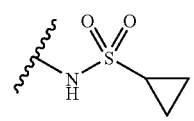 |
| 58 | 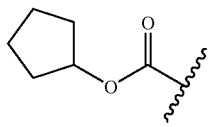 | 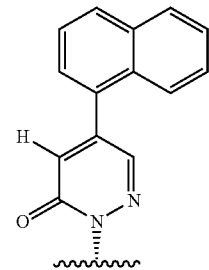 | 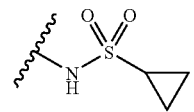 |
| 59 | 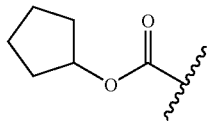 | 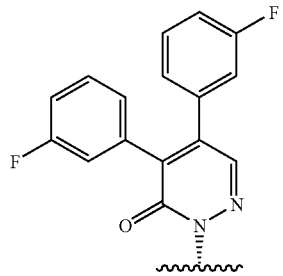 | 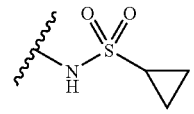 |
| 60 | 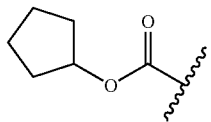 | 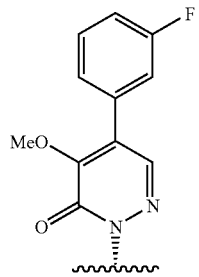 | 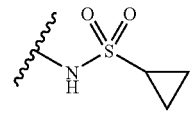 |

TABLE 1-continued (III)

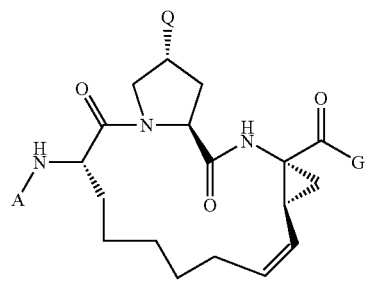

| Example # | A | Q | G |
|---|---|---|---|
| 61 | cyclopentyl ester | 5H-pyridazino-indol-4(3H)-one | cyclopropanesulfonamide |
| 62 | cyclopentyl ester | 4-(5-fluoronaphthalen-1-yl)-5-methoxypyridazin-3(2H)-one | cyclopropanesulfonamide |
| 63 | cyclopentyl ester | 5-methoxy-4-(quinoxalin-5-yl)pyridazin-3(2H)-one | cyclopropanesulfonamide |
| 64 | cyclopentyl ester | 4-(benzofuran-4-yl)-5-methoxypyridazin-3(2H)-one | cyclopropanesulfonamide |

TABLE 1-continued
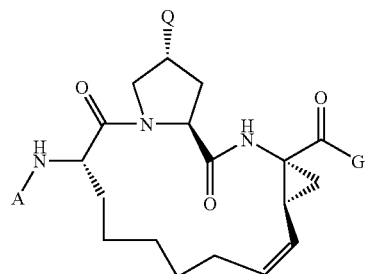
(III)
| Example # | A | Q | G |
|---|---|---|---|
| 65 | 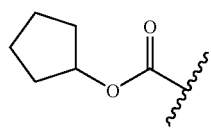 | 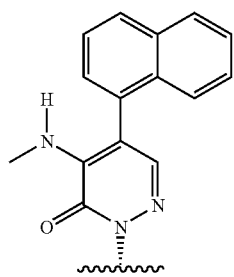 | 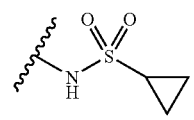 |
| 66 | 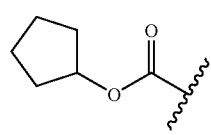 | 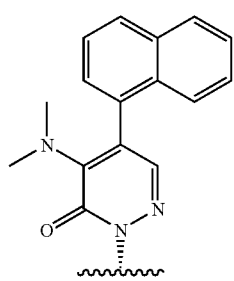 | 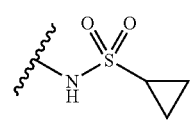 |
| 67 | 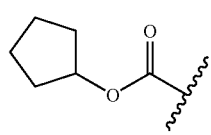 | 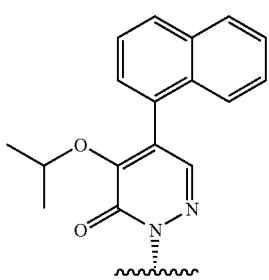 | 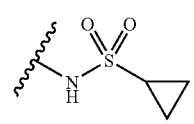 |
| 68 | 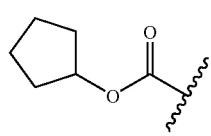 | 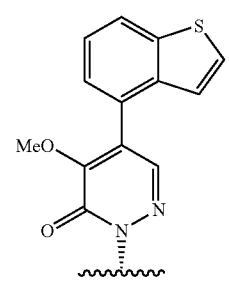 | 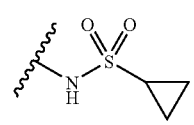 |

TABLE 1-continued (III)

| Example # | A | Q | G |
|---|---|---|---|
| 69 | cyclopentyl ester | 4-(quinolin-4-yl)-5-methoxy-pyridazin-3(2H)-one | N-cyclopropylsulfonamide |
| 70 | cyclopentyl ester | naphtho-furo-pyridazinone | N-cyclopropylsulfonamide |
| 71 | 2-thienyl ketone | 4-bromo-5-(naphthalen-1-yl)pyridazin-3(2H)-one | N-cyclopropylsulfonamide |
| 72 | 2-thienyl ketone | 4,5-di(naphthalen-1-yl)pyridazin-3(2H)-one | N-cyclopropylsulfonamide |

TABLE 1-continued
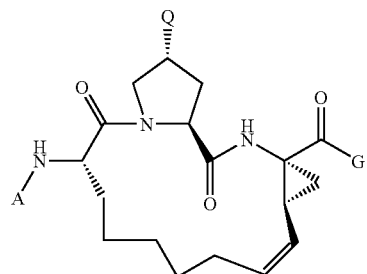
(III)
| Example # | A | Q | G |
|---|---|---|---|
| 73 | 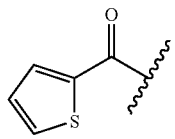 | 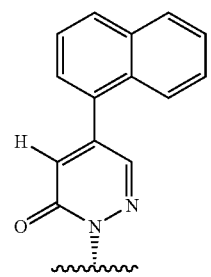 | 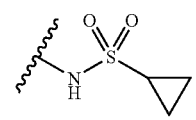 |
| 74 | 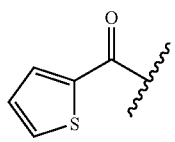 | 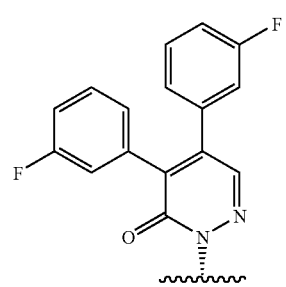 | 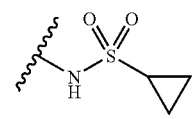 |
| 75 | 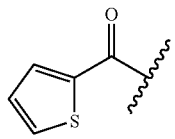 | 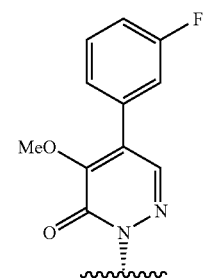 | 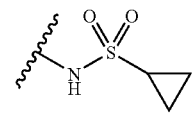 |
| 76 | 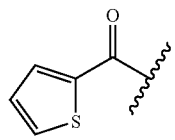 | 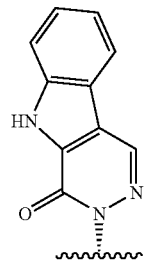 | 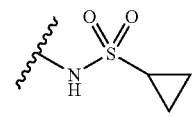 |

TABLE 1-continued
(III)
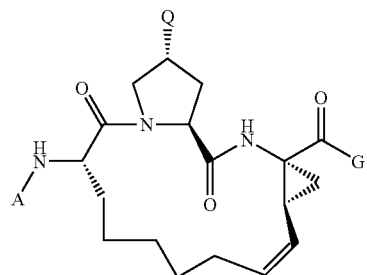
| Example # | A | Q | G |
|---|---|---|---|
| 77 | 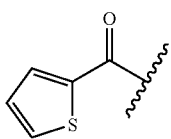 | 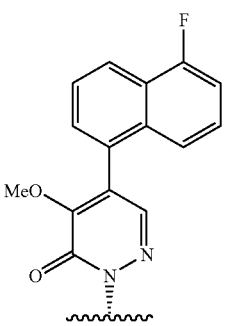 | 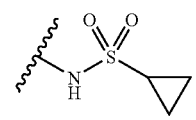 |
| 78 | 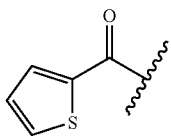 | 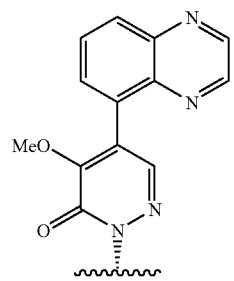 | 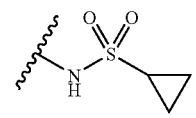 |
| 79 | 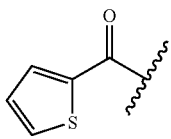 | 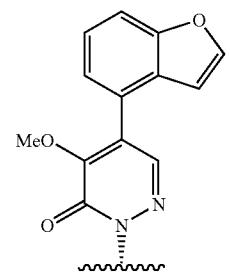 | 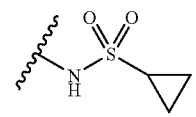 |
| 80 | 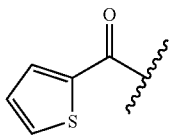 | 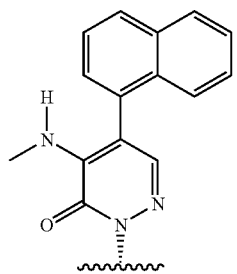 | 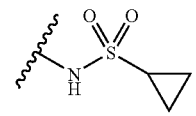 |

TABLE 1-continued
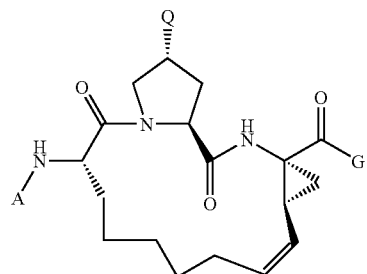
(III)
| Example # | A | Q | G |
|---|---|---|---|
| 81 | 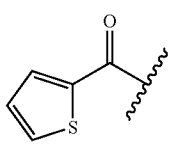 | 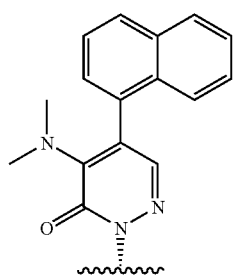 | 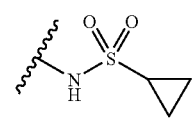 |
| 82 | 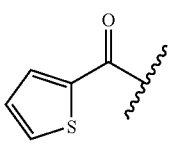 | 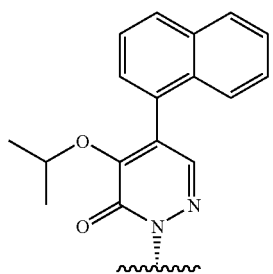 | 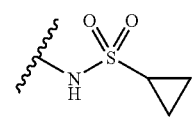 |
| 83 | 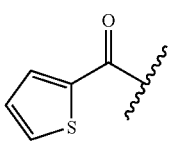 | 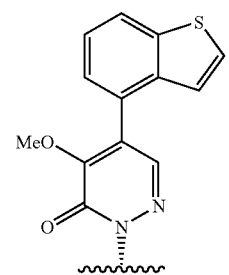 | 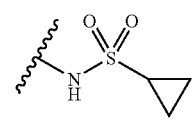 |
| 84 | 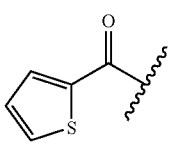 | 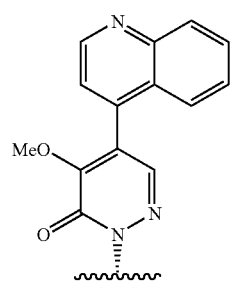 | 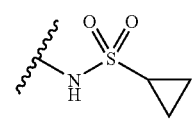 |

TABLE 1-continued
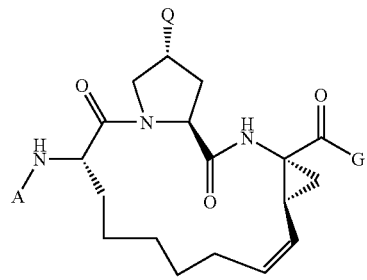
(III)
| Example # | A | Q | G |
|---|---|---|---|
| 85 | 2-thienyl-C(O)- | naphtho-furo-pyridazinone (N-linked) | -NHS(O)₂-cyclopropyl |
| 86 | cyclobutyl-O-C(O)- | 4-(1-naphthyl)-5-bromo-pyridazin-3(2H)-one (N-linked) | -NHS(O)₂-cyclopropyl |
| 87 | cyclobutyl-O-C(O)- | 4,5-di(1-naphthyl)-pyridazin-3(2H)-one (N-linked) | -NHS(O)₂-cyclopropyl |
| 88 | cyclobutyl-O-C(O)- | 5-(1-naphthyl)-pyridazin-3(2H)-one (N-linked) | -NHS(O)₂-cyclopropyl |

TABLE 1-continued
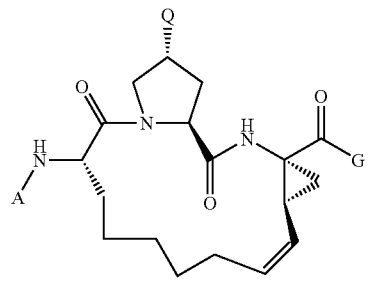
(III)
| Example # | A | Q | G |
|---|---|---|---|
| 89 | cyclobutyl ester | 4,5-bis(3-fluorophenyl)pyridazin-3(2H)-one | cyclopropylsulfonamide |
| 90 | cyclobutyl ester | 5-(3-fluorophenyl)-4-methoxypyridazin-3(2H)-one | cyclopropylsulfonamide |
| 91 | cyclobutyl ester | 5H-pyridazino[4,5-b]indol-1(2H)-one | cyclopropylsulfonamide |
| 92 | cyclobutyl ester | 5-(5-fluoronaphthalen-1-yl)-4-methoxypyridazin-3(2H)-one | cyclopropylsulfonamide |

TABLE 1-continued
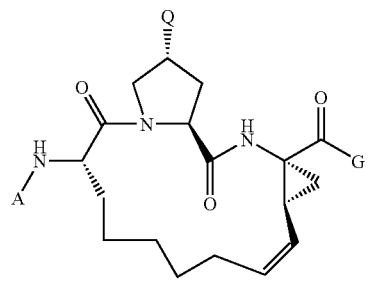
(III)
| Example # | A | Q | G |
|---|---|---|---|
| 93 | 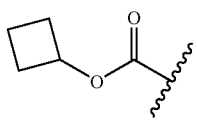 | 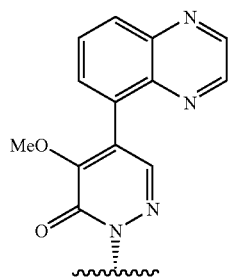 | 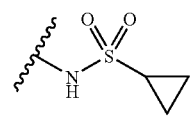 |
| 94 | 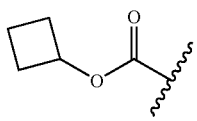 | 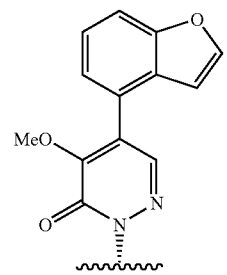 | 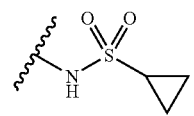 |
| 95 | 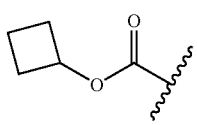 | 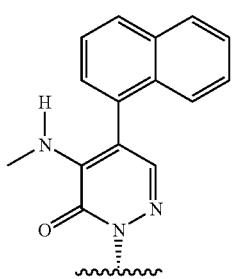 | 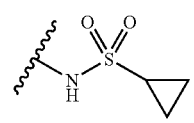 |
| 96 | 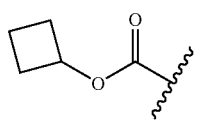 | 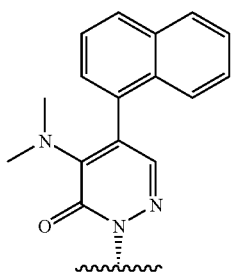 | 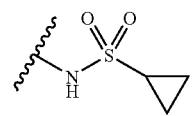 |

TABLE 1-continued
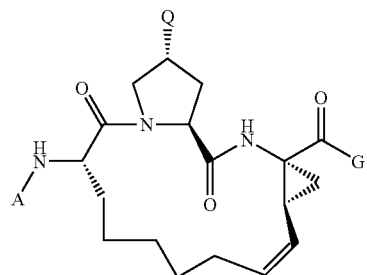
(III)
| Example # | A | Q | G |
|---|---|---|---|
| 97 | cyclobutyl ester | 4-(naphthalen-1-yl)-5-isopropoxy-pyridazin-3(2H)-one | cyclopropylsulfonamide |
| 98 | cyclobutyl ester | 4-(benzothiophen-4-yl)-5-methoxy-pyridazin-3(2H)-one | cyclopropylsulfonamide |
| 99 | cyclobutyl ester | 4-(quinolin-4-yl)-5-methoxy-pyridazin-3(2H)-one | cyclopropylsulfonamide |
| 100 | cyclobutyl ester | naphtho-furo-pyridazinone | cyclopropylsulfonamide |

In one embodiment, the present invention features pharmaceutical compositions comprising a compound of the present invention, or a pharmaceutically acceptable salt, ester or prodrug thereof.

A further embodiment of the present invention includes pharmaceutical compositions comprising a compound of the present invention, or a pharmaceutically acceptable salt, ester, or prodrug thereof, with a pharmaceutically acceptable carrier or excipient.

Yet another embodiment of the present invention is a pharmaceutical composition comprising a combination of two or more compounds of the present invention, or a pharmaceutically acceptable salt, ester, or prodrug thereof, with a pharmaceutically acceptable carrier or excipient.

In another embodiment, the pharmaceutical compositions of the present invention may further contain other anti-HCV agents. Examples of anti-HCV agents include, but are not limited to, interferon (e.g., alpha-interferon, beta-interferon, consensus interferon, pegylated interferon, or albumin or other conjugated interferon), ribavirin, and amantadine. For further details see S. Tan Pause, Y. Shi, N. Sonenberg, Hepatitis C Therapeutics: Current Status and Emerging Strategies, Nature Rev. Drug Discov., 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002) which are herein incorporated by reference in their entirety. In another embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the pharmaceutical compositions of the present invention may further comprise another anti-viral, anti-bacterial, anti-fungal or anti-cancer agent, or an immune modulator, or another therapeutic agent.

According to another embodiment, the present invention includes methods of treating hepatitis C infections in a subject in need of such treatment by administering to said subject a therapeutically effective amount or an anti-HCV virally effective amount of a compound of the present invention, or a pharmaceutically acceptable salt, ester or prodrug thereof. The methods can further include administration of an additional therapeutic agent, including another antiviral agent or another anti-HCV agent, such as those described above. The additional agent can be co-administered, concurrently administered or sequentially administered with a compound (a pharmaceutically acceptable salt, ester or prodrug thereof) or a pharmaceutical composition of the present invention. The methods herein can further include the step of identifying that the subject is in need of treatment for hepatitis C infection. The identification can be by subjective (e.g., health care provider determination) or objective (e.g., diagnostic test) means.

According to a further embodiment, the present invention includes methods of treating hepatitis C infections in a subject in need of such treatment by administering to said subject an anti-HCV virally effective amount or an inhibitory amount of the pharmaceutical compositions of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The terms "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The terms "$C_2$-$C_6$ alkenyl," or "$C_2$-$C_8$ alkenyl," as used herein, denote a monovalent group derived from a hydrocarbon moiety by the removal of a single hydrogen atom wherein the hydrocarbon moiety has at least one carbon-carbon double bond and contains from two to six, or two to eight carbon atoms, respectively. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety by the removal of a single hydrogen atom wherein the hydrocarbon moiety has at least one carbon-carbon triple bond and contains from two to six, or two to eight carbon atoms, respectively. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom where the saturated carbocyclic ring compound has from 3 to 8, or from 3 to 12, ring atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom where the carbocyclic ring compound has from 3 to 8, or from 3 to 12, ring atoms, respectively. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The terms "heterocyclic" and "heterocycloalkyl," can be used interchangeably and referred to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted" as used herein, refers to independent replacement of one, two, or three or more of the hydrogen atoms thereon with substituents including, but not limited to, —F, —Cl, —Br, —I, —OH, protected hydroxy, —$NO_2$, —CN, —$NH_2$, protected amino, —NH—$C_1$-$C_2$-alkyl, —NH—$C_2$-$C_{12}$-alkenyl, —NH —$C_2$-$C_{12}$-alkenyl, —NH —$C_3$-$C_{12}$-cycloalkyl, —NH -aryl, —NH -heteroaryl, —NH -heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)— $C_1$-$C_{12}$-alkyl, —C(O)— $C_2$-$C_{12}$-alkenyl, —C(O)— $C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH— $C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$— $C_1$-$C_{12}$-alkyl, —$OCO_2$— $C_2$-$C_{12}$-alkenyl, —$OCO_2$— $C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH— $C_1$-$C_{12}$-alkyl, —OCONH— $C_2$-$C_{12}$-alkenyl, —OCONH— $C_2$-$C_{12}$-alkenyl, —OCONH— $C_3$-$C_{12}$-cycloalkyl, —OCONH-aryl, —OCONH-heteroaryl, —OCONH-heterocycloalkyl, —NHC(O)— $C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$— $C_1$-$C_{12}$-alkyl, —$NHCO_2$— $C_2$-$C_{12}$-alkenyl, —$NHCO_2$— $C_2$-$C_{12}$-alkenyl, —$NHCO_2$— $C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH— $C_1$-$C_{12}$-alkyl, —NHC(O)NH— $C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH— $C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH— $C_1$-$C_{12}$-alkyl, —NHC(NH)NH— $C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH— $C_2$-$C_{12}$-alkenyl, —$SO_2$NH—$C_2$-$C_{12}$-alkenyl, —$SO_2$NH— $C_3$-$C_{12}$-cycloalkyl, —$SO_2$NH— aryl, —$SO_2$NH— heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloalkylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as D- or L- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8: 1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The terms "protogenic organic solvent," or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high-performance liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof, or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms. An additional method of the present invention is the treatment of biological samples with an inhibitory amount of a compound of the present invention in such amounts and for such time as is necessary to inhibit viral replication and/or reduce viral load. The term "inhibitory amount" means a sufficient amount to inhibit viral replication and/or decrease the hepatitis C viral load in a biological sample. The term "biological sample(s)" as used herein means a substance of biological origin intended for administration to a subject. Examples of biological samples include, but are not limited to blood and components thereof such as plasma, platelets, subpopulations of blood cells and the like; organs such as kidney, liver, heart, lung, and the like; sperm and ova; bone marrow and components thereof, or stem cells. Thus another embodiment of the present invention is a method of treating a biological sample by contacting said biological sample with an inhibitory amount of a compound or pharmaceutical composition of the present invention.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations used in the descriptions of the schemes and the examples that follow are:

aq. for aqueous;
Ac for acetyl;
Boc for tert-butoxycarbonyl;
Bz for benzoyl;
Bn for benzyl;
CDI for carbonyldiimidazole;
dba for dibenzylidene acetone;
CDI for 1,1'-carbonyldiimidizole;
DBU for 1,8-diazabicyclo[5.4.0]undec-7-ene;
DCM for dichloromethane;
DIAD for diisopropylazodicarboxylate;
DMAP for dimethylaminopyridine;
DMF for dimethyl formamide;
DMSO for dimethyl sulfoxide;
dppb for diphenylphosphino butane;
EtOAc for ethyl acetate;
HATU for 2-(7-Aza-1H-benzotriazole-1-yl)-1,1,3,3-tetramethyluronium hexafluorophosphate;
iPrOH for isopropanol;
NaHMDS for sodium bis(trimethylsilyl)amide;
NMO for N-methylmorpholine N-oxide;
MeOH for methanol;
Ph for phenyl;
POPd for dihydrogen dichlorobis(di-tert-butylphosphino) palladium(II);
TBAHS for tetrabutyl ammonium hydrogen sulfate;
TEA for triethylamine;
THF for tetrahydrofuran;
TPP for triphenylphosphine;
Tris for Tris(hydroxymethyl)aminomethane;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DCM for dichloromethane;
DIBAL-H for diisobutylaluminum hydride;
DIEA for diisopropyl ethylamine;
DME for ethylene glycol dimethyl ether;
DMEM for Dulbecco's Modified Eagles Media;
EDANS for 5-(2-Amino-ethylamino)-naphthalene-1-sulfonic acid;
EDCI or EDC;
DMF for N,N-dimethyl formamide;
ESI for electrospray ionization;
Et for ethyl;
for 1-(3-diethylaminopropyl)-3-ethylcarbodiimide hydrochloride;
Hoveyda's Cat. for Dichloro(o-isopropoxyphenylmethylene) (tricyclohexylphosphine)ruthenium(II);
KHMDS is potassium bis(trimethylsilyl)amide;
Ms for mesyl;
EtOAc for ethyl acetate;
g for gram(s);
h for hour(s);
PyBrOP for Bromo-tri-pyrolidino-phosphonium hexafluorophosphate;
RCM for ring-closing metathesis;
RT for room temperature;
HATU for O-(7-Azabenzotriazole-1-yl)-N,N,N',N'-tetramethyluronium hexafluoro-phosphate;
HPLC for high-performance liquid chromatography;
Ph for phenyl;
Me for methyl;
TEA for triethyl amine;
TFA for trifluoroacetic acid;
MeOH for methanol;
mg for milligram(s);
min for minute(s);
MS for mass spectrometry;
NMR for nuclear magnetic resonance;
rt for room temperature;
THF for tetrahydrofuran;
TLC for thin layer chromatography;
PPh$_3$ for triphenylphosphine;
tBOC or Boc for tert-butyloxy carbonyl.

Synthetic Methods

The compounds and processes of the present invention will be better understood in connection with the following synthetic schemes that illustrate the methods by which the compounds of the invention may be prepared.

Scheme 1
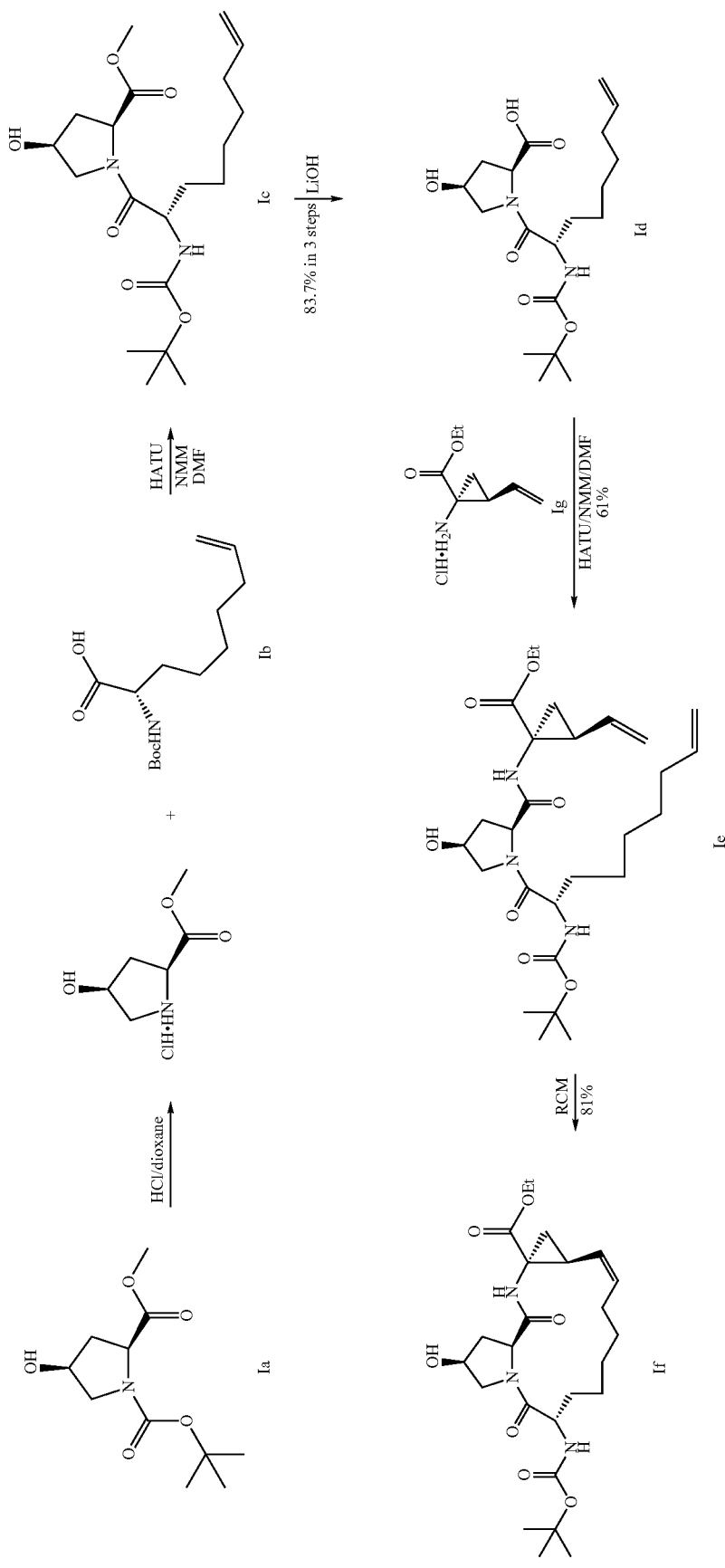

All of the pyridazinone analogs were prepared from the common intermediate If. The synthesis of compound If is outlined in Scheme 1. Commercially available Boc-hydroxyproline Ia was deprotected with HCl (4M) in dioxane, then further coupled with acid Ib using HATU to afford intermediate Ic. Hydrolysis of Ic with LiOH followed by another peptide coupling with cyclopropyl amine Ig yielded the tripeptide Ie. Finally, ring-closing metathesis with Hoveyda-Grubbs' 1$^{st}$ generation catalyst gave the desired key intermediate If.

The carboxylic acid-derived pyridazinone analogs used in the present invention were prepared via several different synthetic routes. The simplest method, shown in Scheme 2, was to condense commercially available pyridazinones (IIa-1-IIa-4) with key intermediate If by using Mitsunobu conditions followed by hydrolysis with LiOH. For further details on the Mitsunobu reaction see O. Mitsunobu, *Synthesis* 1981, 1-28; D. L. Hughes, *Org. React.* 29, 1-162 (1983); D. L. Hughes, *Organic Preparations and Procedures Int.* 28, 127-164 (1996); and J. A. Dodge, S. A. Jones, *Recent Res. Dev. Org. Chem.* 1, 273-283 (1997).

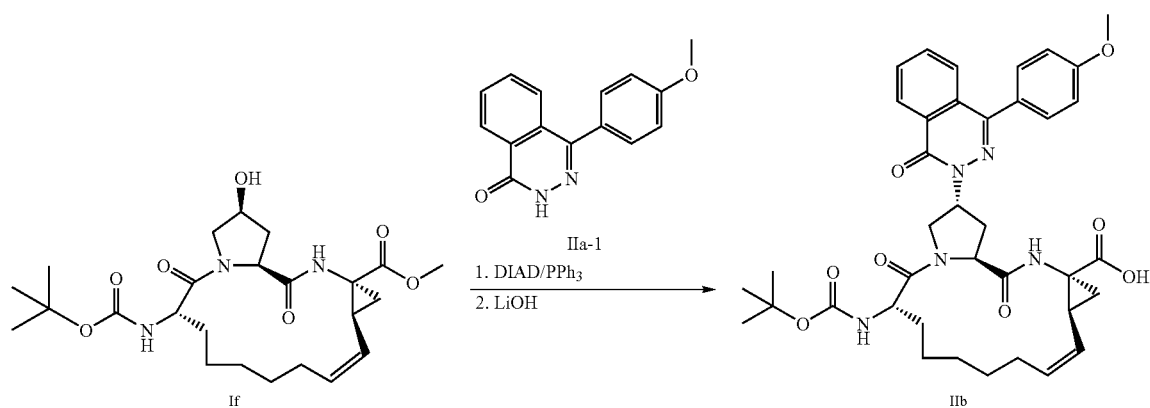

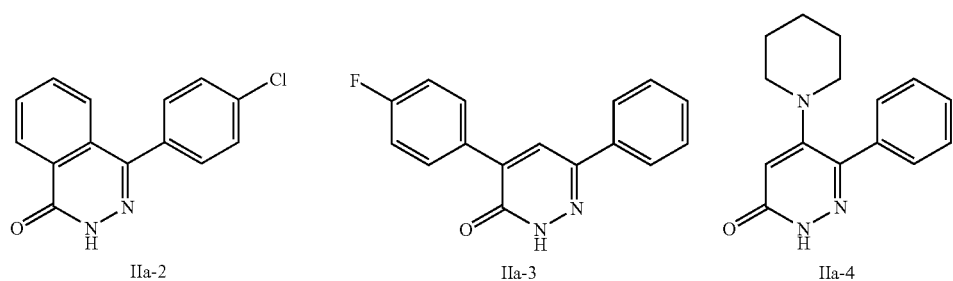

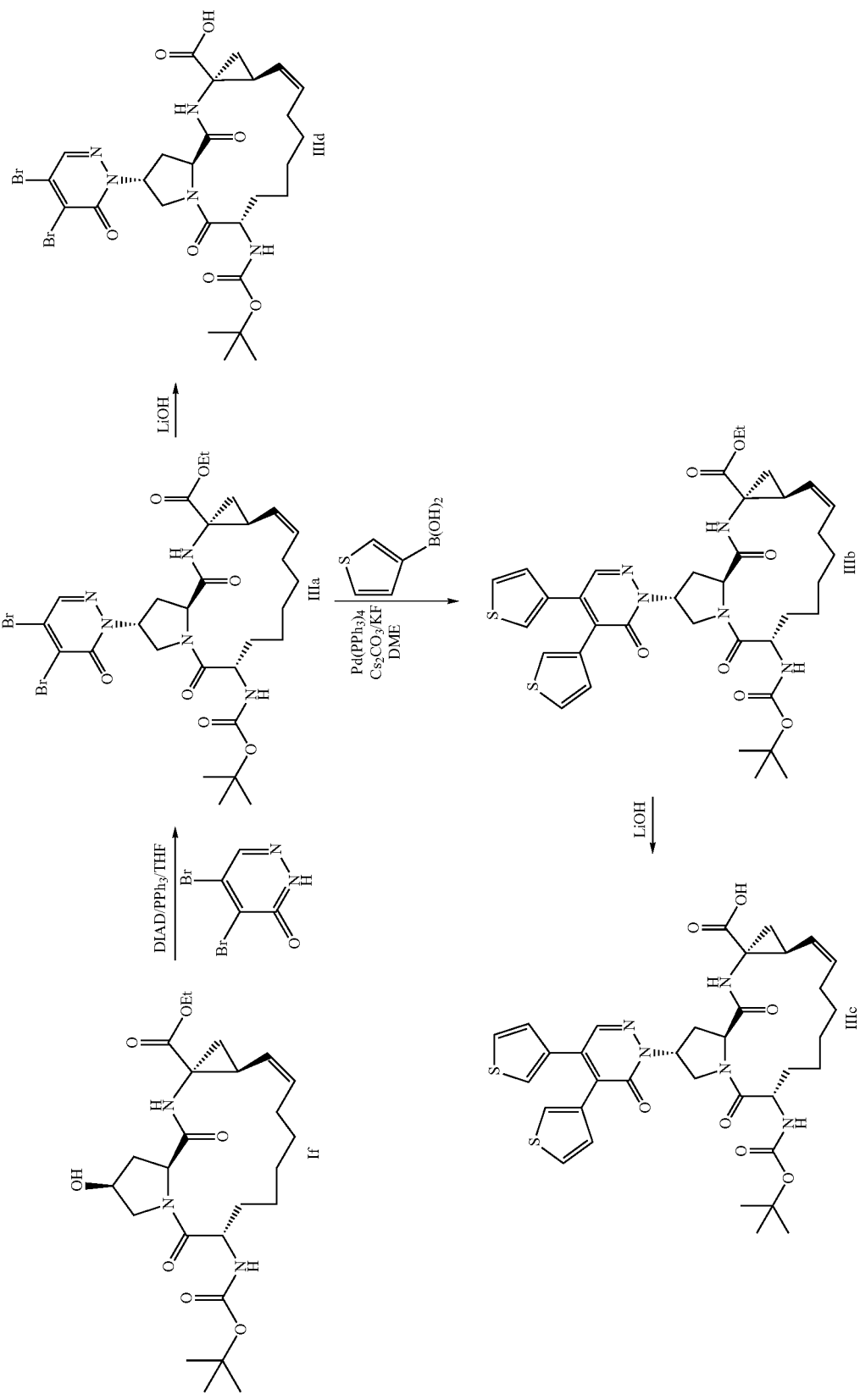
Scheme 3

The second method of preparing pyridazinone analogs of the present invention was to synthetically manipulate di-bromo intermediate IIIa (Scheme 3). Standard Mitsunobu coupling of the commercially available 4,5-dibromopyridazinone with hydroxyl If afforded the desired macrocycle IIIa. Coupling of IIIa with excess boronic acids (for example 3-thiophene boronic acid), cesium carbonate and potassium fluoride furnished di-thiophene IIIb. Hydrolysis of compound compounds IIIa and IIIb with LiOH gave the desired analogs IIId and IIIc respectively. A variety of boronic acids were used in a similar manner to yield an array of di-substituted pyridazinonyl macrocycles.

Differentiation of the bromides on macrocyclic IIIa was achieved via Michael addition. As shown in Scheme 4, commercially available pyrrolidine or methoxide was added to di-bromide IIIa to give compound IVa in typically better than 85% yield. The bromide moiety α to the carbonyl could then undergo a Suzuki coupling with a variety of boronic acids (for example, 3-thiophene boronic acid) to produce intermediate IVb, which was further treated with LiOH to afford analog IVc. For further details concerning the Suzuki coupling reaction see A. Suzuki, *Pure Appl. Chem.* 63, 419-422 (1991) and A. R. Martin, Y. Yang, *Acta Chem. Scand.* 47, 221-230 (1993).

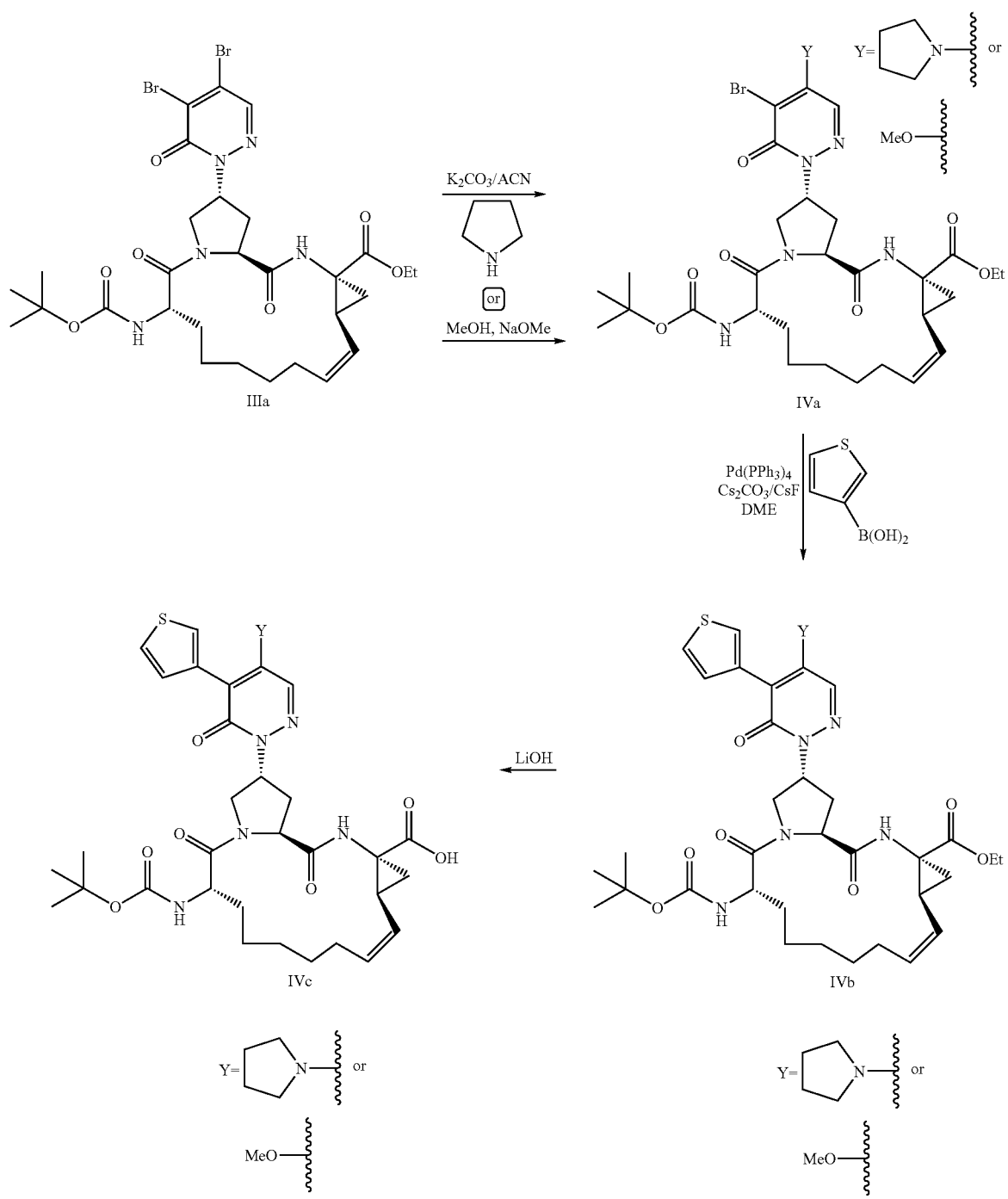

Scheme 5
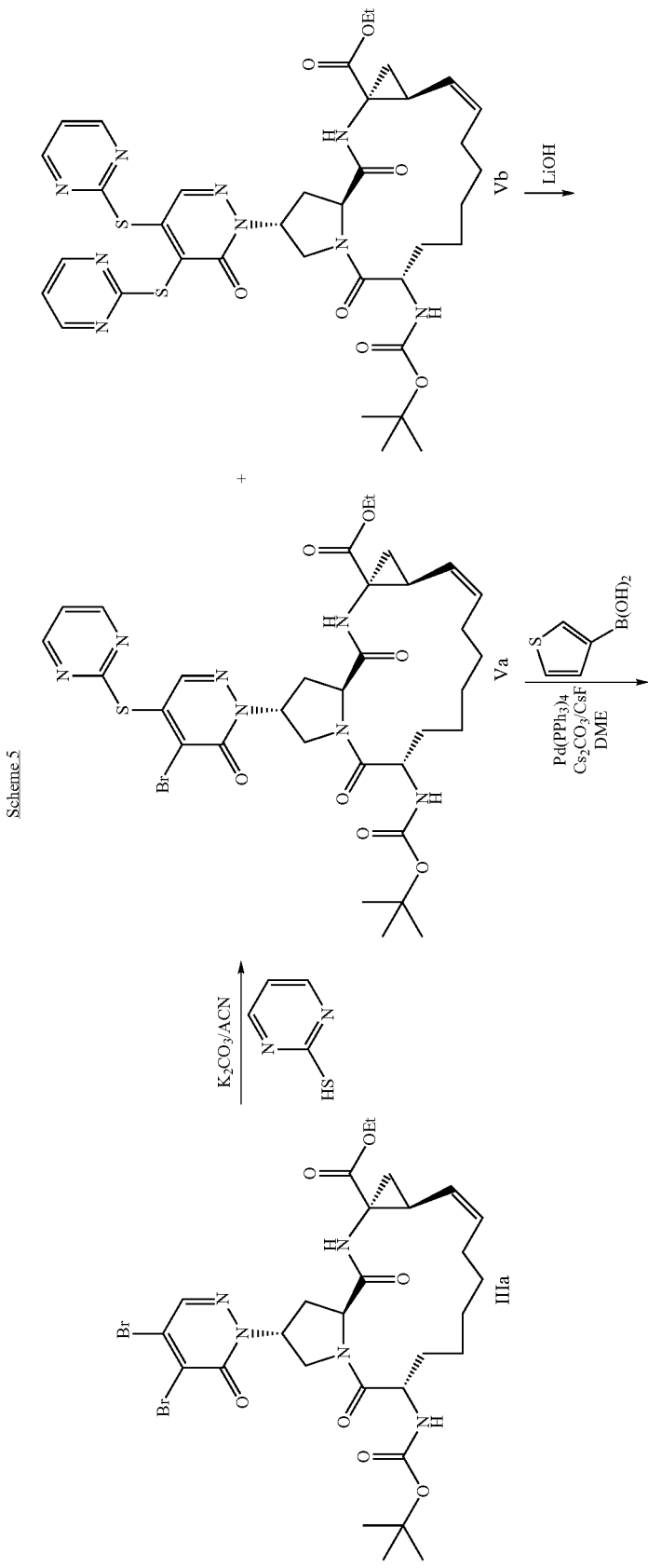

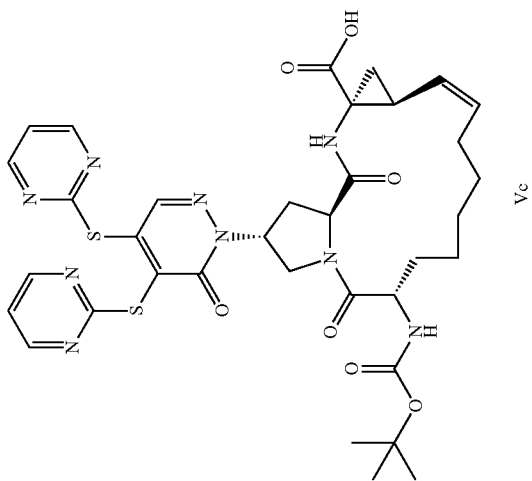
Vc
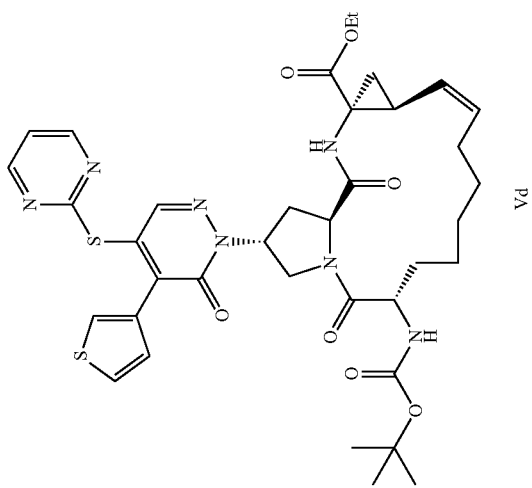
Vd
↓ LiOH
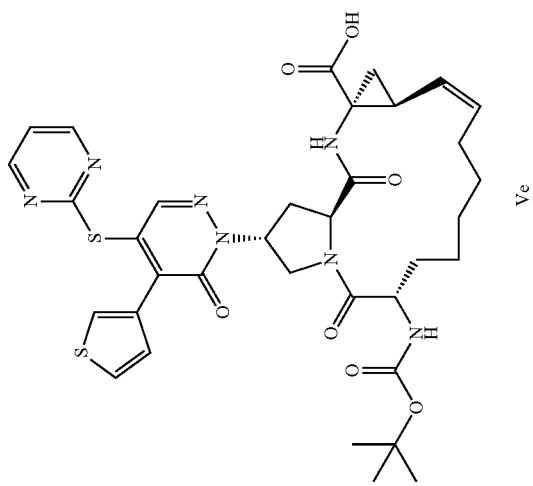
Ve

While the secondary amine and alkoxide nucleophiles gave exclusive Michael-type addition on macrocycle IIIa, sulfur-containing nucleophiles did not exhibit the same selectivity (Scheme 5). Using one equivalent of a sulfur-containing nucleophile, both mono- and bis-addition was observed. The separability of compounds Va, Vb and starting material IIIa by flash column chromatography allowed for a further Suzuki coupling of the mono-alkylated Va with a variety of boronic acids (for example, 3-thiophene boronic acid), which was followed by hydrolysis of Vd with LiOH to furnish analog Ve. The di-alkylated product Vb was also hydrolyzed with LiOH to produce analog Vc.

Scheme 6

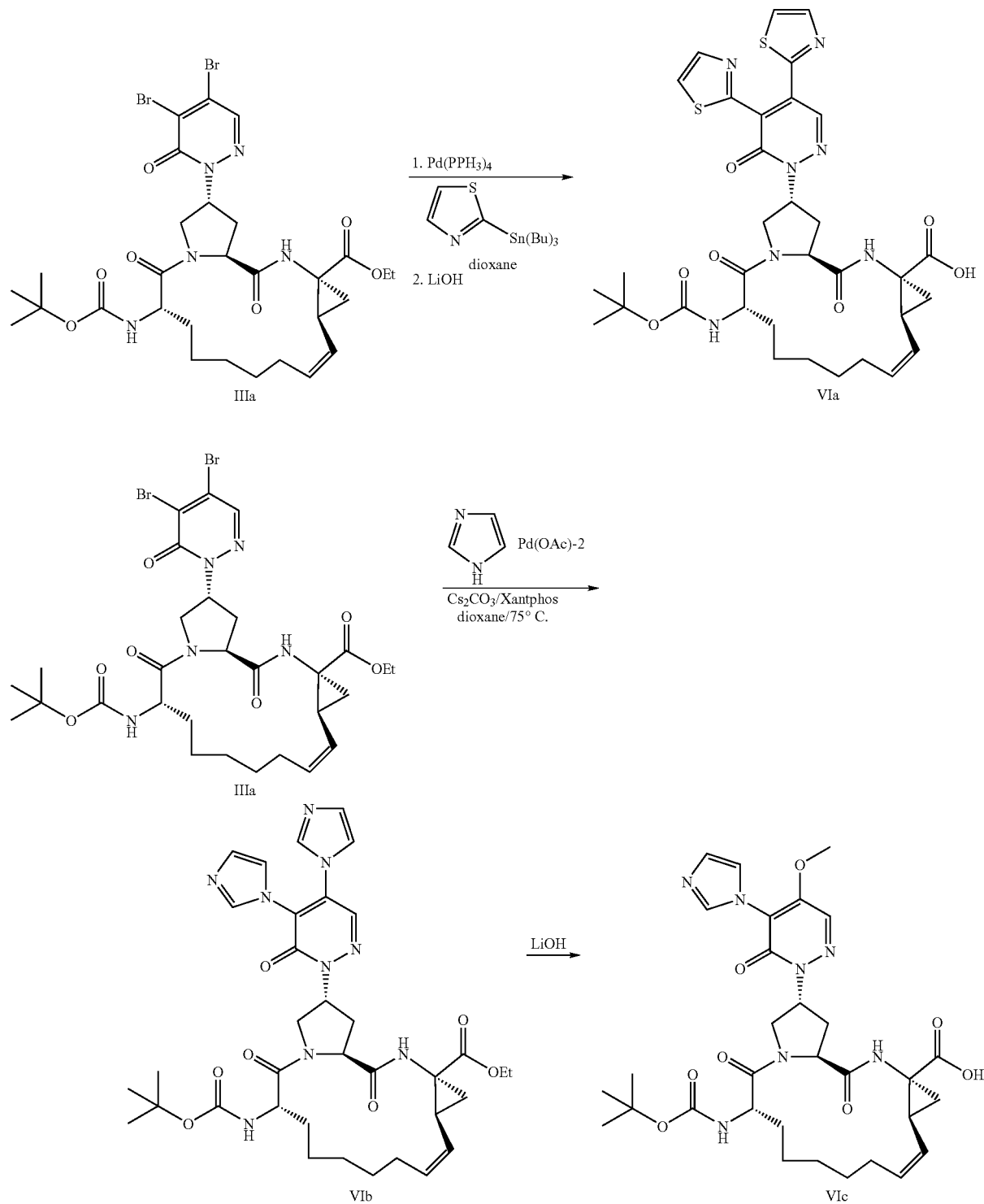

With only a limited number of boronic acids available for Suzuki coupling, other coupling methods such as Stille coupling and N-arylation using Buchwald's chemistry were also explored (Scheme 6). Coupling of intermediate IIIa with 2-stannylthiazole with standard Stille conditions followed by hydrolysis afforded analog VIa. As for N-arylation, coupling of imidazole to di-bromide 6 proceeded smoothly. Unfortunately, hydrolysis with LiOH resulted in the displacement of one of the imidazole moieties with a methoxy group to give VIc. For further details concerning Stille coupling reactions see J. K. Stille, *Angew. Chem. Int. Ed.* 25, 508-524 (1986); M. Pereyre et al., *Tin in Organic Synthesis* (Butterworths, Boston, 1987) pp 185-207 passim., and T. N. Mitchell, *Synthesis* 1992, 803-815. For further details of the Buchwald reaction see J. F. Hartwig, *Angew. Chem. Int. Ed.* 37, 2046-2067 (1998).

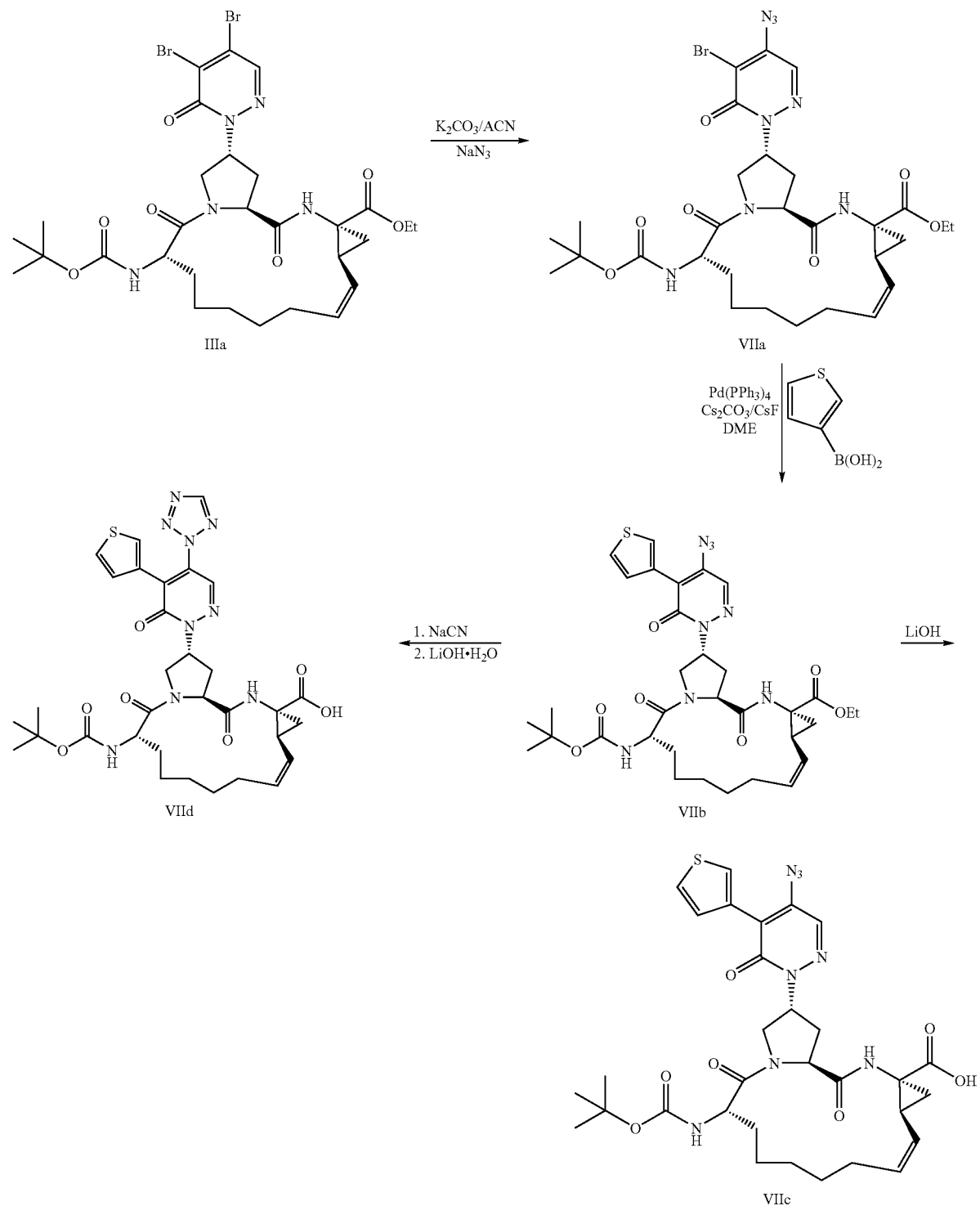

Scheme 7

Another method for the generation of the title pyridazinone analogs is outlined in Scheme 7. Michael addition with sodium azide delivered mono-coupled compound VIIa. Further Suzuki coupling with various boronic acids (for example, 3-thiophene boronic acid) produced azide VIIb. Compound VIIb was hydrolyzed to give analog VIIc. In addition, the azide moiety of compound VIIb was further converted to a tetrazole under standard conditions using sodium cyanide. Subsequent hydrolysis afforded analog VIId.

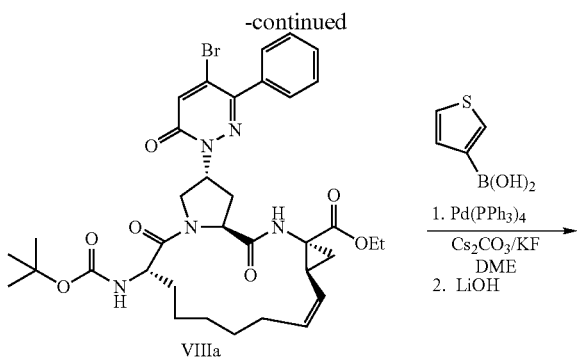

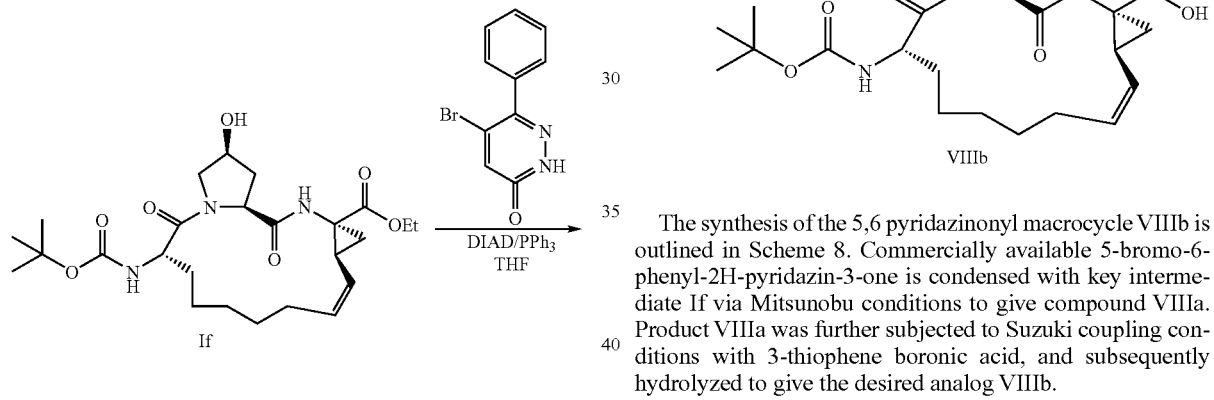

The synthesis of the 5,6 pyridazinonyl macrocycle VIIIb is outlined in Scheme 8. Commercially available 5-bromo-6-phenyl-2H-pyridazin-3-one is condensed with key intermediate If via Mitsunobu conditions to give compound VIIIa. Product VIIIa was further subjected to Suzuki coupling conditions with 3-thiophene boronic acid, and subsequently hydrolyzed to give the desired analog VIIIb.

Scheme 9

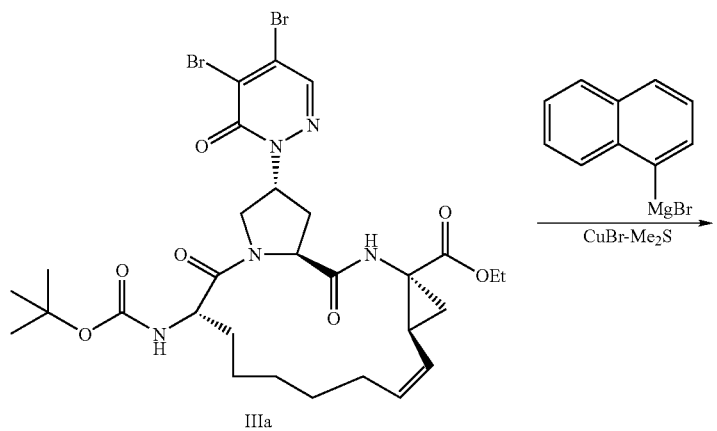

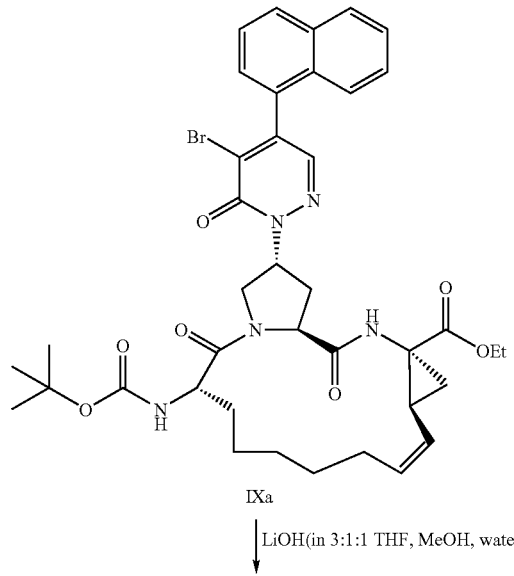
IXa
↓ LiOH(in 3:1:1 THF, MeOH, water)
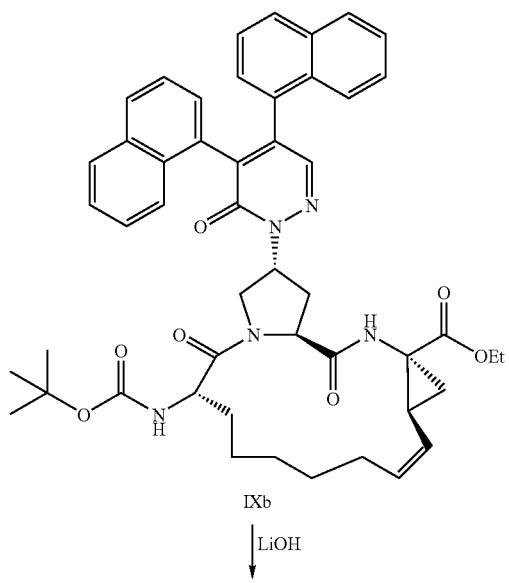
IXb
↓ LiOH
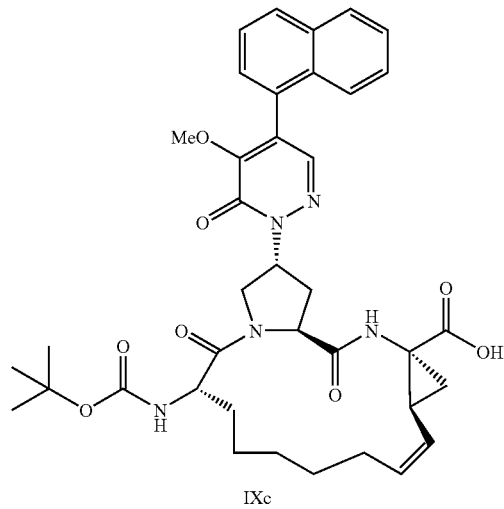
IXc
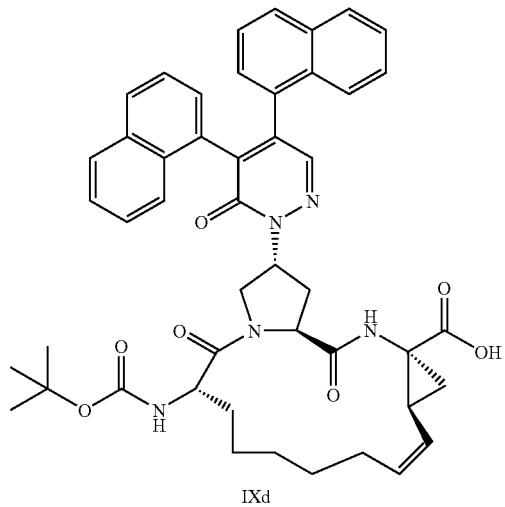
IXd As shown in Scheme 9, carbon-derived nucleophiles could also be incorporated into the bis-bromide framework of IIIa. For example, 1-naphthylmagnesium bromide in the presence of copper bromide-dimethyl sulfide complex generated both the mono- and bis-addition products, IXa and IXb, respectively. When subjected to hydrolysis conditions (using methanol as a co-solvent), acids IXc and IXd were generated.

The sulfonamides Xb were prepared from the corresponding acids Xa by subjecting the acid to a coupling reagent (i.e. CDI, HATU, DCC, EDC and the like) at RT or at elevated temperature, with the subsequent addition of the corresponding sulfonamide $R^3-S(O)_2-NH_2$ (or $R^4R^5-S(O)_2-NH_2$) in the presence of base (wherein X, Y, Z and $R_3$ are as previously defined).

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples (example numbers correlate with numbers within table 1), which are intended as illustrations only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

U.S. Patent Application Publication No. 20050153877 also describes compounds where G=OH, the entire content of which is herein incorporated by reference.

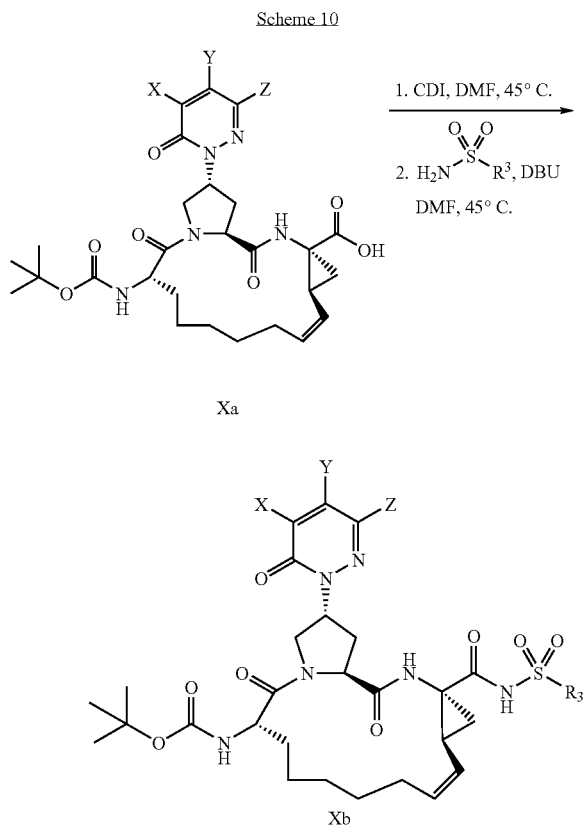

Synthesis of the Tri-peptide Intermediate 1g:

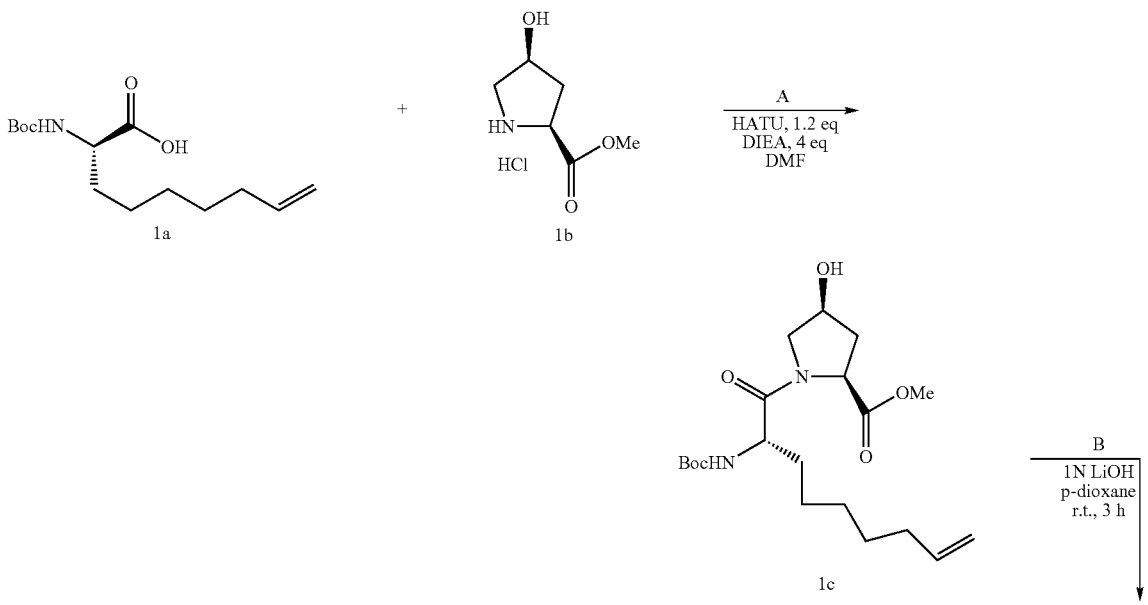

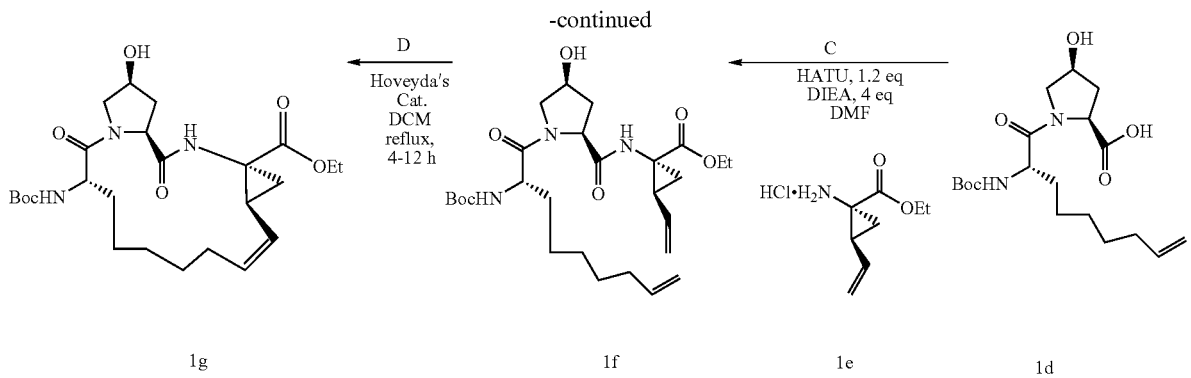

1A. To a solution of Boc-L-2-amino-8-nonenoic acid 1a (1.36 g, 5 mol) and the commercially available cis-L-hydroxyproline methyl ester 1b (1.09 g, 6 mmol) in 15 ml DMF, DIEA (4 ml, 4 eq.) and HATU (4 g, 2 eq) were added. The coupling was carried out at 0° C. over a period of 1 hour. The reaction mixture was diluted with 100 mL EtOAc, and directly washed with 5% citric acid (2×20 ml), water (2×20 ml), 1M NaHCO$_3$ (4×20 ml) and brine (2×10 ml). The organic phase was dried over anhydrous Na$_2$SO$_4$, filtered, and then concentrated in vacuo, affording the dipeptide 1c (1.91 g, 95.8%) that was identified by HPLC (Retention time=8.9 min, 30-70%, 90% B), and MS (found 421.37, M+Na$^+$).

1B. Dipeptide 1c (1.91 g) was dissolved in 15 mL of dioxane and 15 mL of 1 N LiOH aqueous solution, and the resulting mixture was stirred at room temperature for 4 hours. The reaction mixture was acidified by 5% citric acid and extracted with 100 mL EtOAc. The organic portion was then washed with water (2×20 ml), 1M NaHCO$_3$ (2×20 ml) and brine (2×20 ml). The organic phase was dried over anhydrous Na$_2$SO$_4$, filtered, and then concentrated in vacuo, yielding the free carboxylic acid compound 1d (1.79 g, 97%), which was used directly without the need for further purification.

1C. To a solution of the free acid obtained above (1.77, 4.64 mmol) in 5 ml DMF, D-β-vinyl cyclopropane amino acid ethyl ester 1e (0.95 g, 5 mmol), DIEA (4 ml, 4 eq.) and HATU (4 g, 2 eq) were added. The coupling was carried out at 0° C. over a period of 5 hours. The reaction mixture was diluted with 80 mL EtOAc, and washed with 5% citric acid (2×20 ml), water (2×20 ml), 1M NaHCO$_3$ (4×20 ml), and brine (2×10 ml). The organic phase was dried over anhydrous Na$_2$SO$_4$, filtered, and then concentrated in vacuo. The residue was purified by silica gel flash chromatography using gradient elution with hexanes:EtOAc (5:1→3:1→1:1→1:2→1:5). The linear tripeptide 1f was isolated as an oil (1.59 g, 65.4%) and identified by HPLC (Retention time=11.43 min) and MS (found 544.84, M+Na$^+$).

1D. Ring Closing Metathesis (RCM). A solution of the linear tripeptide 1f (1.51 g, 2.89 mmol) in 200 ml dry DCM was deoxygenated by N$_2$ bubbling. Hoveyda's 1$^{st}$ generation catalyst (5 mol % eq.) was then added as a solid. The reaction was refluxed under N$_2$ atmosphere for 12 hours. The solvent was evaporated and the residue was purified by silica gel flash chromatography using gradient elution with hexanes:EtOAc (9:1→5:1→3:1→1:1→1:2→1:5). The cyclic peptide precursor 1g was isolated as a white powder (1.24 g, 87%), and identified by HPLC (Retention time=7.84 min, 30-70%, 90% B), and MS (found 516.28, M+Na$^+$). For further details of the synthetic methods employed to produce the cyclic peptide precursor 1g, see WO 00/059929 (2000).

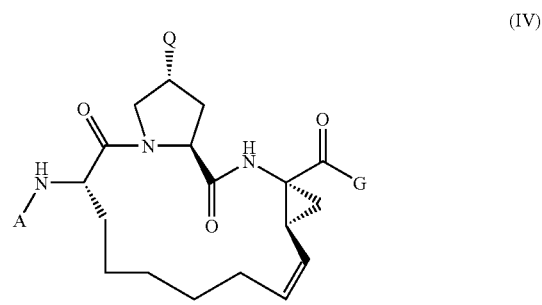

Example 1

Compound of Formula IV, wherein

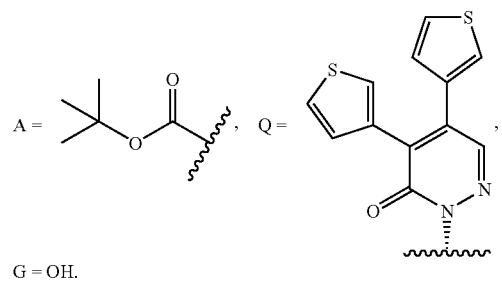

G = OH.

Step 1E (Continuing from Macrocycle 1g, Vida Supra)

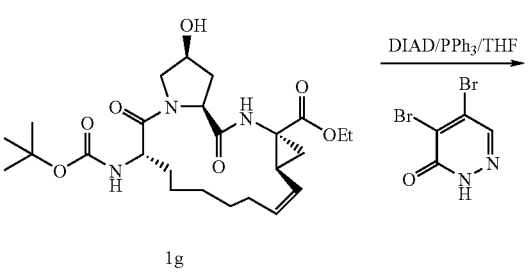

1g

-continued

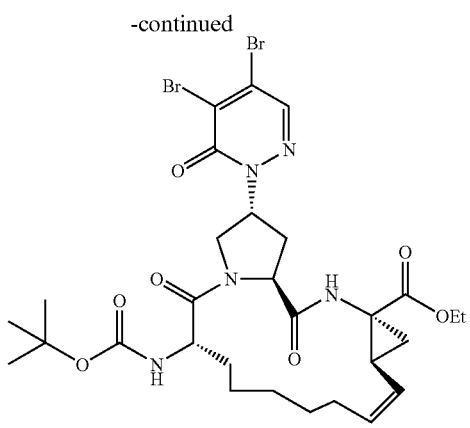

To a mixture of macrocyclic compound 1g (185 mg, 0.38 mmol), 4,5-dibromo-2H-pyridazin-3-one (95 mg, 0.38 mmol) and triphenylphosphine (197 mg, 0.75 mmol) in THF (5 mL) is added DIAD (148 μL, 0.75 mmol) dropwise at 0° C. After stirring at 0° C. for 15 min., the solution was warmed to room temperature and is further stirred for 16 hours. The mixture was then concentrated in vacuo and the residue is purified by column chromatography eluting with 40% ethyl acetate-hexane to give 235 mg (86%) compound 1h.

$^1$H-NMR (500 MHz, CDCl$_3$) δ (ppm): 7.8 (s, 1H), 7.1 (brs, 1H), 5.5 (m, 2H), 5.2 (m, 2H), 5.0 (m, 1H), 4.4 (brt, 1H), 4.0-4.2 (m, 4H), 2.9 (m, 1H), 2.6 (m, 1H), 1.8-2.3 (m, 5H), 1.4 (s, 9H), 1.2 (t, 3H). MS (ESI) m/z=730.6 (M+H)$^+$.

Step 1F.

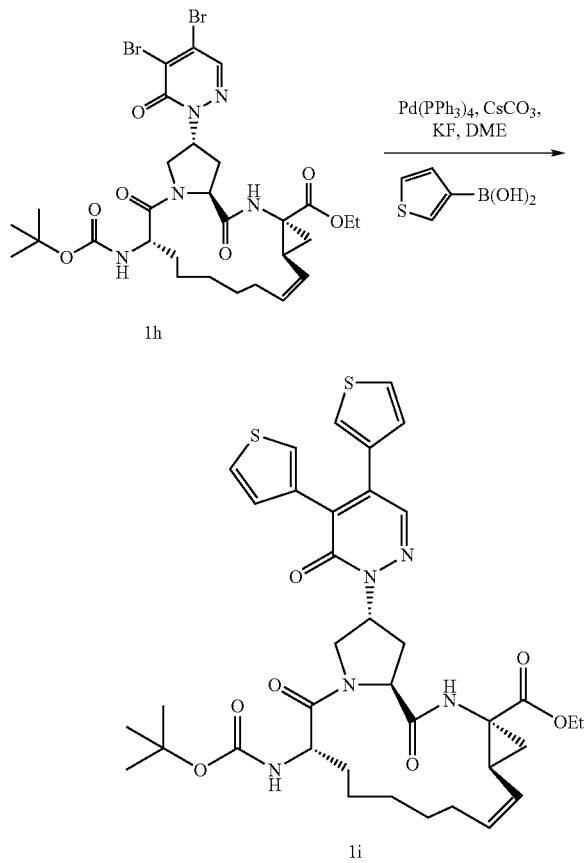

A mixture of compound 1h (40 mg, 0.055 mmol), 3-thiophene boronic acid (35 mg, 0.28 mmol), cesium carbonate (71 mg, 0.22 mmol), potassium fluoride monohydrate (41 mg, 0.44 mmol) was placed in a round bottom flask and was flushed twice with nitrogen. To this mixture was added DME and the resulting solution was flushed again with nitrogen before palladium tetrakis(triphenylphosphine) (7 mg, 10 mol %) was added. After flushing two more times with nitrogen, the mixture was heated to reflux for 20 hours. The mixture was then cooled and then diluted with water and extracted three times with EtOAc. The combined EtOAc layers are washed once with brine, dried (MgSO$_4$), filtered and concentrated in vacuo. The residue was purified by column chromatography eluting with 20-40% EtOAc-hexane to give compound II as a clear film (24 mg, 60%).

$^1$H-NMR (500 MHz, CDCl$_3$) δ (ppm): 7.9 (s, 1H), 7.6 (s, 1H), 7.3 (s, 1H), 7.3 (m, 1H), 7.0 (s, 1H), 6.9 (d, 1H), 6.8 (d, 1H), 5.7 (m, 1H), 5.5 (m, 1H), 5.4 (brd, 1H), 5.2 (t, 1H), 5.0 (m, 1H), 4.6 (brt, 1H), 4.0-4.2 (m, 4H), 2.9 (m, 1H), 2.6 (m, 1H), 2.0-2.3 (m, 5H), 1.4 (s, 9H), 1.2 (t, 3H). MS (ESI) m/z=758.63 (M+Na)$^+$.

Step 1G.

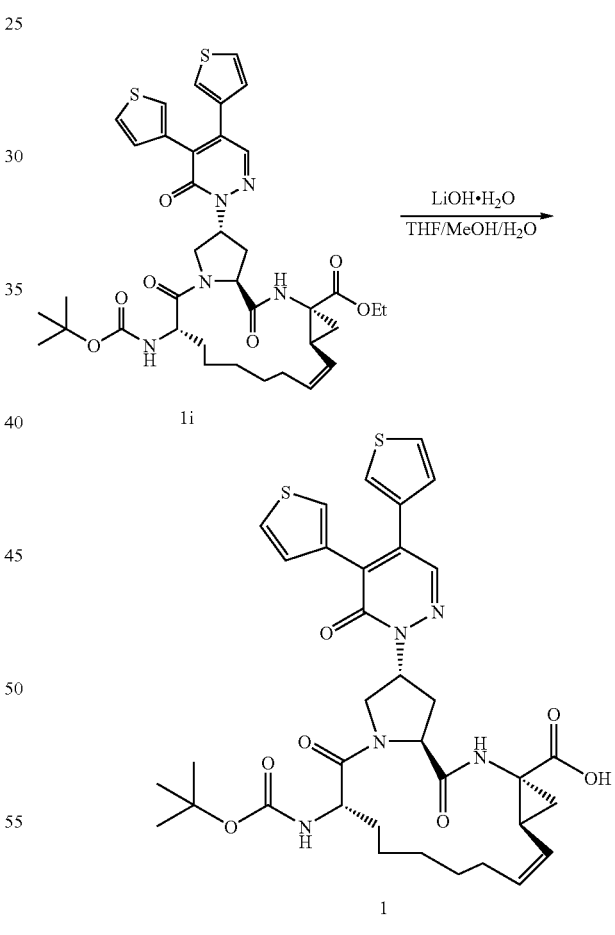

To a solution of compound 1i (24 mg, 0.033 mmol) in THF/MeOH/H$_2$O (2/1/0.5 mL) was added lithium hydroxide (14 mg, 0.33 mmol). After stirring for 16 hours at room temperature, the mixture was acidified to pH 4 with citric acid and extracted three times with EtOAc. The combined organic extracts were washed once with brine, dried (MgSO$_4$), filtered and concentrated in vacuo. The residue was purified by column chromatography eluting with 5-10% methanol-chloroform to give the title compound 1 (13 mg, 56%).

MS (ESI) m/z=708.3 (M+H)⁺.

Example 2

Compound of Formula IV, wherein

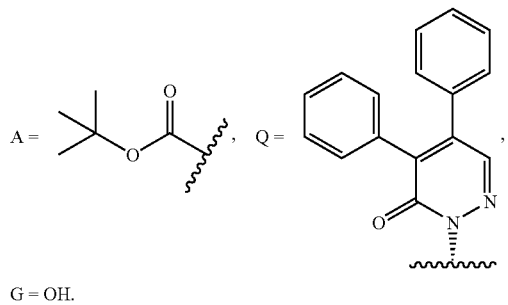

G = OH.

The title compound was prepared by a double Suzuki coupling with phenylboronic acid and compound 1h according to the procedure set forth in step 1F, followed by hydrolysis of the ethyl ester via the method described in step 1G.

MS (ESI) m/z=697.1 (M+H)⁺.

Example 3

Compound of Formula IV, wherein

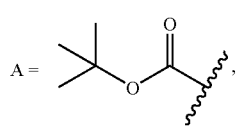

, G = OH.

The title compound was prepared by a double Suzuki coupling with 4-(N,N-dimethylamino)phenyl boronic acid and compound 1h according to the procedure set forth in step 1F, followed by hydrolysis of the ethyl ester via the method described in step 1G.

MS (ESI) m/z=783.2 (M+H)⁺.

Example 4

Compound of Formula IV, wherein

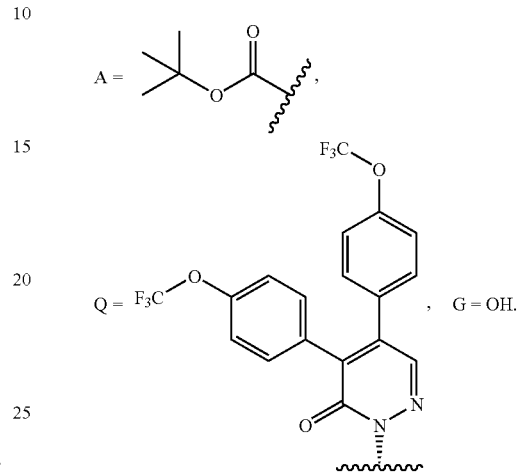

, G = OH.

The title compound was prepared by a double Suzuki coupling with 4-(trifluoromethoxy)phenyl boronic acid and compound 1h according to the procedure set forth in step 1F, followed by hydrolysis of the ethyl ester via the method described in step 1G.

MS (ESI) m/z=865.3 (M+H)⁺.

Example 5

Compound of Formula IV, wherein

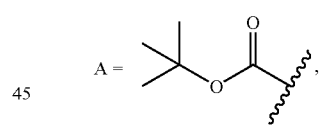

, G = OH.

The title compound was prepared by a double Suzuki coupling with 4-cyanophenyl boronic acid and compound 1h according to the procedure set forth in step 1F, followed by hydrolysis of the ethyl ester via the method described in step 1G.

MS (ESI) m/z=746.1 (M+H)+.

Example 6

Compound of Formula IV, wherein

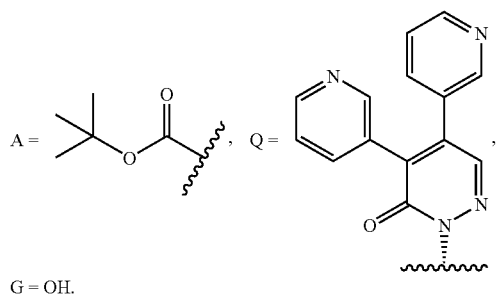

G = OH.

The title compound was prepared by a double Suzuki coupling with 3-pyridyl boronic acid and compound 1h according to the procedure set forth in step 1F, followed by hydrolysis of the ethyl ester via the method described in step 1G.

MS (ESI) m/z=698.3 (M+H)+.

Example 7

Compound of Formula IV, wherein

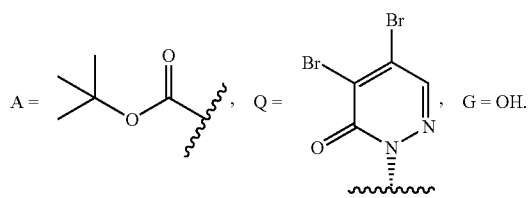

The title compound was prepared by hydrolysis of the ethyl ester in compound 1h via the method described in step 1G.

MS (ESI) m/z=652.2, 654.2 (M+H)+.

Example 8

Compound of Formula IV, wherein

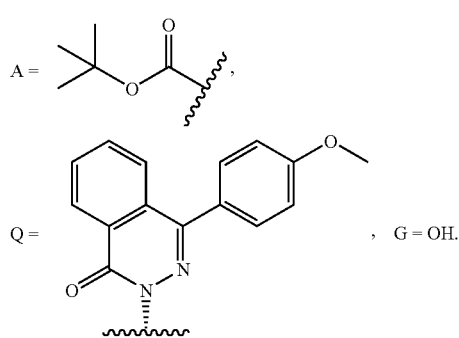

The title compound was prepared according to the Mitsunobu conditions set forth in step 1E with commercially available 4-(4-methoxy-phenyl)-2H-phthalazin-1-one, and subsequent hydrolysis of the ethyl ester via the procedure set forth in step 1G.

MS (ESI) m/z=700.1 (M+H)+.

Example 9

Compound of Formula IV, wherein

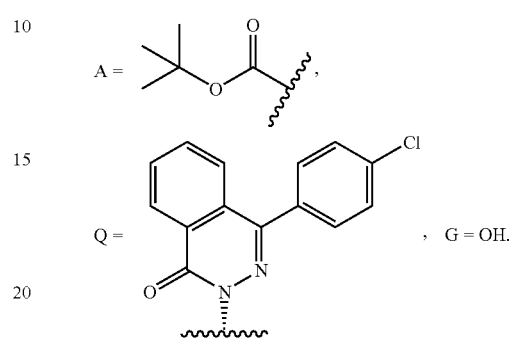

The title compound was prepared according to the Mitsunobu conditions set forth in step 1E with commercially available 4-(4-chloro-phenyl)-2H-phthalazin-1-one, and subsequent hydrolysis of the ethyl ester via the procedure set forth in step 1G.

MS (ESI) m/z=704.2 (M+H)+.

Example 10

Compound of Formula IV, wherein

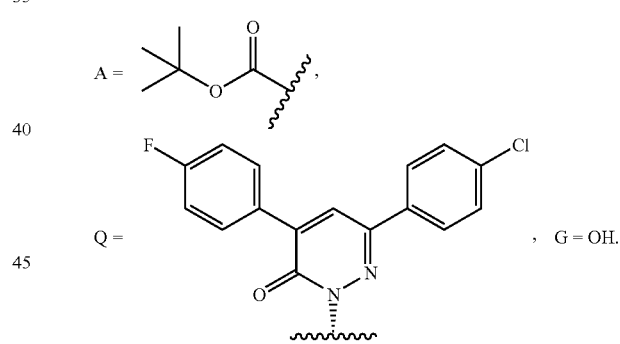

The title compound was prepared according to the Mitsunobu conditions set forth in step 1E with commercially available 6-(4-chloro-phenyl)-4-(4-fluoro-phenyl)-2H-pyridazin-3-one, and subsequent hydrolysis of the ethyl ester via the procedure set forth in step 1G.

MS (ESI) m/z=714.4 (M+H)+.

Example 11

Compound of Formula IV, wherein

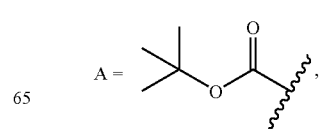

-continued

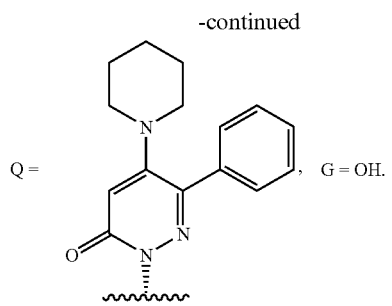

The title compound was prepared according to the Mitsunobu conditions set forth in step 1E with commercially available 3-phenyl-4-piperidinyl pyridazinone, and subsequent hydrolysis of the ethyl ester via the procedure set forth in step 1G.

MS (ESI) m/z=702.3 (M+H)+.

Example 12

Compound of Formula IV, wherein

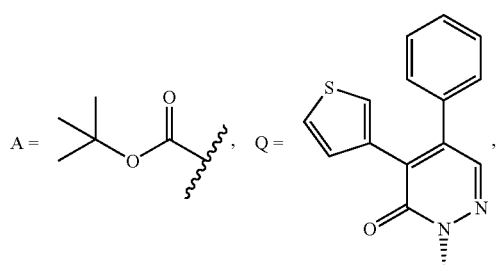

G = OH.

Step 12A.

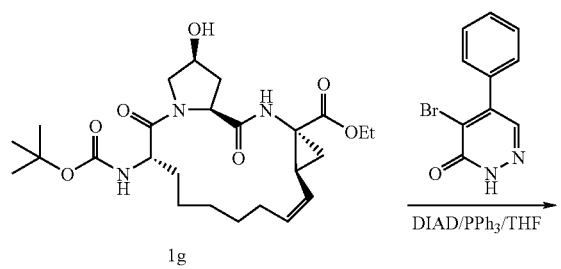

-continued

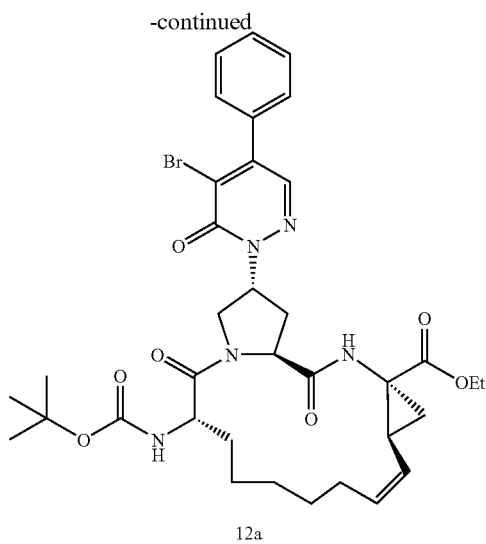

Mitsunobu conditions set forth in step 1E with commercially available 4-Bromo-5-phenyl-2H-pyridazin-3-one afforded compound 12a.

MS (ESI) m/z=726.3, 728.3 (M+H)+.

Steps 12B and 12C.

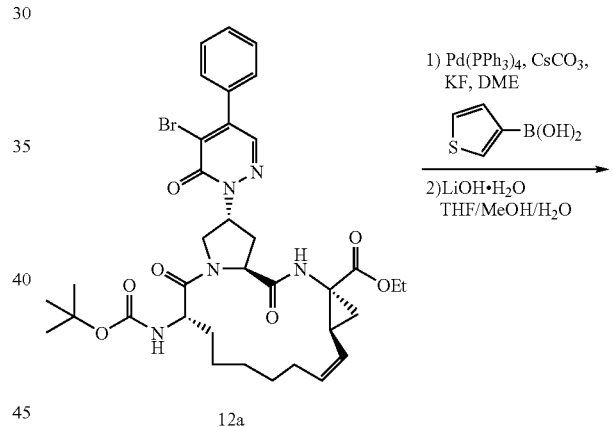

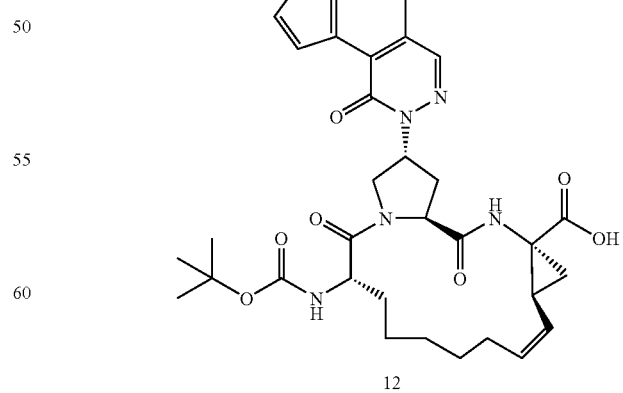

The title compound was prepared by the Suzuki coupling with thiophen-3-yl boronic acid and compound 12a according to the procedure set forth in step 1F, followed by hydrolysis of the ethyl ester via the method described in step 1G.

MS (ESI) m/z=730.3 (M+H)+.

Example 13

Compound of Formula IV, wherein

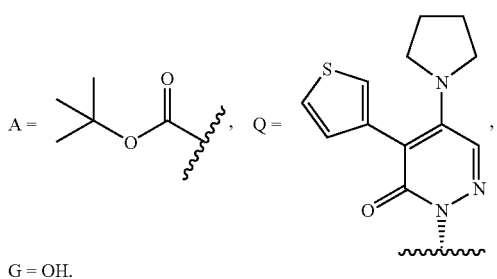

G = OH.

Step 13A.

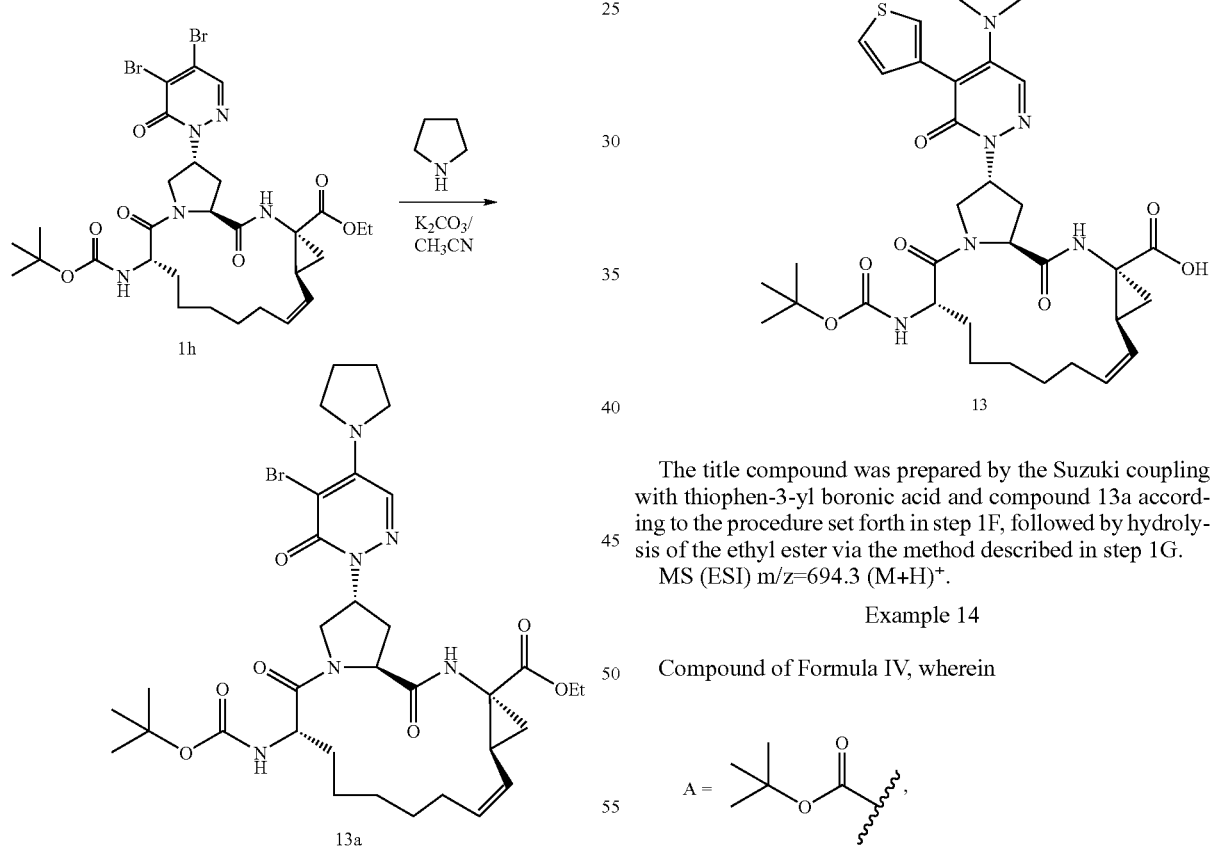

A mixture of compound in 1h (45 mg, 0.062 mmol), pyrrolidine (21 mL, 0.25 mmol), and potassium carbonate (34 mg, 0.25 mmol) in 2 mL of acetonitrile was heated to reflux for 3 hours. After cooling to room temperature, the mixture was filtered through a sinter glass funnel and the filtrate was concentrated in vacuo. The residue was re-dissolved in ethyl acetate and then washed once with saturated sodium carbonate, once with brine, dried (MgSO4), filtered, and concentrated under vacuum to give a yellow residue which was chromatographed over silica gel eluting with 3% methanol-chloroform to give 37 mg (83%) compound 13a.

MS (ESI) m/z=719.2, 721.2 (M+H)+.

Steps 13B and 13C.

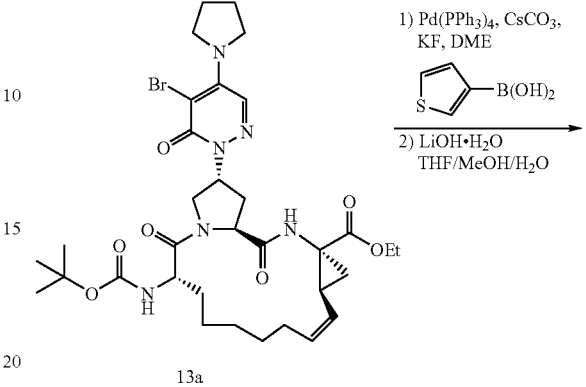

The title compound was prepared by the Suzuki coupling with thiophen-3-yl boronic acid and compound 13a according to the procedure set forth in step 1F, followed by hydrolysis of the ethyl ester via the method described in step 1G.

MS (ESI) m/z=694.3 (M+H)+.

Example 14

Compound of Formula IV, wherein

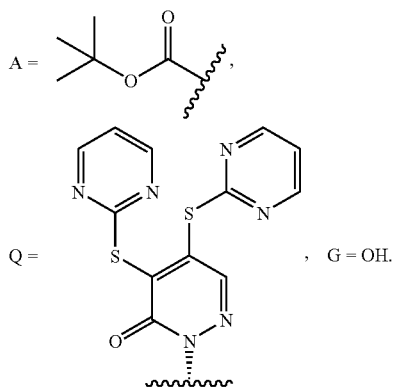

G = OH.

The title compound was prepared according to the conditions set forth in step 13A with commercially available pyrimidine-2-thiol, and subsequent hydrolysis of the ethyl ester via the procedure set forth in step 1G.

MS (ESI) m/z=764.3 (M+H)⁺.

Example 15

Compound of Formula IV, wherein

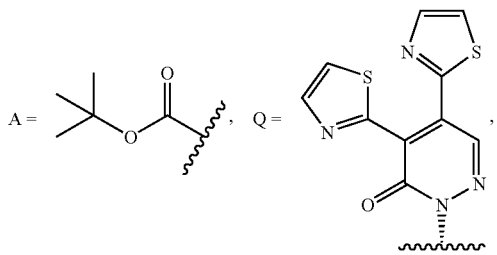

G = OH.

To a degassed solution of compound 1h (1 mmol) and thiazol-2-yl stannane (2 mmol) was added Pd(PPh₃)₄ (10 mol %). The mixture was degassed with nitrogen 2 more times and was heated to 100° C. for 3 hour. The cooled mixture was concentrated under vacuum and the residue was purified by column chromatography eluting with 30% EtOAc/Hexane followed by the hydrolysis of the ethyl ester via the method described in step 1G to give the title compound.

MS (ESI) m/z=710.3 (M+H)⁺.

Example 16

Compound of Formula IV, wherein

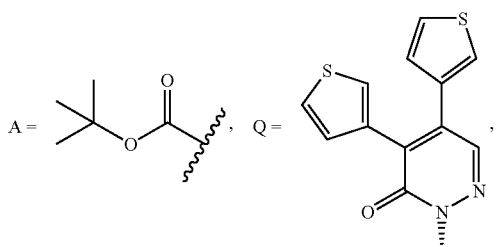

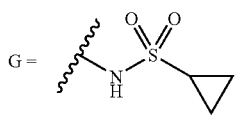

Step 16A.

Cyclopropylsulfonyl chloride (1.4 g, 10 mmol) was dissolved in 0.5 M ammonia in dioxane (50 ml, 25 mmol) at rt. The reaction was stirred at rt for 72 h. The precipitate was filtered and discarded. The clear filtrate was evaporated in vacuo and the white residue was dried on vacuum for 24 h to give cyclopropylsulfonamide (0.88 g, 74%).

¹H NMR (500 MHz, CD₃Cl): δ 4.62 (2H, s), 2.59 (1H, m), 1.20 (2H, m), 1.02 (2H, m).

Step 16B.

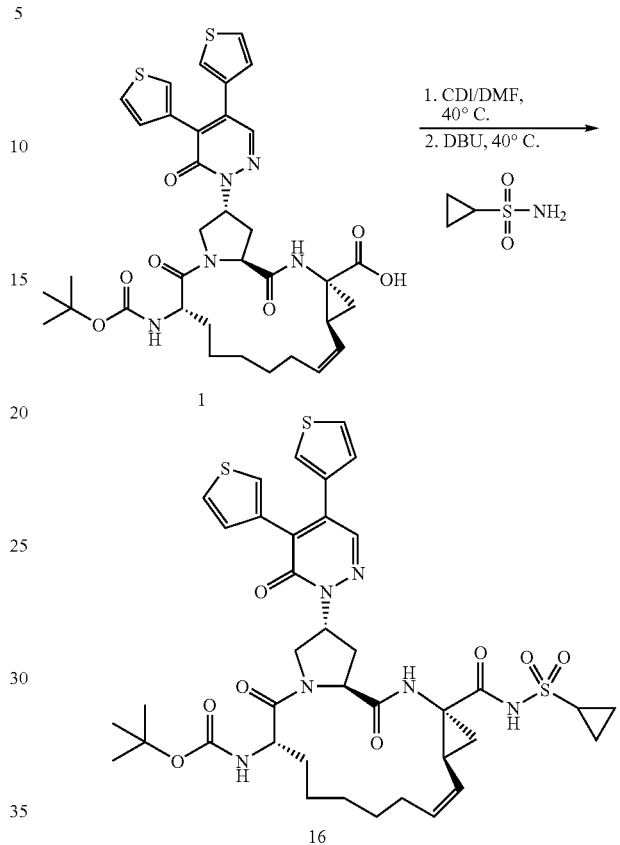

The title compound from Example 2 (6.0 mg) and carbonyldiimidazole (2.0 mg) were dissolved in 0.75 ml anhydrous DMF and the resulting solution was heated to 40° C. for 1 h. Cyclopropylsulfonamide (3.6 mg) was added to the reaction followed by DBU (4.5 mg). The reaction mixture was stirred at 40° C., until completion was confirmed by MS analysis. The reaction was diluted with 10 ml ethyl acetate and extracted with saturated aqueous with NaHCO₃ (2×2 mL) and brine (1×2 mL). The organic phase was dried over anhydrous Na₂SO₄, filtered, and then concentrated in vacuo. The residue was purified by silica gel flash chromatography using gradient elution with MeOH in DCM (1%→2%→5%) affording the title compound. (4.0 mg, 51%)

MS (ESI) m/z=811.42 (M+H)⁺.

Example 17

Compound of Formula IV, wherein

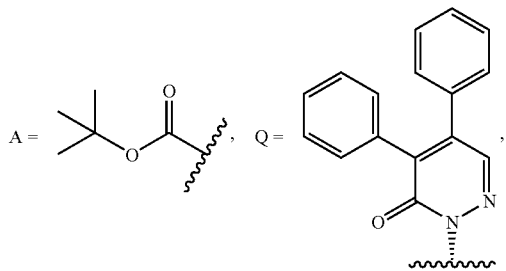

G = 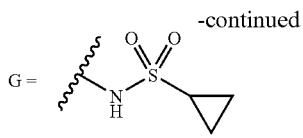

The title compound was prepared according to the conditions set forth in step 16B with the title compound from Example 2.
MS (ESI) m/z=799.49 (M+H)+.

Example 18

Compound of Formula IV, wherein

A = 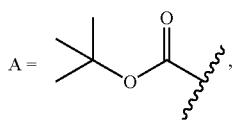,

Q = 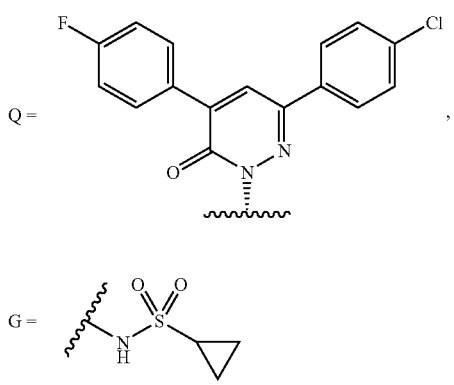,

G = 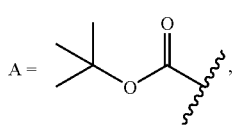

The title compound was prepared according to the conditions set forth in step 16B with the title compound from Example 10.
MS (ESI) m/z=817.4 (M+H)+.

Example 19

Compound of Formula IV, wherein

A = 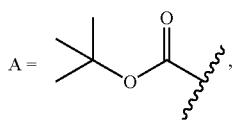,

Q = 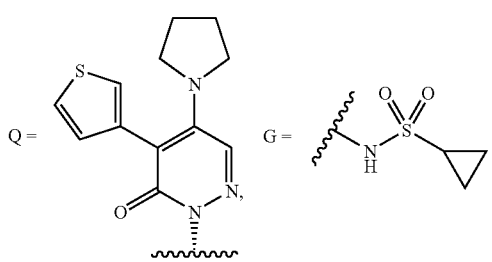

The title compound was prepared according to the conditions set forth in step 16B with the title compound from Example 13.
MS (ESI) m/z=798.4 (M+H)+.

Example 20

Compound of Formula IV, wherein

A = 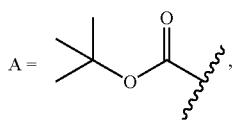,

Q = 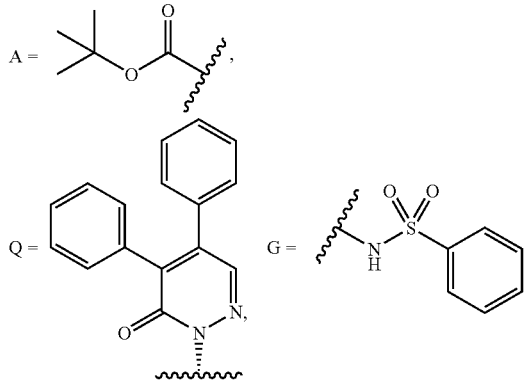  G = 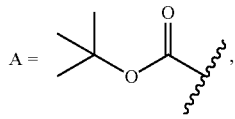

The title compound was prepared according to the chemistry laid forth in step 16B, using commercially available benzenesulfonamide and the title compound from Example 2.
MS (ESI) m/z=835.4 (M+H)+.

Example 21

Compound of Formula IV, wherein

A = 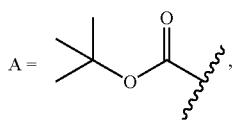,

Q = 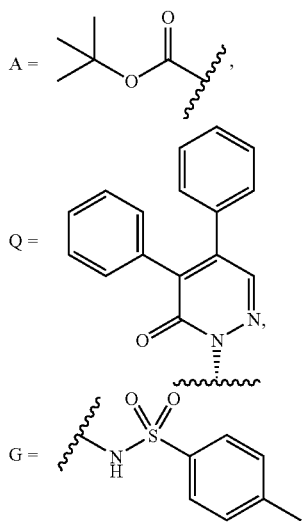,

The title compound was prepared according to the chemistry laid forth in step 16B, using commercially available p-toluenesulfonamide and the title compound from Example 2.
MS (ESI) m/z=849.4 (M+H)+.

Example 22

Compound of Formula IV, wherein

A = 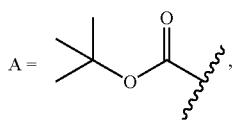,

-continued

Q = 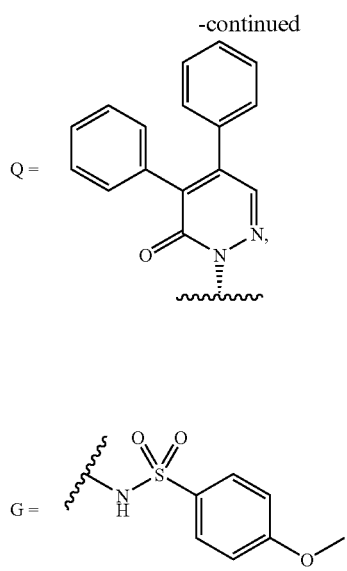

G = 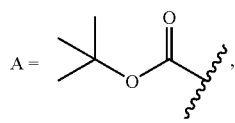

The title compound was prepared according to the chemistry laid forth in step 16B, using commercially available 4-methoxybenzenesulfonamide and the title compound from Example 2.

MS (ESI) m/z=865.4 (M+H)$^+$.

Example 23

Compound of Formula IV, wherein A

A = 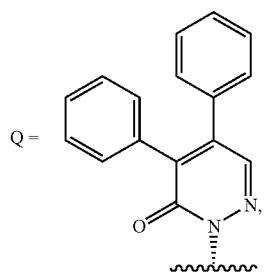

Q = 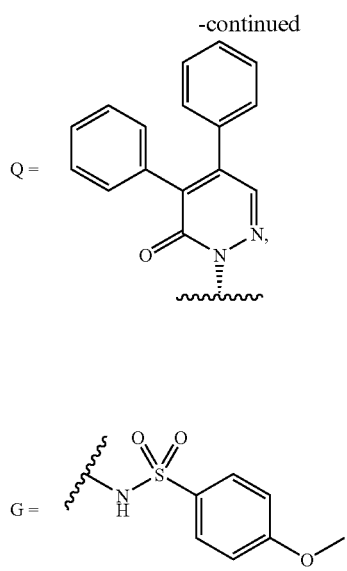

G = 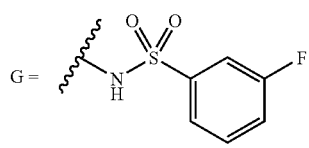

The title compound was prepared according to the chemistry laid forth in steps 16A and 16B, using commercially available 3-fluorobenzenesulfonyl chloride and the title compound from Example 2.

MS (ESI) m/z=853.4 (M+H)$^+$.

Example 24

Compound of Formula IV, wherein

A = 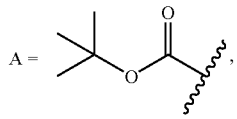

Q = 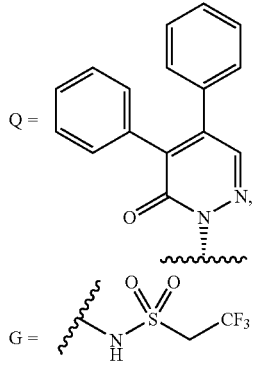

G = 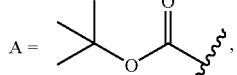

The title compound was prepared according to the chemistry laid forth in steps 16A and 16B, using commercially available 2,2,2-trifluoroethanesulfonyl chloride and the title compound from Example 2.

MS (ESI) m/z=841.4 (M+H)$^+$.

Example 25

Compound of Formula IV, wherein

A = 

Q = 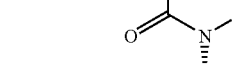

G = 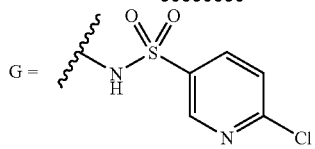

The title compound was prepared according to the chemistry laid forth in step 16B, using commercially available 4-chloro-3-pyridinesulfonamide and the title compound from Example 2.

MS (ESI) m/z=870.4 (M+H)$^+$.

Example 26

Compound of Formula IV, wherein

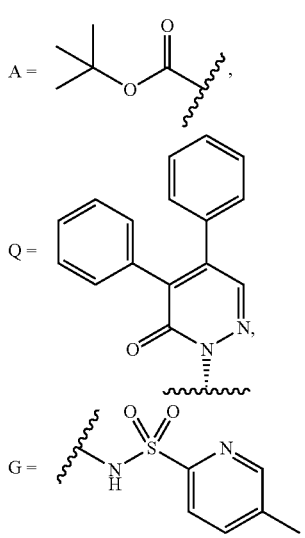

The title compound was prepared according to the chemistry laid forth in step 16B, using commercially available 5-methylpyridine-2-sulfonamide and the title compound from Example 2.

MS (ESI) m/z=850.4 (M+H)$^+$.

Example 27

Compound of Formula IV, wherein

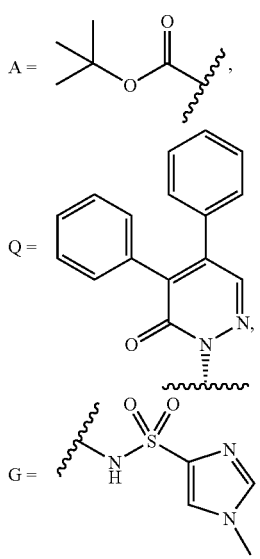

The title compound was prepared according to the chemistry laid forth in step 16B, using commercially available 1-methyl-1H-imidazole-4-sulfonamide and the title compound from Example 2.

MS (ESI) m/z=839.4 (M+H)$^+$.

Example 28

Compound of Formula IV, wherein

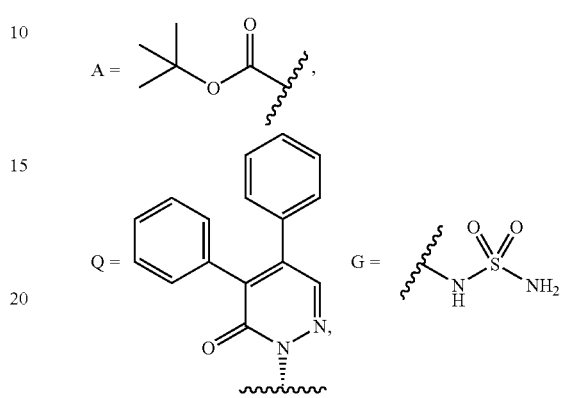

The title compound was prepared according to the chemistry laid forth in step 16B, using commercially available sulfamide and the title compound from Example 2.

MS (ESI) m/z=774.4 (M+H)$^+$.

Example 29

Compound of Formula IV, wherein

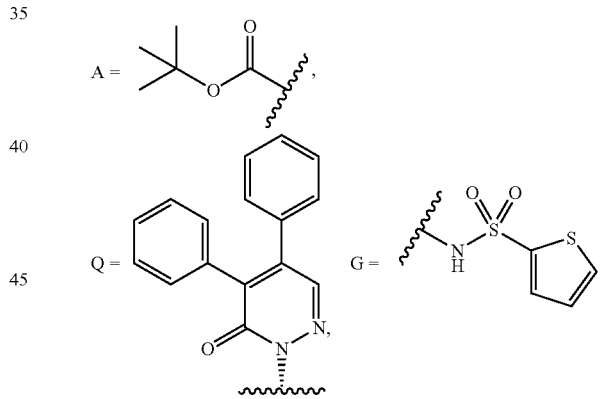

The title compound was prepared according to the chemistry laid forth in steps 16A and 16B, using commercially available thiophene-2-sulfonyl chloride and the title compound from Example 2.

MS (ESI) m/z=821.6 (M+H)$^+$.

Example 30

Compound of Formula IV, wherein

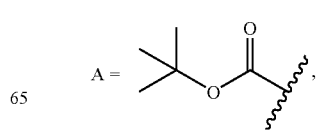

-continued

Q = 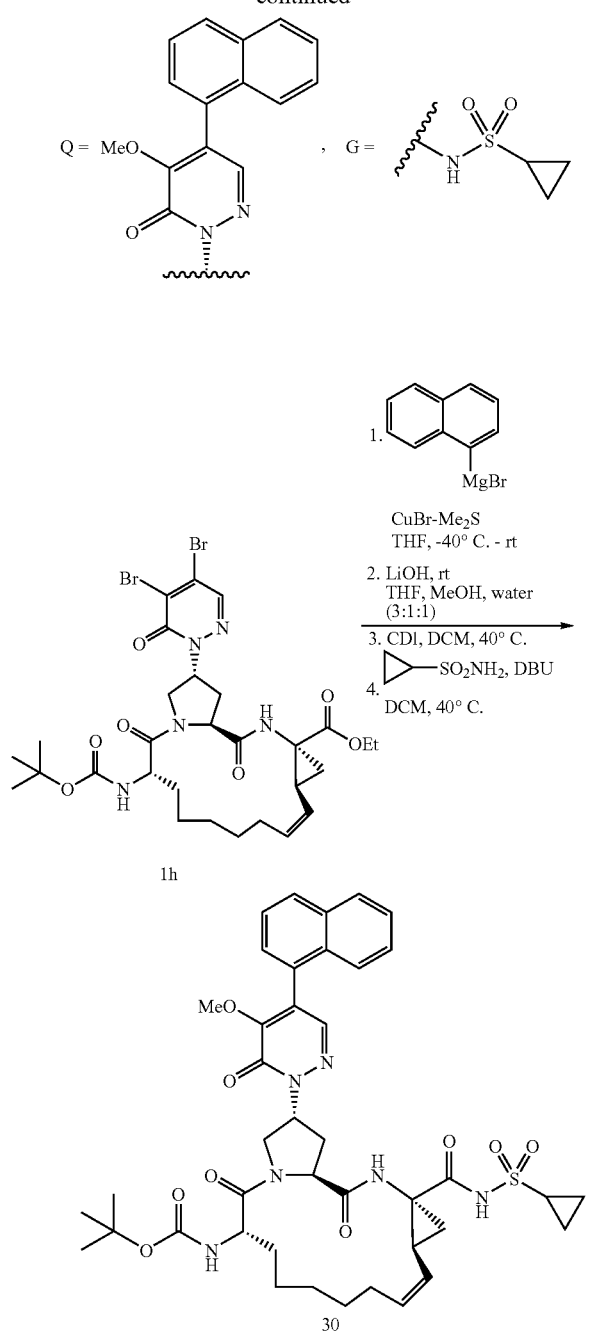, G =

Example 31

Compound of Formula IV, wherein

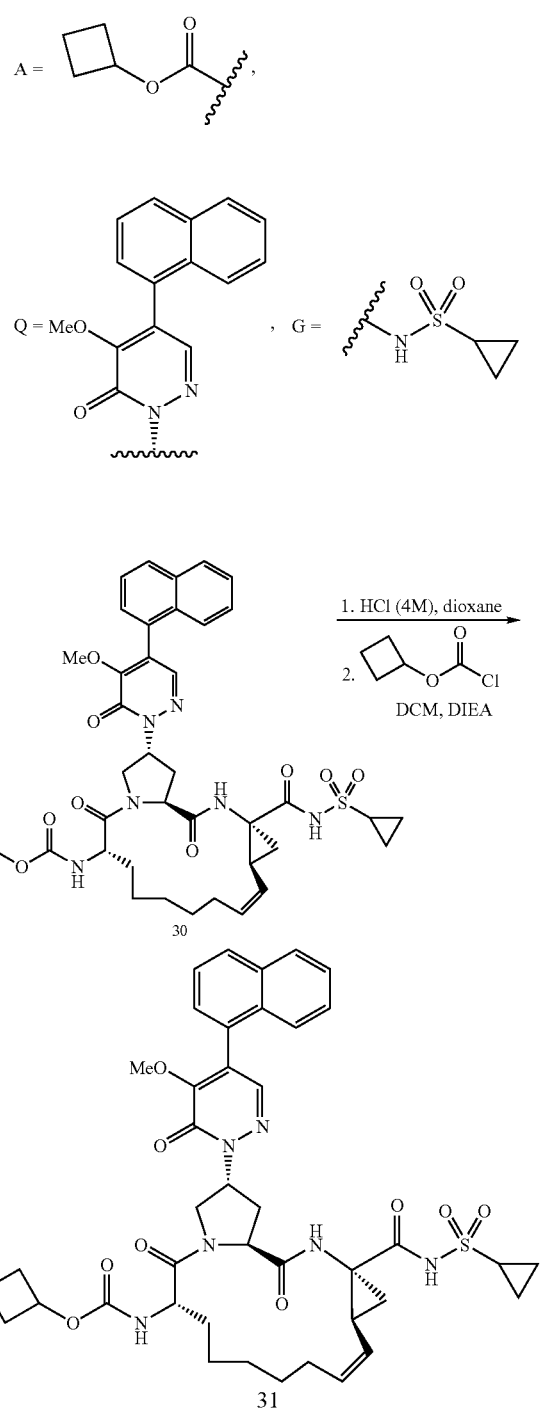

water, respectively), then sulfonimide formation following the steps outlined in 16B.

MS (ESI) m/z=803.2 (M+H)$^+$.

The title compound was prepared by first treating intermediate 1h (400 mg, 0.55 mmol) with the cuprate generated from 1-naphthylmagnesium bromide (0.25 M solution, 22 mL, 5.55 mmol) and copper (I) bromide-dimethyl sulfide complex (620 mg, 3.01 mmol) in 100 mL THF (the Grignard was added to the copper species at −40° C. and stirred for 30 min at that temperature before being added to the bis-bromide). It was important to note that additional equivalents of the Grignard reagent was sometimes necessary in order to drive the reaction toward product formation. As in previous examples, the final steps involved hydrolysis using lithium hydroxide (typically 10 equiv, in a 3:1:1 mixture of THF, methanol, and The title compound was prepared in two steps consisting of (1) Boc-deprotection using 20 equiv of HCl (4M) in dioxane, and (2) carbamate formation using cyclobutylchloroformate (2 equiv) in the presence of DIEA (3 equiv).
MS (ESI) m/z=801.2 (M+H)+.

Example 32

Compound of Formula IV, wherein

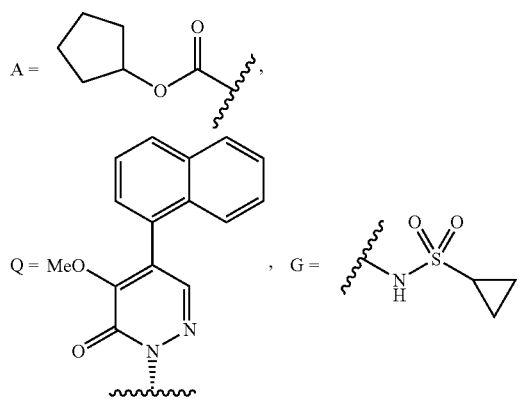

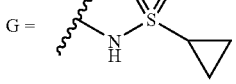

The title compound was prepared in an analogous fashion to Example 31, except using cyclopentylchloroformate as the electrophile.
MS (ESI) m/z=815.2 (M+H)+.

Example 33

Compound of Formula IV, wherein

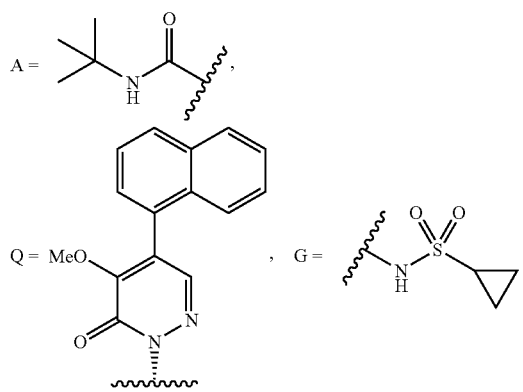

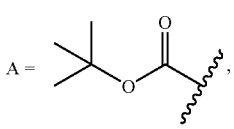

The title compound was prepared in an analogous fashion to Example 31, except using tert-butyl isocyanate as the electrophile.
MS (ESI) m/z=802.2 (M+H)+.

Example 34

Compound of Formula IV, wherein

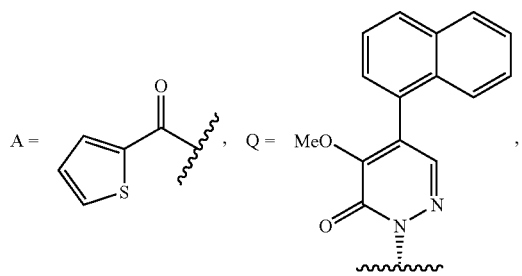

-continued

G =

The title compound was prepared in an analogous fashion to Example 31, except using the active species generated from 1-thiophenecarboxylic acid and HATU/DIEA as the electrophile.
MS (ESI) m/z=813.1 (M+H)+.

Example 35

Compound of Formula IV, wherein

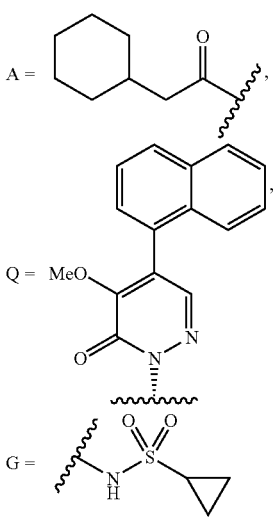

The title compound was prepared in an analogous fashion to Example 31, except using cyclohexylacetyl chloride as the electrophile.
MS (ESI) m/z=827.2 (M+H)+.

Example 36

Compound of Formula IV, wherein

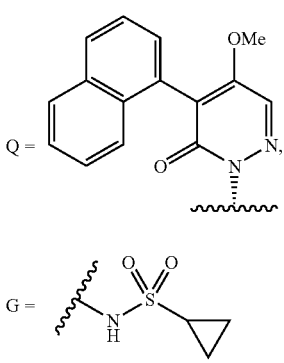

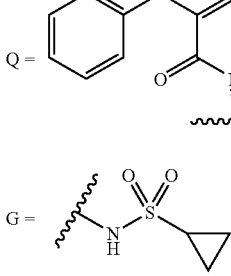

The title compound was prepared in an analogous fashion to Example 13, except NaOMe (25 wt. % in MeOH) was used as the nucleophilic species in the first step, and 1-naphthyl-boronic acid was used in the Suzuki coupling. Hydrolysis and sulfonamide formation were carried out as in Example 16.

MS (ESI) m/z=803.1 (M+H)⁺.

Example 37

Compound of Formula IV, wherein

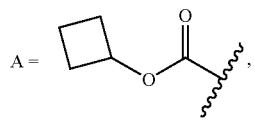

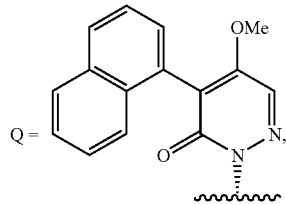

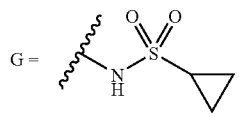

Beginning with Example 36, the title compound was prepared in an identical fashion to Example 31.

MS (ESI) m/z=801.2 (M+H)⁺.

Example 38

Compound of Formula IV, wherein

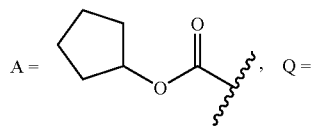

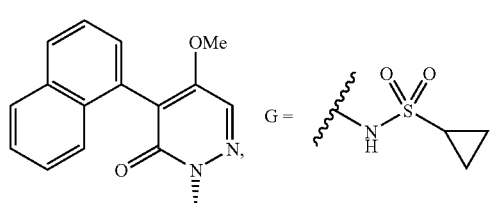

Beginning with Example 36, the title compound was prepared in an identical fashion to Example 32.

MS (ESI) m/z=815.2 (M+H)⁺.

Example 39

Compound of Formula IV, wherein

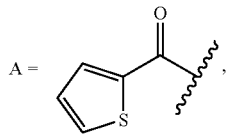

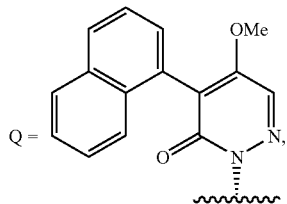

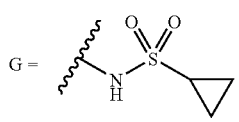

Beginning with Example 36, the title compound was prepared in an identical fashion to Example 34.

MS (ESI) m/z=813.0 (M+H)⁺.

Example 40

Compound of Formula IV, wherein

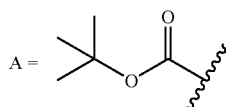

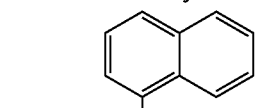

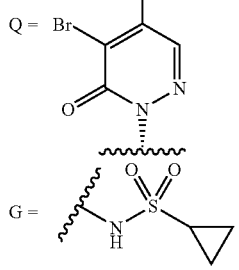

The title compound was produced as a minor product in the synthesis of Example 30 (this bromide can be isolated in higher quantities if the hydrolysis of the ethyl ester was carried out for a shorter duration).
MS (ESI) m/z=851.1, 853.1 (M+H)+.

Example 41

Compound of Formula IV, wherein

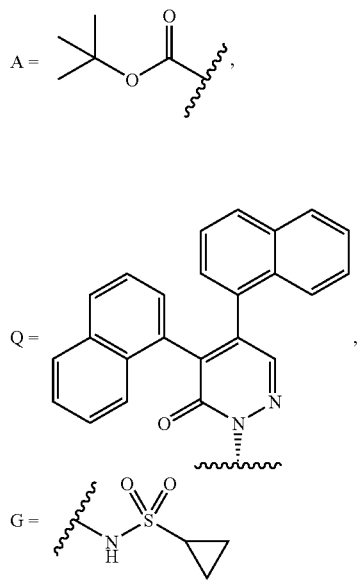

The title compound was generated as a secondary product in the synthesis of Example 30. An alternative synthesis would be to employ the bis-Suzuki strategy outlined in Example 1.
MS (ESI) m/z=899.2 (M+H)+.

Example 42

Compound of Formula IV, wherein

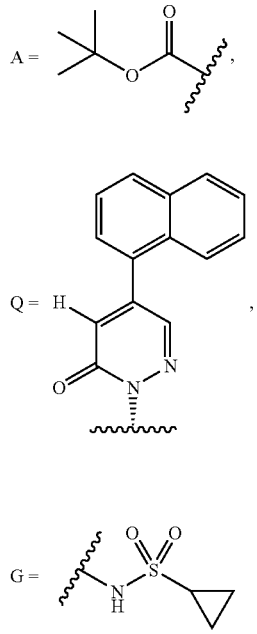

The title compound was generated as a secondary product in the synthesis of Example 30.
MS (ESI) m/z=773.9 (M+H)+.

Example 43

Compound of Formula IV, wherein

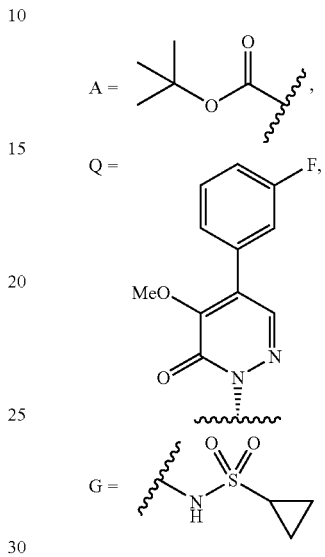

The title compound was generated in an analogous fashion to Example 30, except using 3-fluoro-phenylmagnesium bromide as the Grignard source.
MS (ESI) m/z=809.3 (M+H)+.

Example 44

Compound of Formula IV, wherein

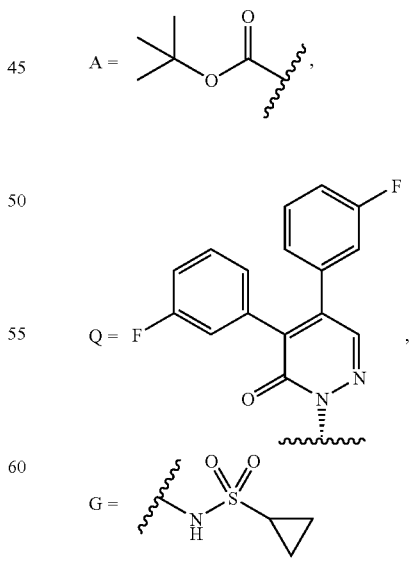

The title compound was generated as a secondary product in the synthesis of Example 43. An alternative synthesis would be to employ the bis-Suzuki strategy outlined in Example 1.

MS (ESI) m/z=857.3 (M+H)+.

Example 45
Compound of Formula IV, wherein

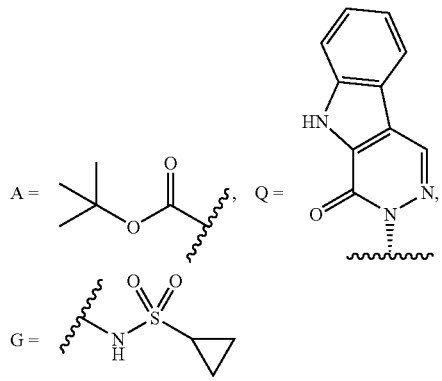

The title compound was prepared in an analogous fashion, beginning with a Mitsunobu reaction (conditions set forth in step 1E) with 2,9-Dihydro-2,3,9-triaza-fluoren-1-one. Hydrolysis of the ethyl ester via the procedure set forth in step 1G, followed by sulfonamide formation delivered the title compound.

MS (ESI) m/z=857.3 (M+H)+.

Examples 46-100

(Formula III, Table 2) are made following the procedures described in examples 1-46.

TABLE 2

(III)

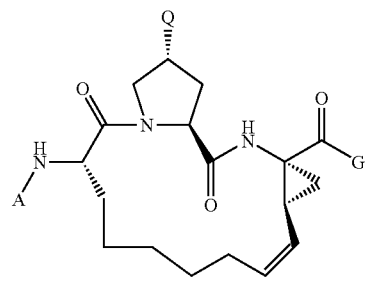

| Example # | A | Q | G |
|---|---|---|---|
| 46 | 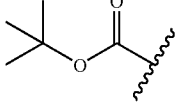 | 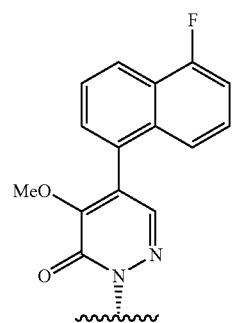 | 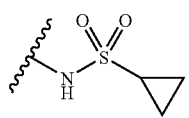 |
| 47 | 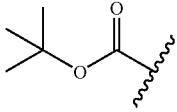 | 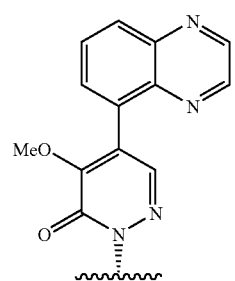 | 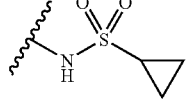 |

TABLE 2-continued
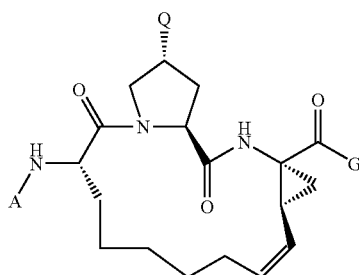
(III)
| Example # | A | Q | G |
|---|---|---|---|
| 48 | 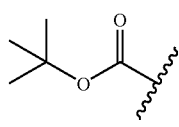 | 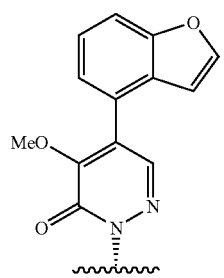 | 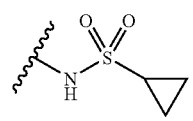 |
| 49 | 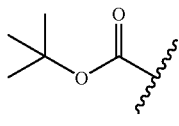 | 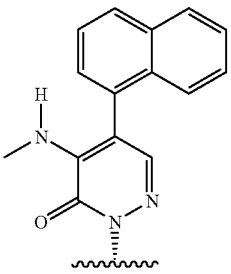 | 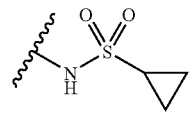 |
| 50 | 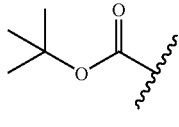 | 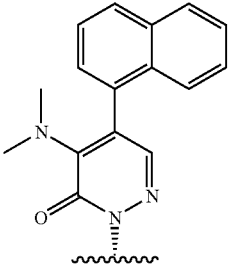 | 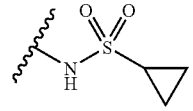 |
| 51 | 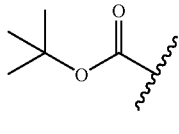 | 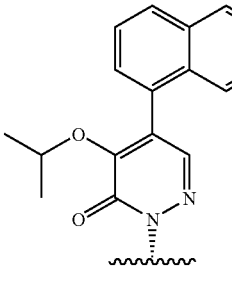 | 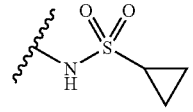 |

TABLE 2-continued
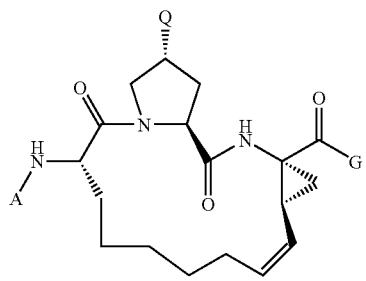
(III)
| Example # | A | Q | G |
|---|---|---|---|
| 52 | 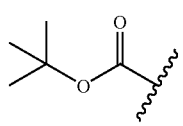 | 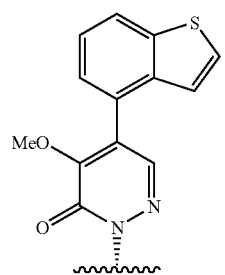 | 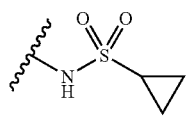 |
| 53 | 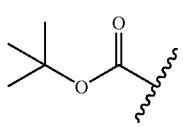 | 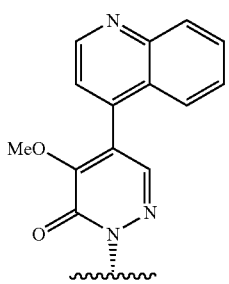 | 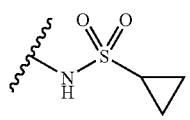 |
| 54 | 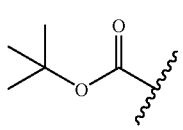 | 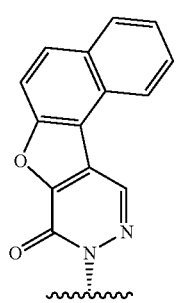 | 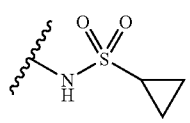 |
| 55 | 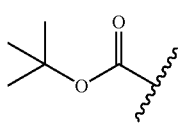 | 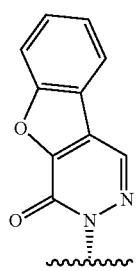 | 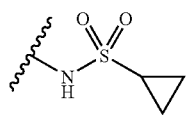 |

TABLE 2-continued (III)

| Example # | A | Q | G |
|---|---|---|---|
| 56 | cyclopentyl ester | 4-bromo-5-(naphthalen-1-yl)pyridazin-3(2H)-one | cyclopropanesulfonamide |
| 57 | cyclopentyl ester | 4,5-di(naphthalen-1-yl)pyridazin-3(2H)-one | cyclopropanesulfonamide |
| 58 | cyclopentyl ester | 5-(naphthalen-1-yl)pyridazin-3(2H)-one | cyclopropanesulfonamide |
| 59 | cyclopentyl ester | 4,5-bis(3-fluorophenyl)pyridazin-3(2H)-one | cyclopropanesulfonamide |

TABLE 2-continued (III)

| Example # | A | Q | G |
|---|---|---|---|
| 60 | cyclopentyl ester | 4-(3-fluorophenyl)-5-methoxy-pyridazin-3(2H)-one | cyclopropanesulfonamide |
| 61 | cyclopentyl ester | 5H-pyridazino[4,5-b]indol-1(2H)-one | cyclopropanesulfonamide |
| 62 | cyclopentyl ester | 4-(5-fluoronaphthalen-1-yl)-5-methoxy-pyridazin-3(2H)-one | cyclopropanesulfonamide |
| 63 | cyclopentyl ester | 5-methoxy-4-(quinoxalin-5-yl)pyridazin-3(2H)-one | cyclopropanesulfonamide |

TABLE 2-continued (III)

| Example # | A | Q | G |
|---|---|---|---|
| 64 | cyclopentyl ester | 4-(benzofuran-4-yl)-5-methoxy-pyridazin-3(2H)-one | cyclopropanesulfonamide |
| 65 | cyclopentyl ester | 4-(naphthalen-1-yl)-5-(methylamino)-pyridazin-3(2H)-one | cyclopropanesulfonamide |
| 66 | cyclopentyl ester | 4-(naphthalen-1-yl)-5-(dimethylamino)-pyridazin-3(2H)-one | cyclopropanesulfonamide |
| 67 | cyclopentyl ester | 4-(naphthalen-1-yl)-5-isopropoxy-pyridazin-3(2H)-one | cyclopropanesulfonamide |

TABLE 2-continued
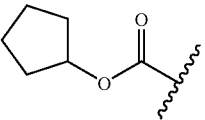
(III)
| Example # | A | Q | G |
|---|---|---|---|
| 68 | 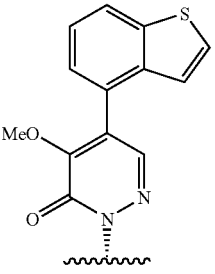 | 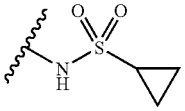 | 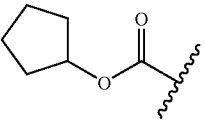 |
| 69 | 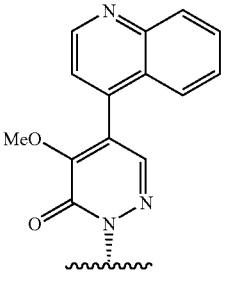 | 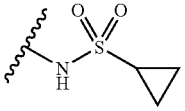 | 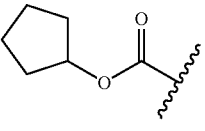 |
| 70 | 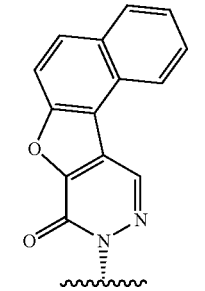 | 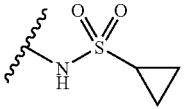 | 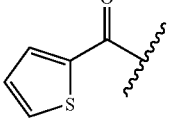 |
| 71 | 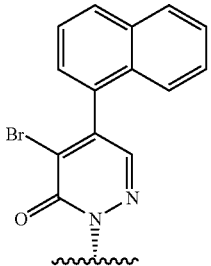 | 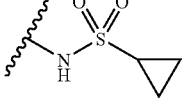 | |

TABLE 2-continued
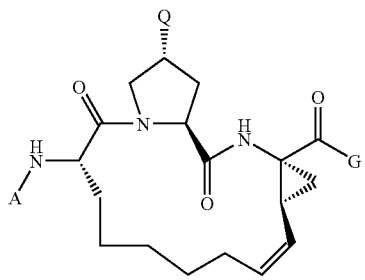
(III)
| Example # | A | Q | G |
|---|---|---|---|
| 72 | 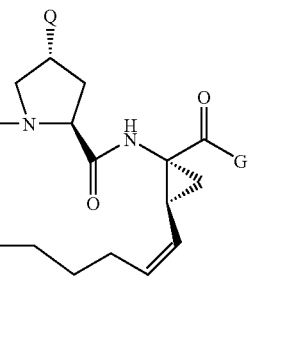 |  | 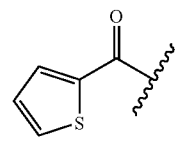 |
| 73 | 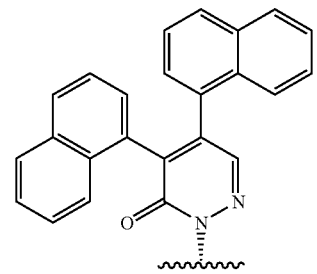 | 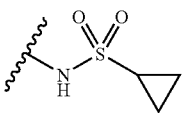 | 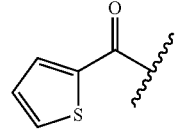 |
| 74 | 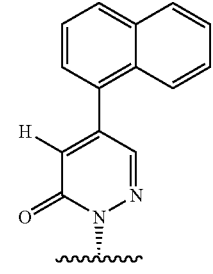 | 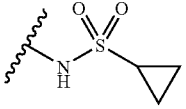 | 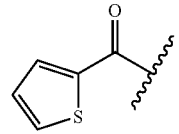 |
| 75 | 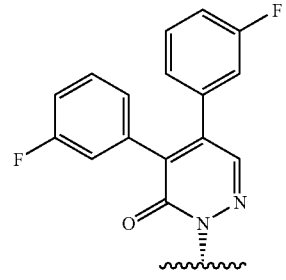 | 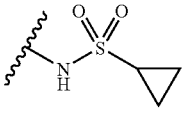 | 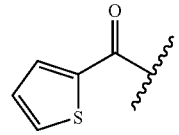 |

TABLE 2-continued (III)

| Example # | A | Q | G |
|---|---|---|---|
| 76 | thiophene-2-carbonyl | pyrido-pyridazinone | cyclopropanesulfonamide |
| 77 | thiophene-2-carbonyl | 5-fluoronaphthyl-methoxy-pyridazinone | cyclopropanesulfonamide |
| 78 | thiophene-2-carbonyl | quinoxalinyl-methoxy-pyridazinone | cyclopropanesulfonamide |
| 79 | thiophene-2-carbonyl | benzofuranyl-methoxy-pyridazinone | cyclopropanesulfonamide |

TABLE 2-continued
(III)
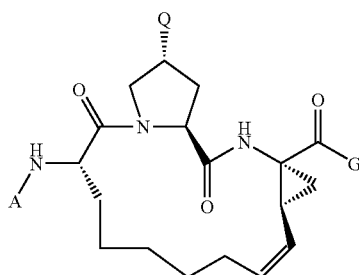
| Example # | A | Q | G |
|---|---|---|---|
| 80 | 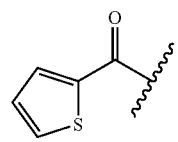 | 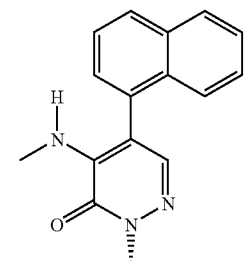 | 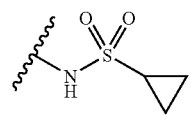 |
| 81 | 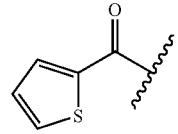 | 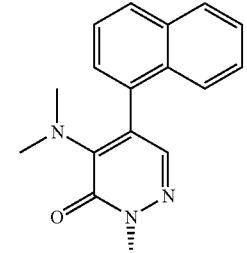 | 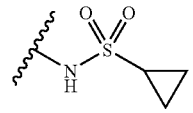 |
| 82 | 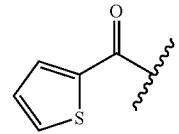 | 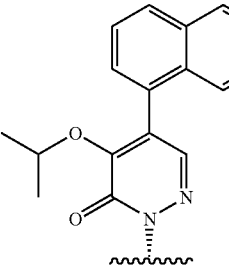 | 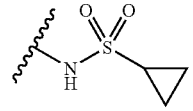 |
| 83 | 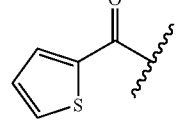 | 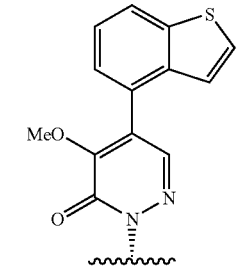 | 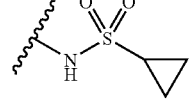 |

TABLE 2-continued
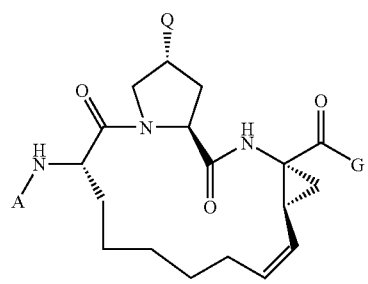
(III)
| Example # | A | Q | G |
|---|---|---|---|
| 84 | 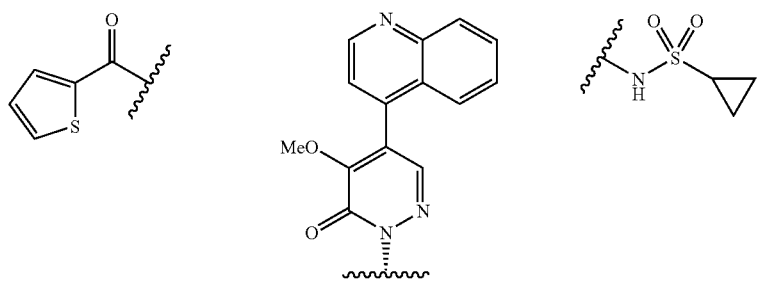 | | |
| 85 | 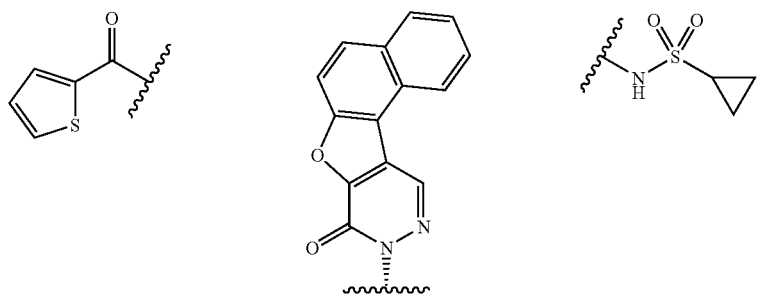 | | |
| 86 | 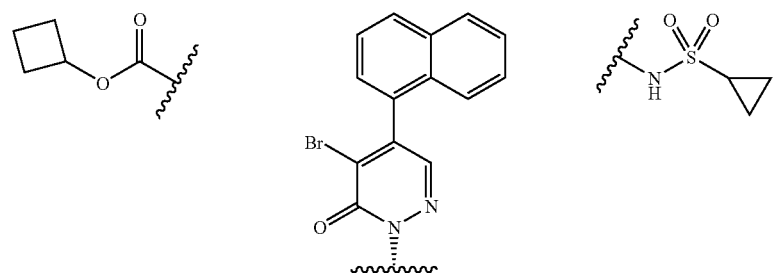 | | |
| 87 | 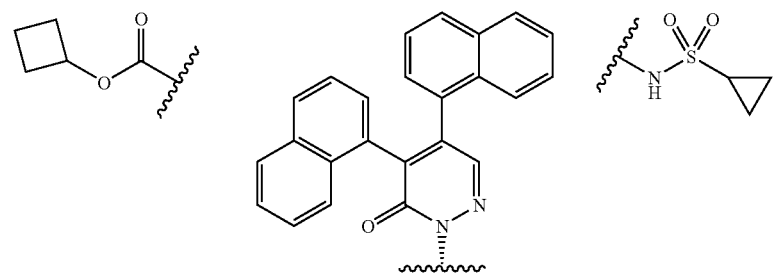 | | |

TABLE 2-continued
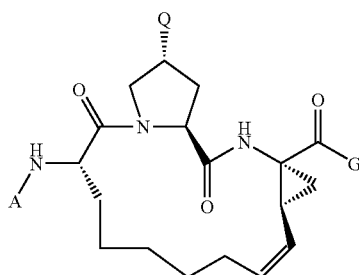
(III)
| Example # | A | Q | G |
|---|---|---|---|
| 88 | 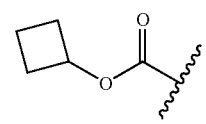 | 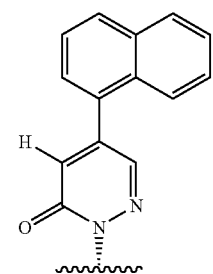 | 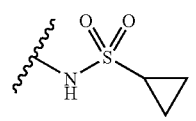 |
| 89 | 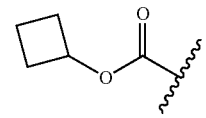 | 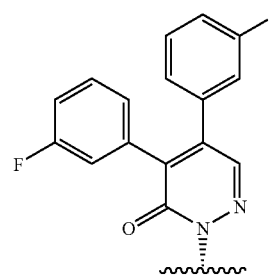 | 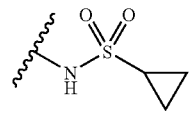 |
| 90 | 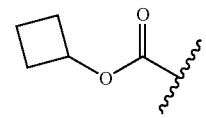 | 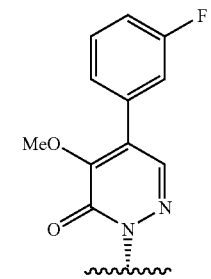 | 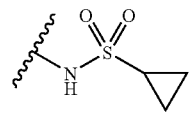 |
| 91 | 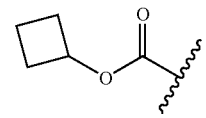 | 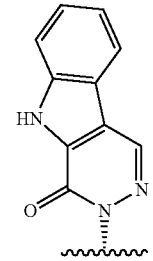 | 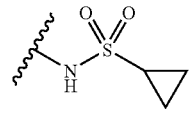 |

TABLE 2-continued (III)

| Example # | A | Q | G |
|---|---|---|---|
| 92 | cyclobutyl ester | 5-fluoronaphthalen-1-yl / 4-methoxy-pyridazinone | cyclopropanesulfonamide |
| 93 | cyclobutyl ester | quinoxalin-5-yl / 4-methoxy-pyridazinone | cyclopropanesulfonamide |
| 94 | cyclobutyl ester | benzofuran-4-yl / 4-methoxy-pyridazinone | cyclopropanesulfonamide |
| 95 | cyclobutyl ester | naphthalen-1-yl / 4-methylamino-pyridazinone | cyclopropanesulfonamide |

TABLE 2-continued
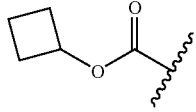
(III)
| Example # | A | Q | G |
|---|---|---|---|
| 96 | 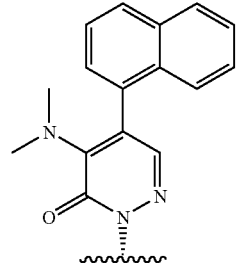 | 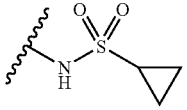 | 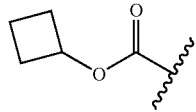 |
| 97 | 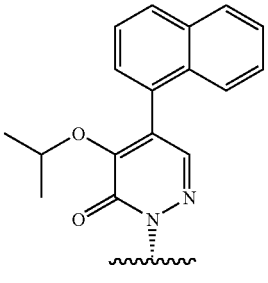 | 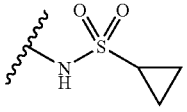 | 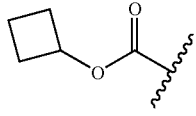 |
| 98 | 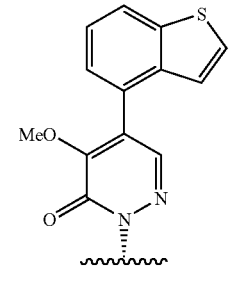 | 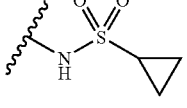 | 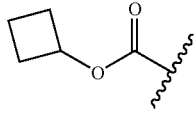 |
| 99 | 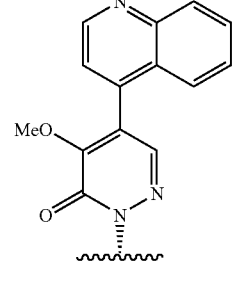 | 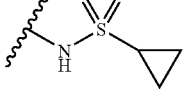 | |

TABLE 2-continued

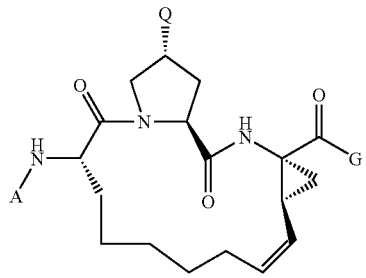

(III)

| Example # | A | Q | G |
|---|---|---|---|
| 100 | 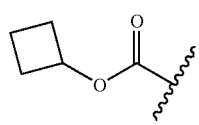 | 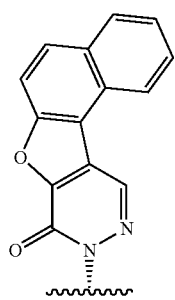 | 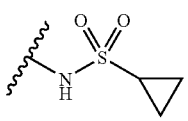 |

Although the invention has been described with respect to various preferred embodiments, it is not intended to be limited thereto, but rather those skilled in the art will recognize that variations and modifications may be made therein which are within the spirit of the invention and the scope of the appended claims.

The compounds of the present invention exhibit potent inhibitory properties against the HCV NS3 protease. The following examples describe assays in which the compounds of the present invention can be tested for anti-HCV effects.

Example 101

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence is measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 µM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-NH$_2$, AnaSpec 22991, MW 1548.6) is used as the fluorogenic peptide substrate. The assay buffer contains 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, [−20° C.] and HCV Inh 2 (Anaspec 25346, MW 913.1) Ac-Asp-Glu-Dif-Cha-Cys-OH, are used as reference compounds.

IC50 values are calculated using XLFit in ActivityBase (IDBS) using equation 205: $y=A+((B-A)/(1+((C/x)\char`\^D)))$.

Example 102

Cell-based Replicon Assay

Quantification of HCV replicon RNA (HCV Cell Based Assay) is accomplished using the Huh 11-7 cell line (Lohmann, et al Science 285:110-113, 1999). Cells are seeded at $4 \times 10^3$ cells/well in 96 well plates and fed media containing DMEM (high glucose), 10% fetal calf serum, penicillin-streptomycin and non-essential amino acids. Cells are incubated in a 7.5% $CO_2$ incubator at 37° C. At the end of the incubation period, total RNA is extracted and purified from cells using Ambion RNAqueous 96 Kit (Catalog No. AM1812). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

```
HCV Forward primer "RBNS5bfor"
5'GCTGCGGCCTGTCGAGCT:        (SEQ ID NO: 1)

HCV Reverse primer "RBNS5Brev"
5'CAAGGTCGTCTCCGCATAC.       (SEQ ID NO 2)
```

Detection of the RT-PCR product is accomplished using the Applied Biosystems (ABI) Prism 7500 Sequence Detection System (SDS) that detects the fluorescence that is emitted when the probe, which is labeled with a fluorescence reporter dye and a quencher dye, is degraded during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

(SEQ ID NO: 3)
5' FAM-CGAAGCTCCAGGACTGCACGATGCT-TAMRA

FAM = Fluorescence reporter dye.

TAMRA: = Quencher dye.

The RT reaction is performed at 48° C. for 30 minutes followed by PCR. Thermal cycler parameters used for the PCR reaction on the ABI Prism 7500 Sequence Detection System are: one cycle at 95° C., 10 minutes followed by 40 cycles each of which include one incubation at 95° C. for 15 seconds and a second incubation for 60° C. for 1 minute.

To normalize the data to an internal control molecule within the cellular RNA, RT-PCR is performed on the cellular messenger RNA glyceraldehyde-3-phosphate dehydrogenase (GAPDH). The GAPDH copy number is very stable in the cell lines used. GAPDH RT-PCR is performed on the same RNA sample from which the HCV copy number is determined. The GAPDH primers and probes are contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines.

The effect of a specific anti-viral compound on HCV replicon RNA levels in Huh-11-7 cells is determined by comparing the amount of HCV RNA normalized to GAPDH (e.g. the ratio of HCV/GAPDH) in the cells exposed to compound versus cells exposed to the DMSO vehicle (negative control). Specifically, cells are seeded at $4 \times 10^3$ cells/well in a 96 well plate and are incubated either with: 1) media containing 1% DMSO (0% inhibition control), or 2) media/1% DMSO containing a fixed concentration of compound. 96 well plates as described above are then incubated at 37° C. for 4 days (EC50 determination). Percent inhibition is defined as:

% Inhibition=100−100*S/C1 where
S=the ratio of HCV RNA copy number/GAPDH RNA copy number in the sample;
C1=the ratio of HCV RNA copy number/GAPDH RNA copy number in the 0% inhibition control (media/1% DMSO).

The dose-response curve of the inhibitor is generated by adding compound in serial, three-fold dilutions over three logs to wells starting with the highest concentration of a specific compound at 1.5 uM and ending with the lowest concentration of 0.23 nM. Further dilution series (500 nM to 0.08 nM for example) is performed if the EC50 value is not positioned well on the curve. EC50 is determined with the IDBS Activity Base program "XL Fit" using a 4-parameter, non-linear regression fit (model #205 in version 4.2.1, build 16).

In the above assays, representative compounds of the present invention are found to have HCV replication inhibitory activity and HCV NS3 protease inhibitory activity. These compounds were also effective in inhibiting HCV NS3 proteases of different HCV genotypes including genotypes 1, 2, 3 and 4.

Representative compounds were tested in the above assays (Example 101 and Example 102). Exemplary compounds disclosed herein were found to have activities in the ranges of <=0.2 nM-100 nM in the NS3/NS4a Protease Enzyme Assay and <=0.2 nM-1000 nM in the Cell-Based Replicon Assay. For example, compounds of Examples 30, 32 and 34 showed IC50 of 0.1 nM, 0.4 nM and 0.2 nM in the NS3/NS4a Protease Enzyme Assay respectively, and all showed EC50 of <0.2 nM in the Cell-Based Replicon Assay.

What is claimed:

1. A compound of Formula II:

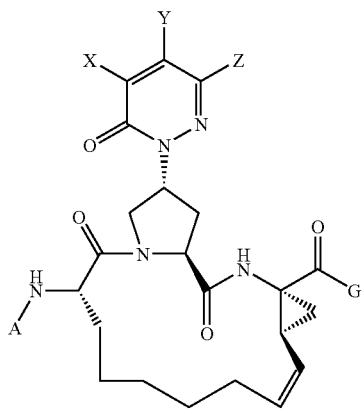

(II)

Wherein

A is selected from the group consisting of —(C=O)—O—$R^1$, —(C=O)—$R^2$, —C(=O)—$NR^1R^2$, or —S(O)$_2$—$R^1$, —S(O)$_2$—N $R^1R^2$;

Wherein, $R^1$ is independently selected at each occurrence from the following groups:

(i) aryl;
(ii) substituted aryl;
(iii) heteroaryl;
(iv) substituted heteroaryl;
(v) heterocycloalkyl;
(vi) substituted heterocycloalkyl; and
(vii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

Wherein, $R^2$ is independently selected at each occurrence from the following groups:

(i) hydrogen;
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

G is selected from the group consisting of —NHS(O)$_2$—$R^3$ and —NH(SO$_2$)$NR^4R^5$;

wherein, $R^3$ is independently selected at each occurrence from the following groups:

(i) aryl;
(ii) substituted aryl;
(iii) heteroaryl;
(iv) substituted heteroaryl;
(v) heterocycloalkyl;
(vi) substituted heterocycloalkyl; and
(vii) —$C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

provided that $R^3$ is not —$CH_2Ph$ or —$CH_2CH_2Ph$;

Wherein, $R^4$ and $R^5$ are independently selected at each occurrence from the following groups:

(i) hydrogen;
(ii) aryl;
(iii) substituted aryl;
(iv) heteroaryl;
(v) substituted heteroaryl;
(vi) heterocycloalkyl;
(vii) substituted heterocycloalkyl; and (viii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

X, Y, and Z are independently selected at each occurrence from the following groups:
(i) hydrogen;
(ii) —CN;
(iii) —$N_3$;
(iv) halogen;
(v) $OR^6$;
(vi) $NR^7R^8$;
(vii) aryl;
(viii) substituted aryl;
(ix) heteroaryl;
(x) substituted heteroaryl;
(xi) —$C_3$-$C_{12}$ cycloalkyl, substituted —$C_3$-$C_{12}$ cycloalkyl, heterocycloalkyl, substituted heterocycloalkyl;
(xii) —$C_1$-$C_6$ alkyl containing 0, 1, 2, or 3 heteroatoms selected from O, S, or N, optionally substituted with one or more substituent selected from halogen, aryl, substituted aryl, heteroaryl, or substituted heteroaryl;
(xiii) —$C_2$-$C_6$ alkenyl containing 0, 1, 2, or 3 heteroatoms selected from O, S, or N, optionally substituted with one or more substituent selected from halogen, aryl, substituted aryl, heteroaryl, or substituted heteroaryl; and
(xiv) —$C_2$-$C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;

or, in the alternative, X and Y or Y and Z taken together with the carbon atoms to which they are attached form a cyclic moiety, which is selected from aryl, substituted aryl, heteroaryl, or substituted heteroaryl;

wherein, $R^6$ is independently selected at each occurrence from the following groups:
(i) hydrogen
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

wherein, $R^7$ and $R^8$ are independently selected at each occurrence from the following groups:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl; and
(viii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl.

2. A compound selected from compounds of Formula III:

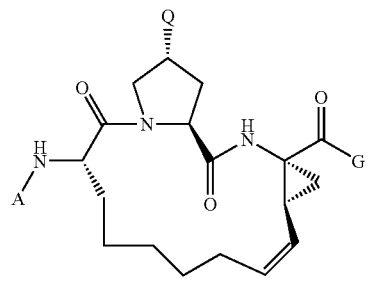

(III)

| Example # | A | Q | G |
|---|---|---|---|
| 16 | 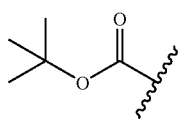 | 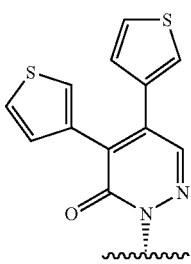 | 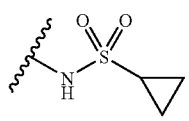 |

-continued
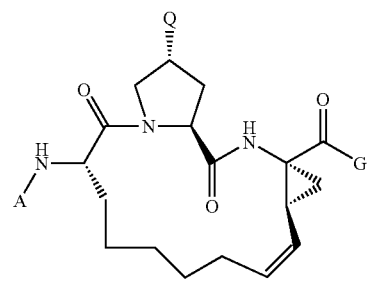
(III)
| Example # | A | Q | G |
|---|---|---|---|
| 17 | 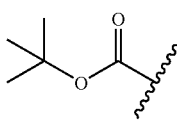 | 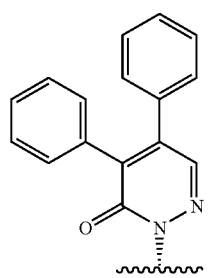 | 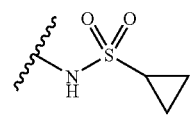 |
| 18 | 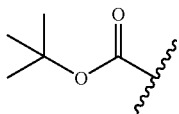 | 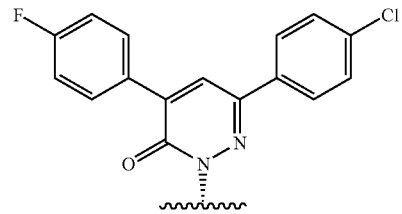 | 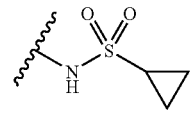 |
| 19 | 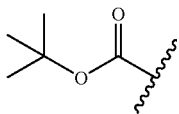 | 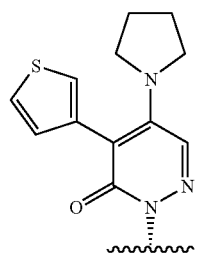 | 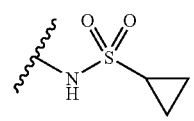 |
| 20 | 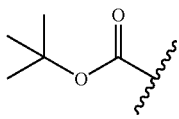 | 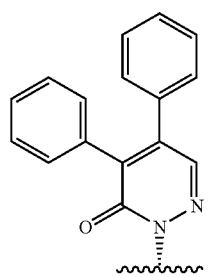 | |

-continued
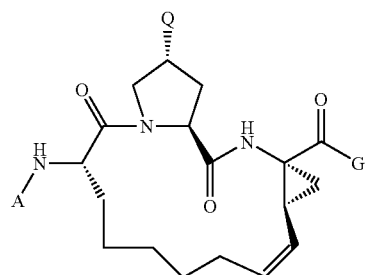
(III)
| Example # | A | Q | G |
|---|---|---|---|
| 21 | 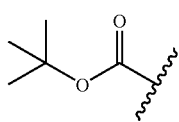 | 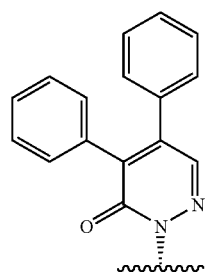 | 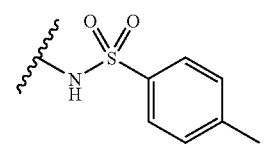 |
| 22 | 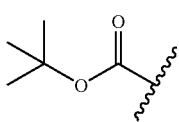 | 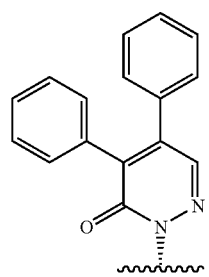 | 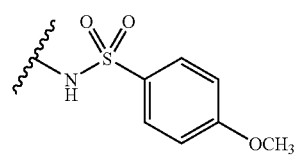 |
| 23 | 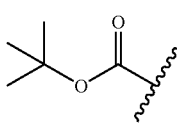 | 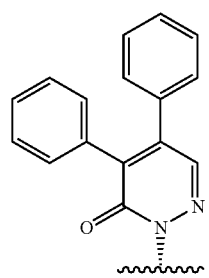 | 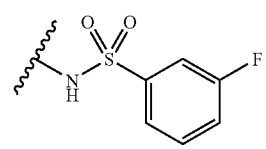 |
| 24 | 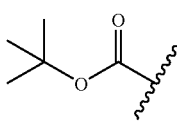 | 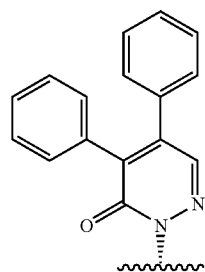 | 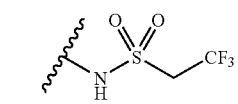 |

-continued
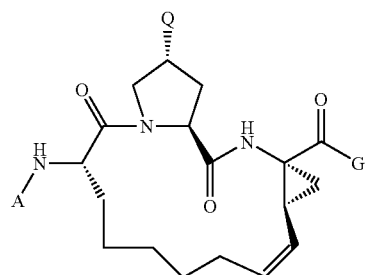
(III)
| Example # | A | Q | G |
|---|---|---|---|
| 25 | 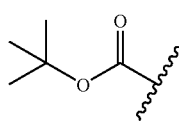 | 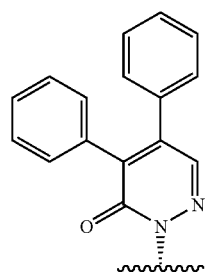 | 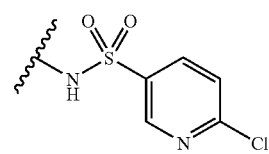 |
| 26 | 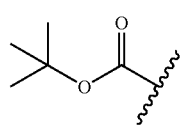 | 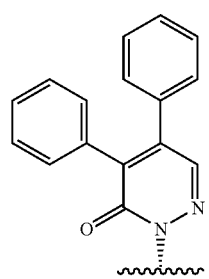 | 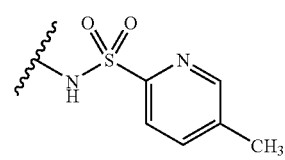 |
| 27 | 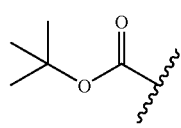 | 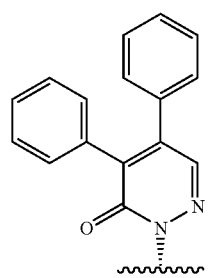 | 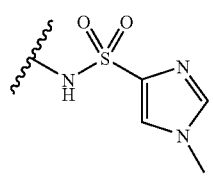 |
| 28 | 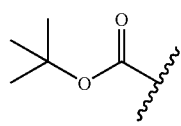 | 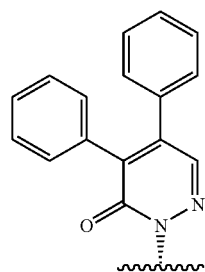 | 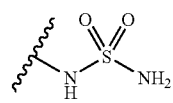 |

-continued
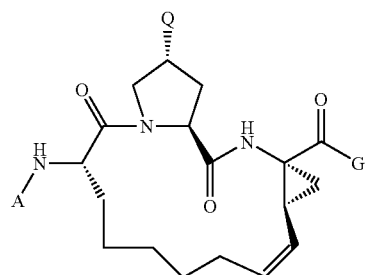
(III)
| Example # | A | Q | G |
|---|---|---|---|
| 29 | 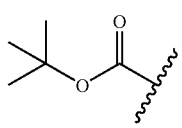 | 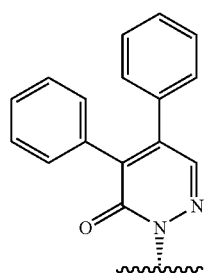 | 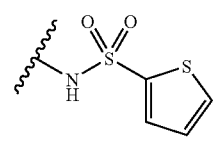 |
| 30 | 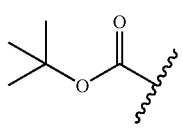 | 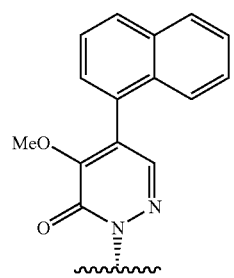 | 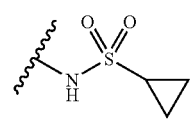 |
| 31 | 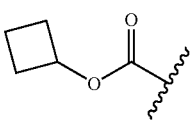 | 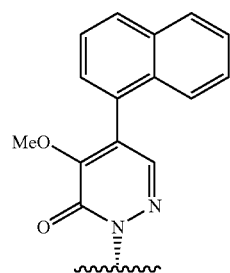 | 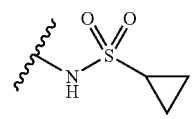 |
| 32 | 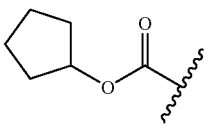 | 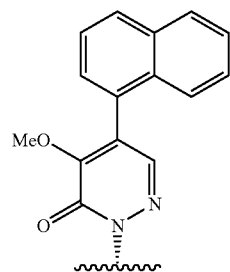 | 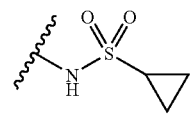 |

-continued
(III)
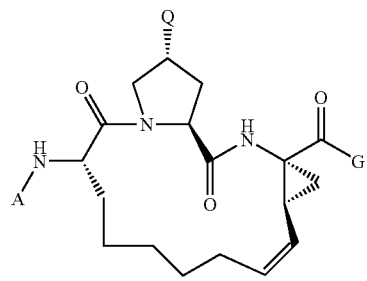
| Example # | A | Q | G |
|---|---|---|---|
| 33 | 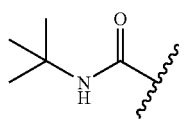 | 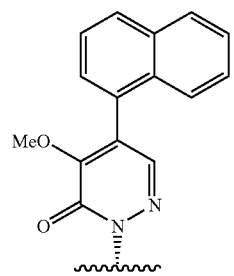 | 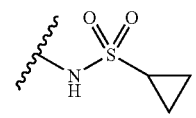 |
| 34 | 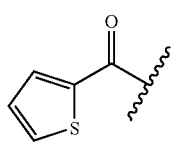 | 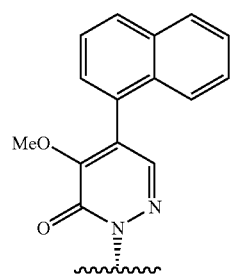 | 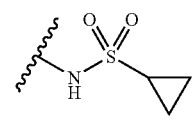 |
| 35 | 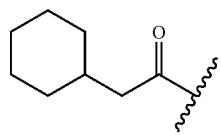 | 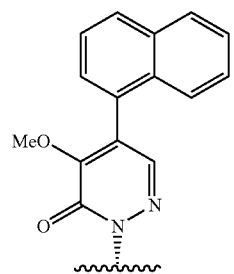 | 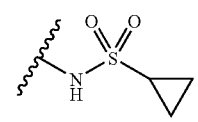 |
| 36 | 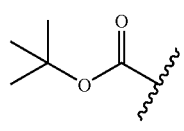 | 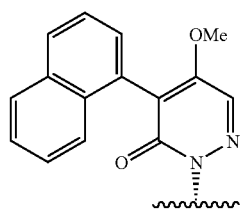 | 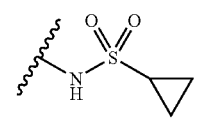 |

-continued
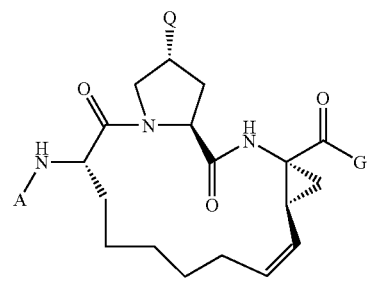
(III)
| Example # | A | Q | G |
|---|---|---|---|
| 37 | 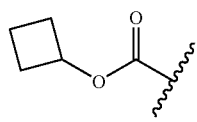 | 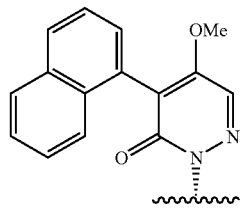 | 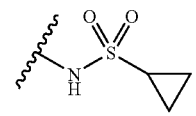 |
| 38 | 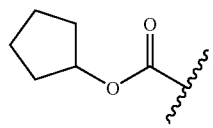 | 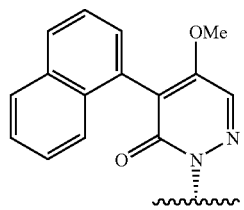 | 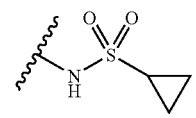 |
| 39 | 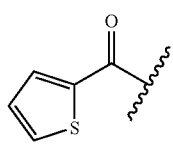 | 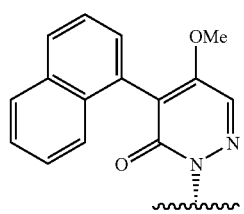 | 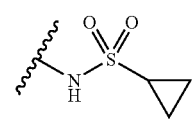 |
| 40 | 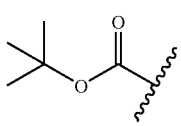 | 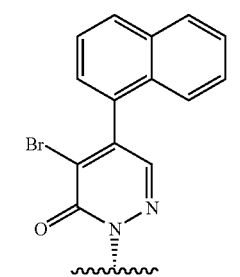 | 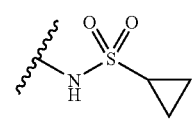 |
| 41 | 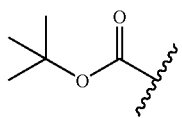 | 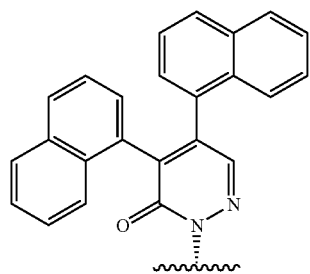 | 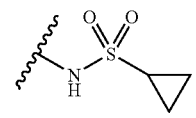 |

(III)
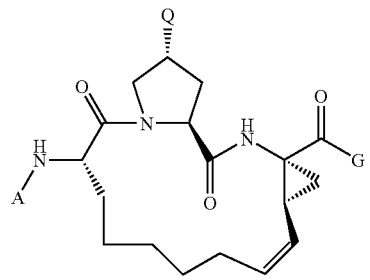
| Example # | A | Q | G |
|---|---|---|---|
| 42 | tert-butyl ester | 4-(naphthalen-1-yl)-2H-pyridazin-3-one | cyclopropanesulfonamide |
| 43 | tert-butyl ester | 4-(3-fluorophenyl)-5-methoxy-2H-pyridazin-3-one | cyclopropanesulfonamide |
| 44 | tert-butyl ester | 4,5-bis(3-fluorophenyl)-2H-pyridazin-3-one | cyclopropanesulfonamide |
| 45 | tert-butyl ester | 5H-pyridazino[4,5-b]indol-1(2H)-one | cyclopropanesulfonamide |

-continued
(III)
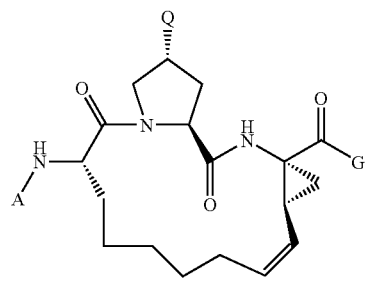
| Example # | A | Q | G |
|---|---|---|---|
| 46 | 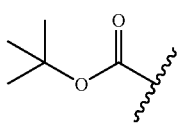 | 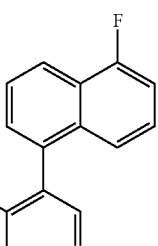 | 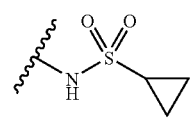 |
| 47 | 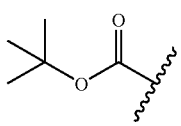 | 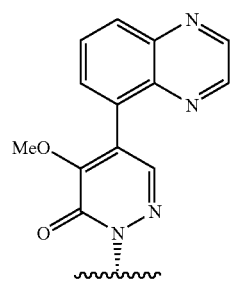 | 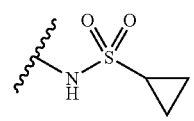 |
| 48 | 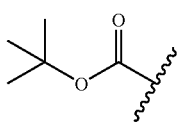 | 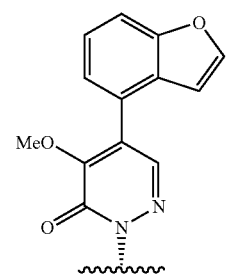 | 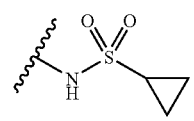 |
| 49 | 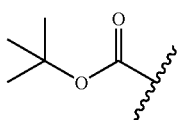 | 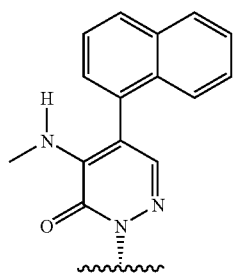 | 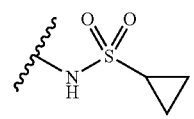 |

-continued
(III)
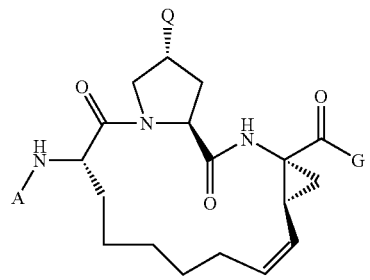
| Example # | A | Q | G |
|---|---|---|---|
| 50 | 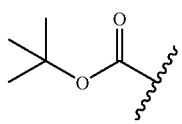 | 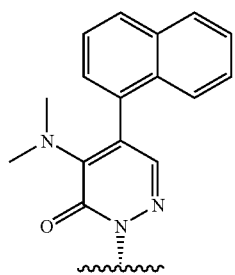 | 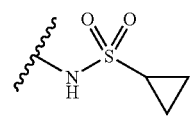 |
| 51 | 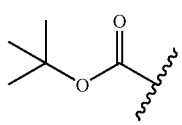 | 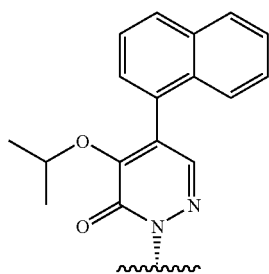 | 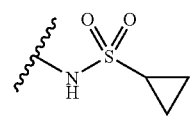 |
| 52 | 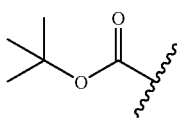 | 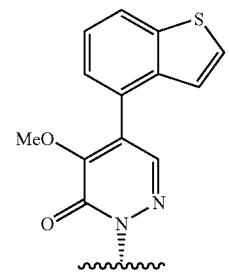 | 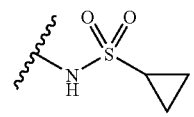 |
| 53 | 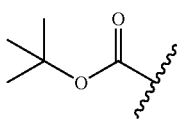 | 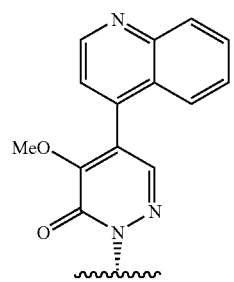 | 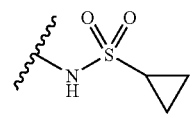 |

-continued
(III)
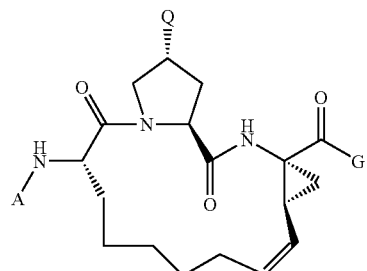
| Example # | A | Q | G |
|---|---|---|---|
| 54 | 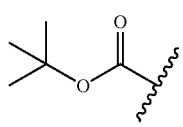 | 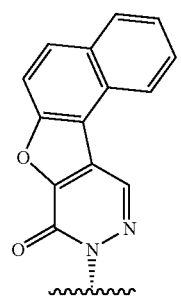 | 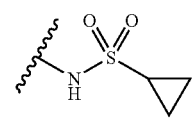 |
| 55 | 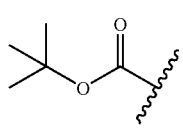 | 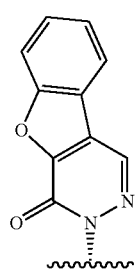 | 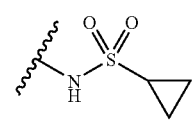 |
| 56 | 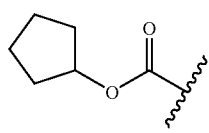 | 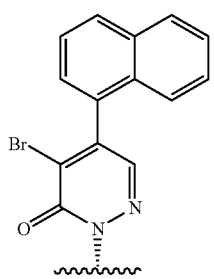 | 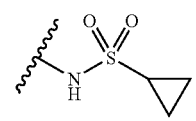 |
| 57 | 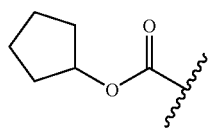 | 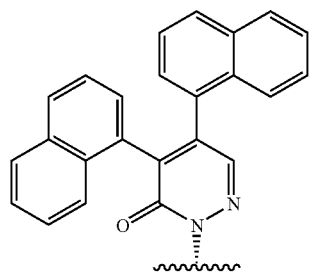 | 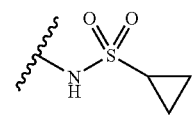 |

-continued
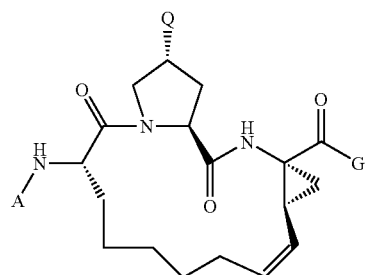
(III)
| Example # | A | Q | G |
|---|---|---|---|
| 58 | 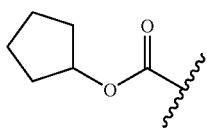 | 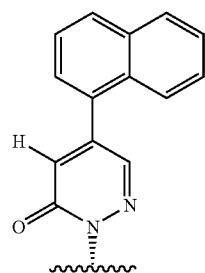 | 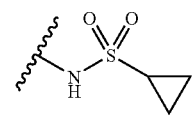 |
| 59 | 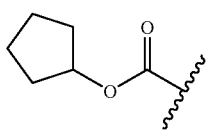 | 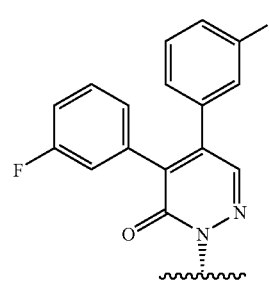 | 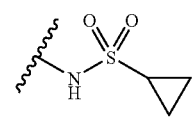 |
| 60 | 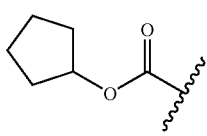 | 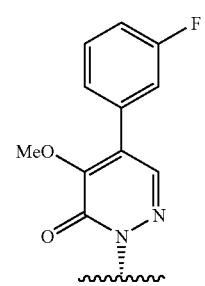 | 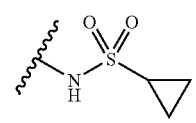 |
| 61 | 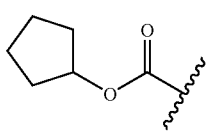 | 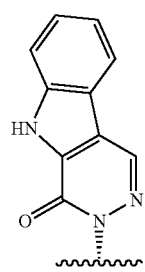 | 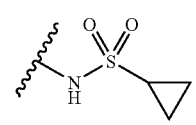 |

-continued
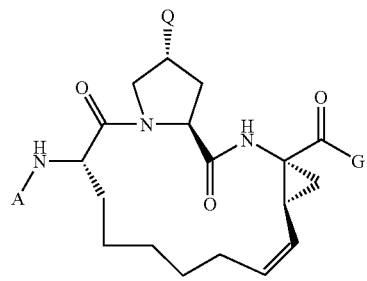
(III)
| Example # | A | Q | G |
|---|---|---|---|
| 62 | 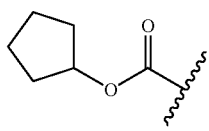 | 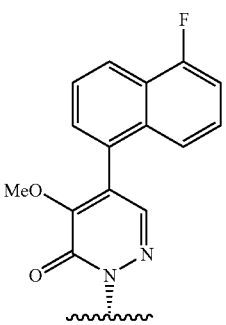 | 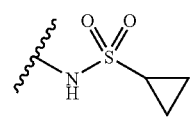 |
| 63 | 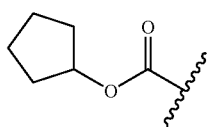 | 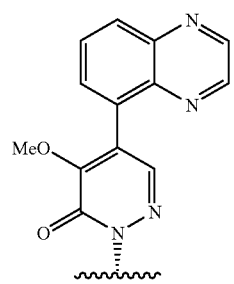 | 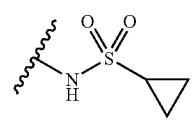 |
| 64 | 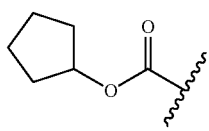 | 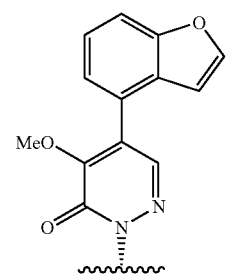 | 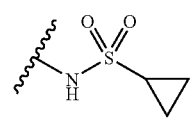 |
| 65 | 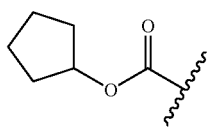 | 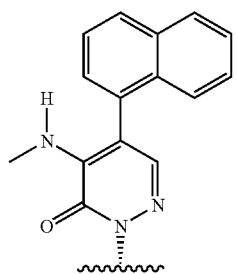 | 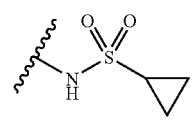 |

-continued
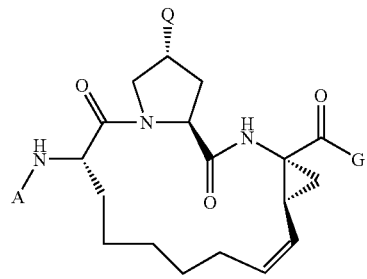
(III)
| Example # | A | Q | G |
|---|---|---|---|
| 66 | 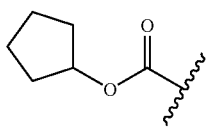 | 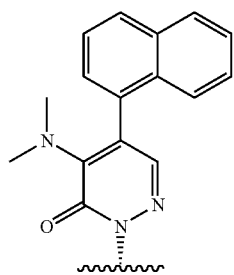 | 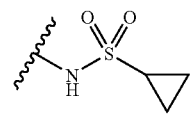 |
| 67 | 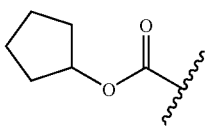 | 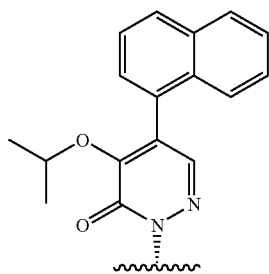 | 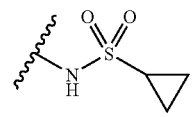 |
| 68 | 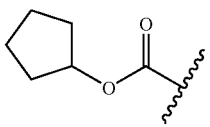 | 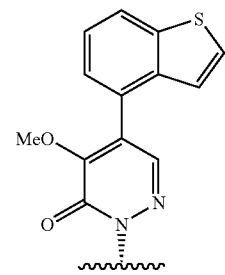 | 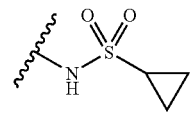 |
| 69 | 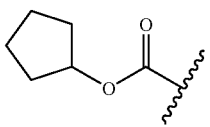 | 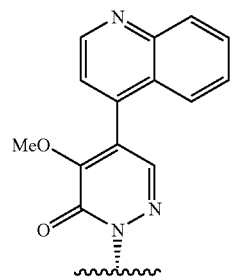 | 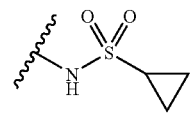 |

-continued
(III)
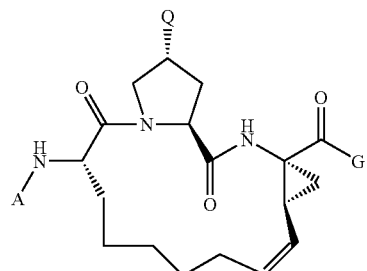
| Example # | A | Q | G |
|---|---|---|---|
| 70 | 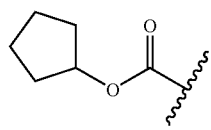 | 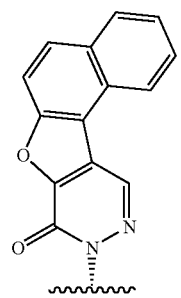 | 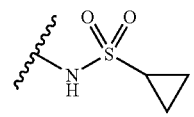 |
| 71 | 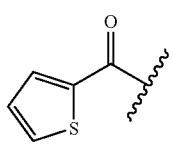 | 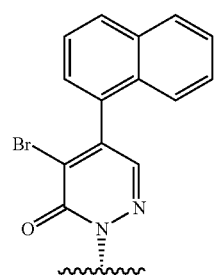 | 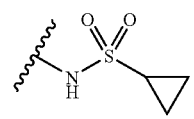 |
| 72 | 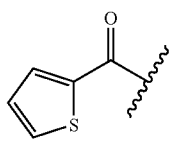 | 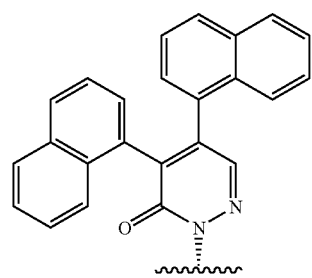 | 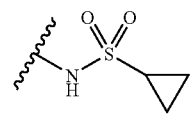 |
| 73 | 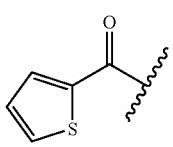 | 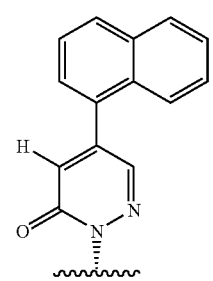 | 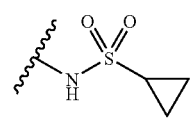 |

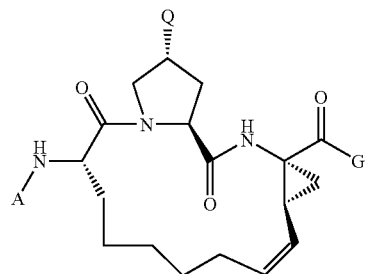
(III)
| Example # | A | Q | G |
|---|---|---|---|
| 74 | 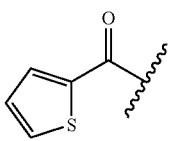 | 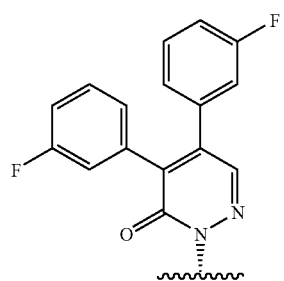 | 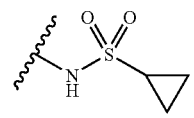 |
| 75 | 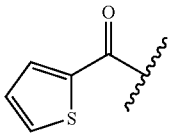 | 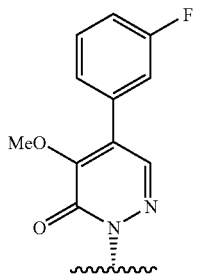 | 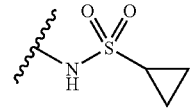 |
| 76 | 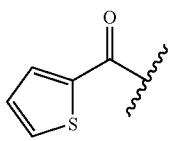 | 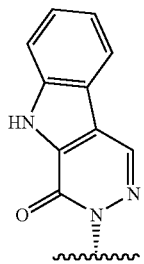 | 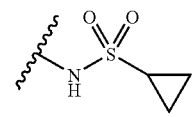 |
| 77 | 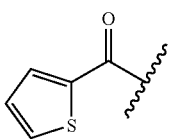 | 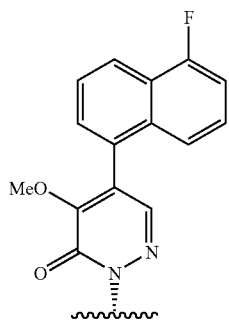 | 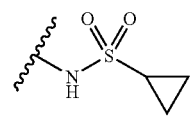 |

-continued
(III)
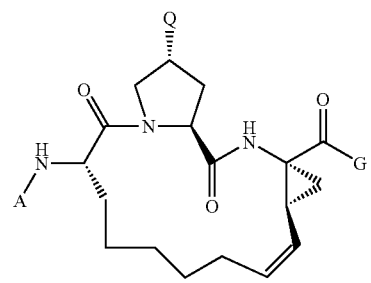
| Example # | A | Q | G |
|---|---|---|---|
| 78 | 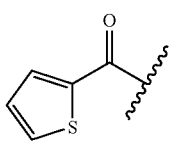 | 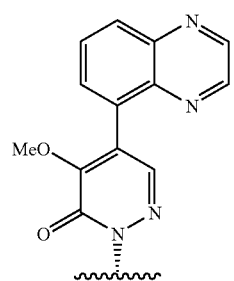 | 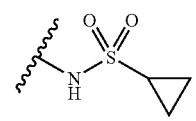 |
| 79 | 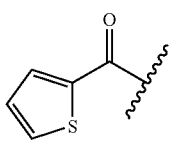 | 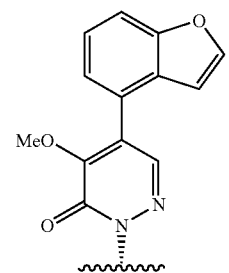 | 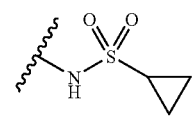 |
| 80 | 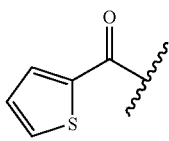 | 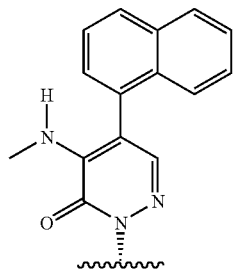 | 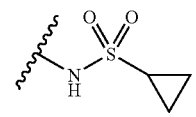 |
| 81 | 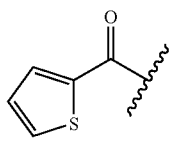 | 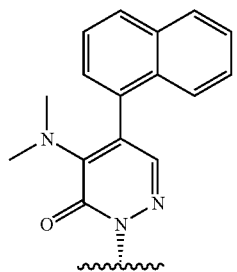 | 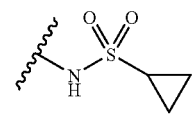 |

-continued
(III)
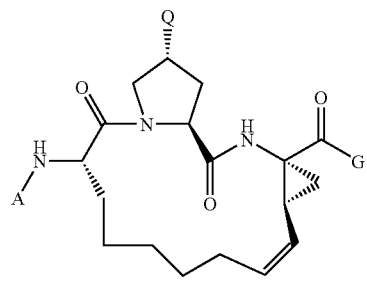
| Example # | A | Q | G |
|---|---|---|---|
| 82 | 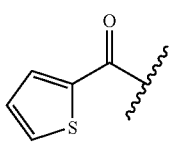 | 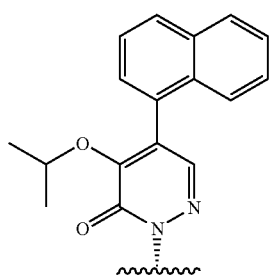 | 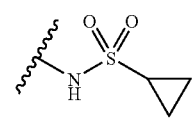 |
| 83 | 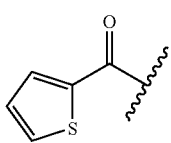 | 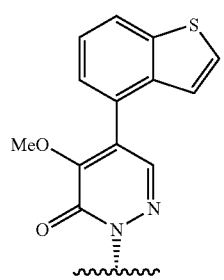 | 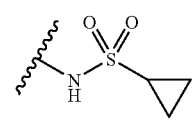 |
| 84 | 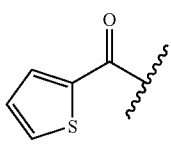 | 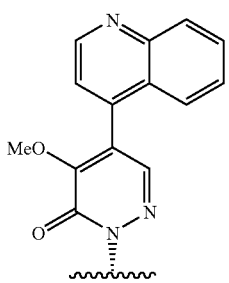 | 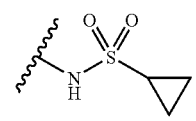 |
| 85 | 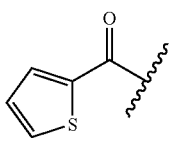 | 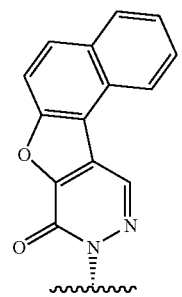 | 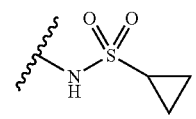 |

-continued
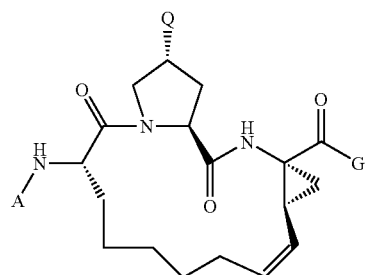
(III)
| Example # | A | Q | G |
|---|---|---|---|
| 86 | 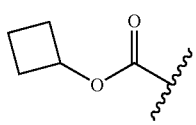 | 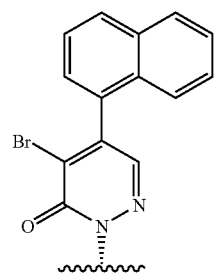 | 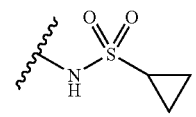 |
| 87 | 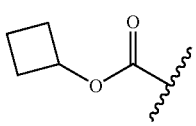 | 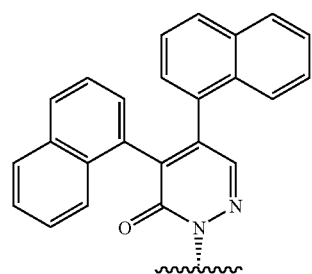 | 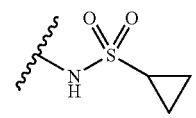 |
| 88 | 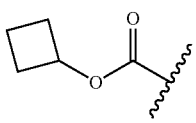 | 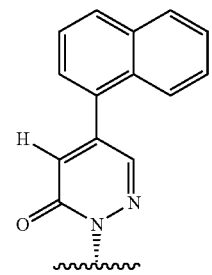 | 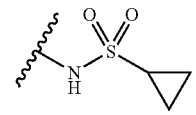 |
| 89 | 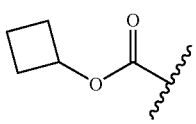 | 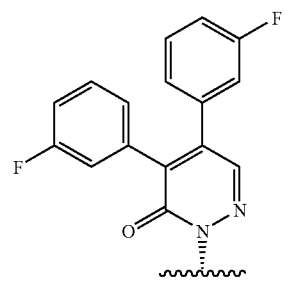 | 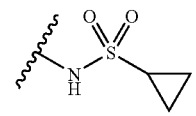 |

(III)
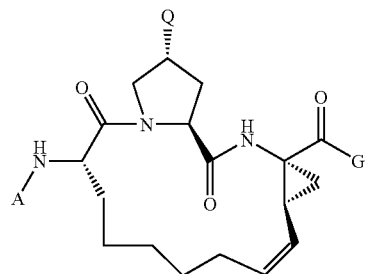
| Example # | A | Q | G |
|---|---|---|---|
| 90 | 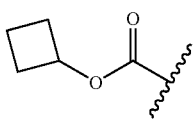 | 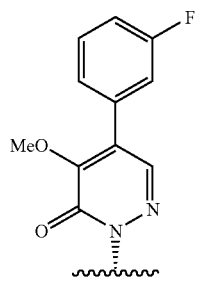 | 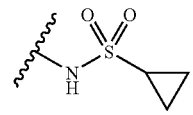 |
| 91 | 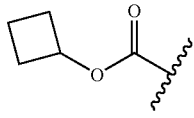 | 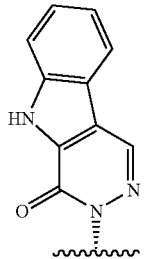 | 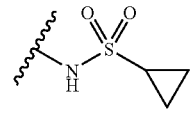 |
| 92 | 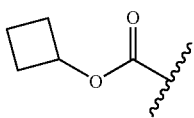 | 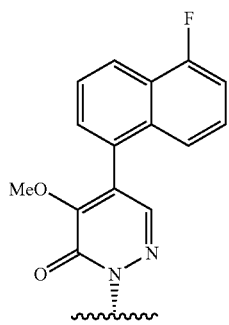 | 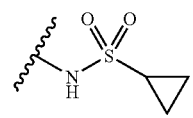 |
| 93 | 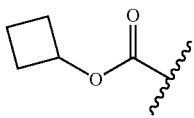 | 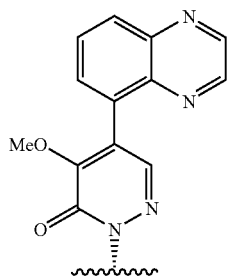 | 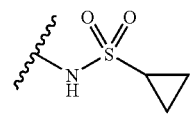 |

-continued
(III)
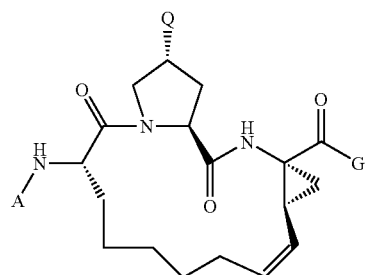
| Example # | A | Q | G |
|---|---|---|---|
| 94 | 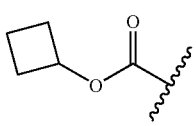 | 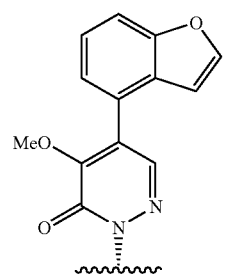 | 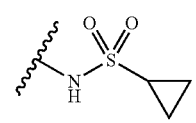 |
| 95 | 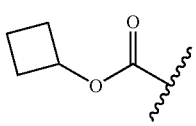 | 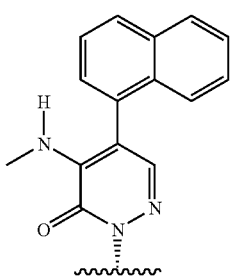 | 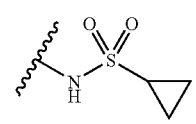 |
| 96 | 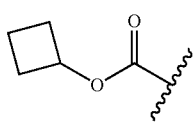 | 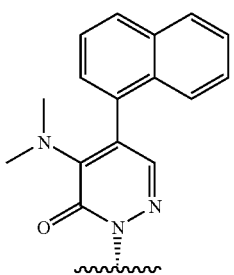 | 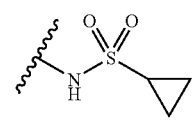 |
| 97 | 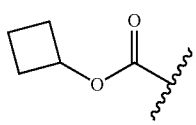 | 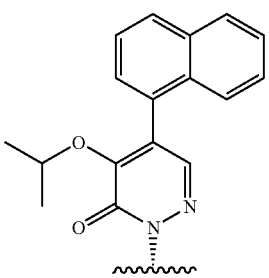 | 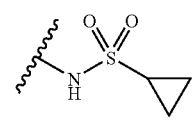 |

-continued
(III)
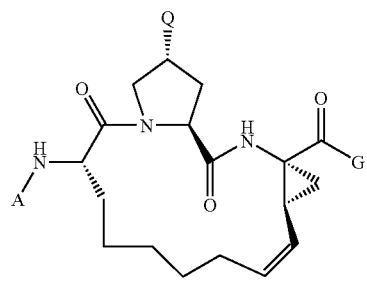
| Example # | A | Q | G |
|---|---|---|---|
| 98 | 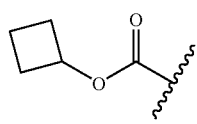 | 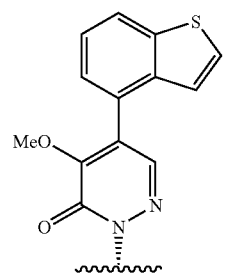 | 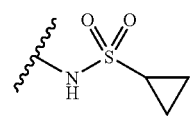 |
| 99 | 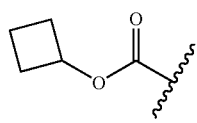 | 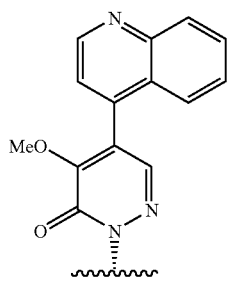 | 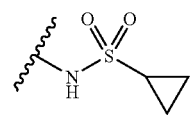 |
| and | | | |
| 100 | 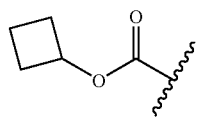 | 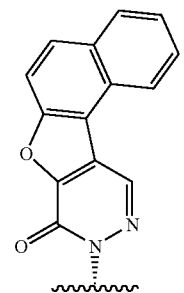 | 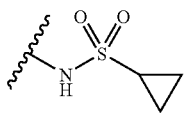 |
3. A method of treating a hepatitis C viral infection in a subject, comprising administering to the subject an inhibitory amount of a compound according to claim 1.
4. A method of inhibiting the replication of hepatitis C virus, the method comprising supplying a hepatitis C viral NS3 protease inhibitory amount of a compound of claim 1.
* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Forward Primer

<400> SEQUENCE: 1
gctgcggcct gtcgagct                                                    18

<210> SEQ ID NO 2

```
<211> LENGTH: 19
<212> TYPE: DNA
<213> ORGANISM: Artificial Sequence
<220> FEATURE:
<223> OTHER INFORMATION: Reverse Primer

<400> SEQUENCE: 2
caaggtcgtc tccgcatac                                              19

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
cgaagctcca ggactgcacg atgct                                       25
```